(12) United States Patent
Ong et al.

(10) Patent No.: US 8,993,298 B1
(45) Date of Patent: Mar. 31, 2015

(54) DNA POLYMERASES

(75) Inventors: Jennifer Ong, Salem, MA (US);
Thomas C. Evans, Jr., Topsfield, MA (US); Nathan Tanner, Peabody, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/600,408

(22) Filed: Aug. 31, 2012

(51) Int. Cl.
*C12N 9/12* (2006.01)
*C12N 9/96* (2006.01)
*C12P 19/34* (2006.01)
*C12Q 1/68* (2006.01)

(52) U.S. Cl.
CPC ............. *C12N 9/1252* (2013.01); *C12N 9/96* (2013.01); *C12P 19/34* (2013.01); *C12Q 1/6844* (2013.01)
USPC .......................................................... 435/194

(58) Field of Classification Search
None
See application file for complete search history.

(56) References Cited

U.S. PATENT DOCUMENTS

| | | | |
|---|---|---|---|
| 5,736,373 A | 4/1998 | Hamilton | |
| 5,814,506 A | 9/1998 | Kong et al. | |
| 5,830,714 A | 11/1998 | Swaminathan et al. | |
| 5,834,253 A | 11/1998 | Hong et al. | |
| 6,013,451 A * | 1/2000 | Wong et al. | 435/6.11 |
| 6,165,765 A | 12/2000 | Hong et al. | |
| 6,485,909 B1 | 11/2002 | Hong et al. | |
| 6,818,431 B1 | 11/2004 | Hong et al. | |
| 7,282,328 B2 | 10/2007 | Kong et al. | |
| 7,504,220 B2 | 3/2009 | Gu et al. | |
| 7,662,594 B2 | 2/2010 | Kong et al. | |
| 7,700,283 B2 | 4/2010 | Evans et al. | |
| 7,829,284 B2 | 11/2010 | Kong et al. | |
| 2011/0201056 A1 | 8/2011 | Evans et al. | |
| 2012/0015405 A1 | 1/2012 | Reichert et al. | |
| 2012/0202276 A1 | 8/2012 | Davidson et al. | |
| 2012/0208240 A1 | 8/2012 | Bauer et al. | |
| 2012/0258501 A1 | 10/2012 | Bauer et al. | |

FOREIGN PATENT DOCUMENTS

WO    WO03025132 A2    3/2003

OTHER PUBLICATIONS

Pavlov et al., "Helix-hairpin-helix motifs confer salt resistance and processivity on chimeric DNA polymerases", PNAS, 2002, 99(21):13510-13515.*
Notomi, et al., Nucleic Acids Research, 28:E63 (2000).
Henikoff, et al., PNAS, 89(22): 10915-10919 (1992).
Gill, et al., Nucleosides, Nucleotides and Nucleic Acids, 27:224-243 (2008).
Nagamine, et al., Mol. Cell. Probes, 16:223-229 (2002).
Lage, et al., Genome Research, 13(2): 294-307 (2003).
Aviel-Ronen, et al., BMC Genomics, 7:312 (2006).
Rothberg, et al., Nature, 475(7356): 348-352 (2011).
Adessi, et al., Nucleic Acids Research, 28:E87 (2000).
Aliotta, et al., Genet Anal, 12(5-6): 185-195 (1995).

* cited by examiner

*Primary Examiner* — Suzanne M Noakes
(74) *Attorney, Agent, or Firm* — New England Biolabs, Inc; Harriet M. Strimpel

(57) ABSTRACT

Novel proteins having DNA polymerase are described which have utility in amplification reactions and have improved properties over Bst polymerase such as for example enhanced reverse transcriptase activity.

16 Claims, 5 Drawing Sheets

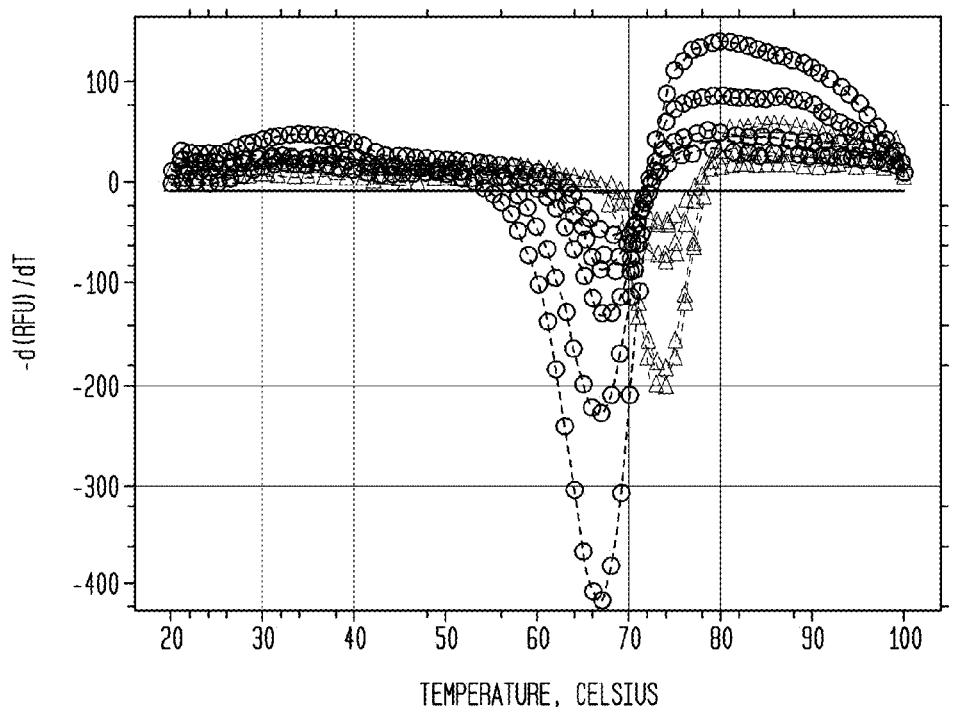
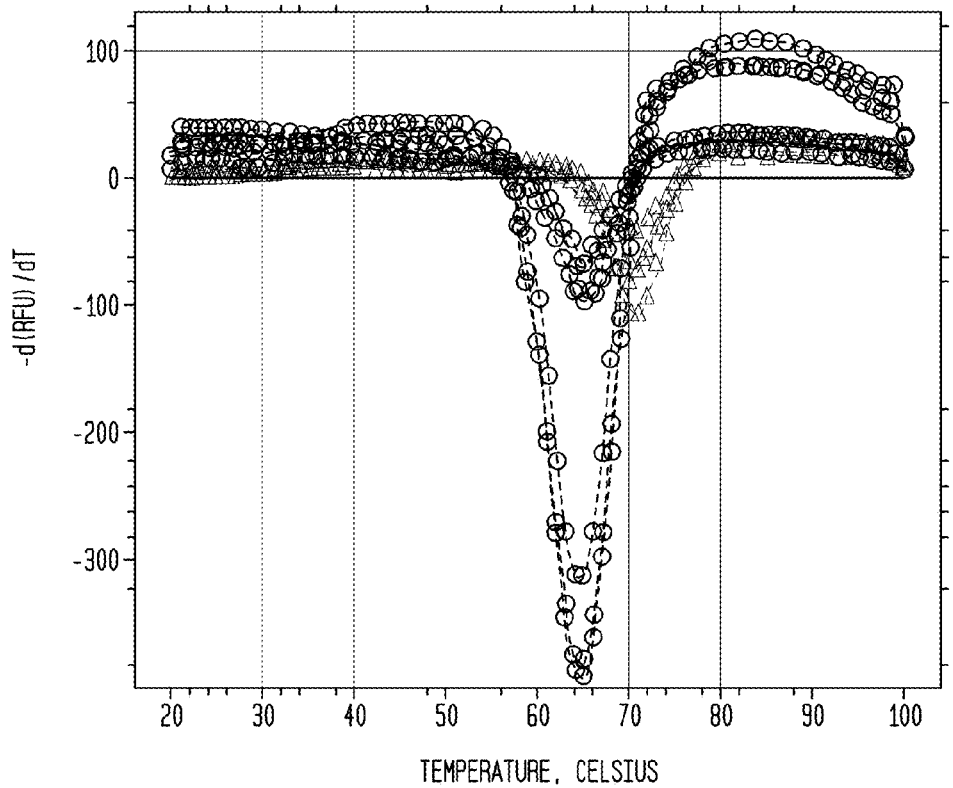

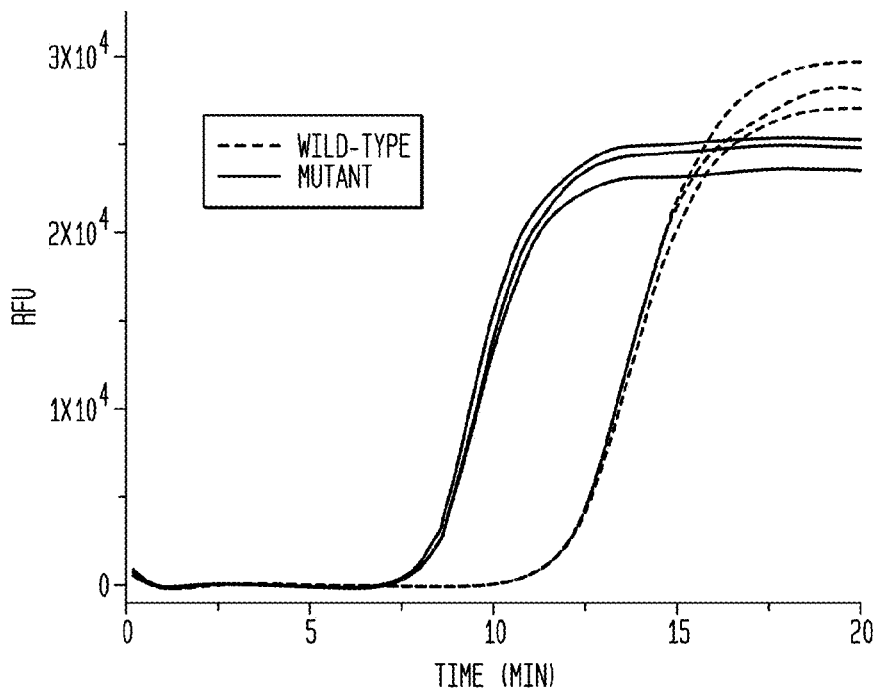
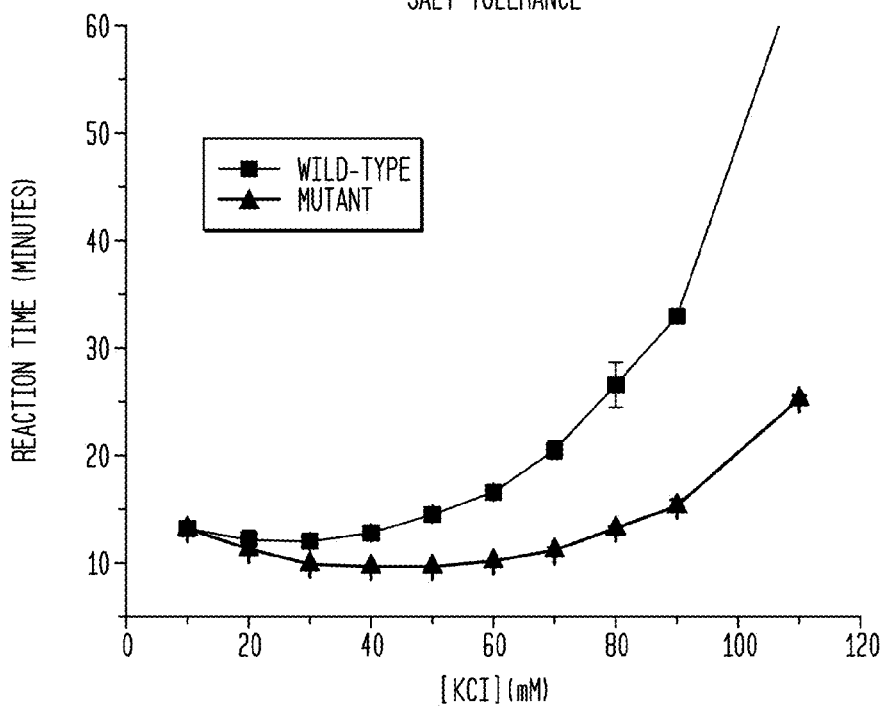

TEMPERATURE

STORAGE STABILITY

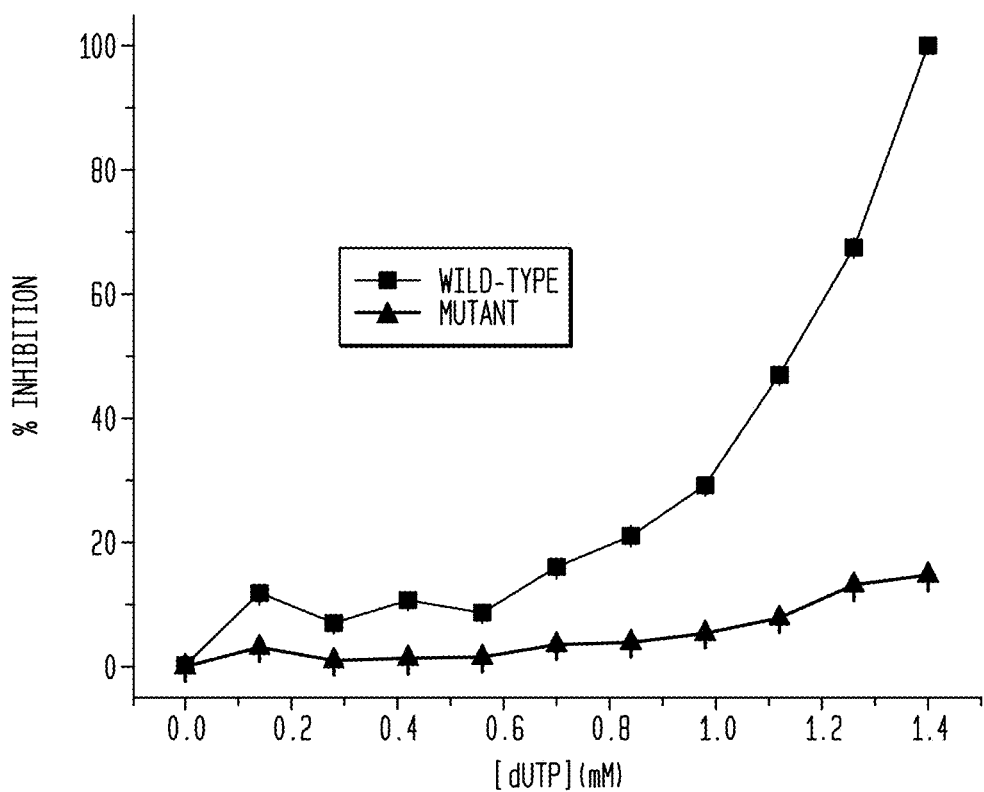

DNA POLYMERASES

BACKGROUND

A DNA polymerase from *Geobacillus stearothermophilus* has been described in Kong, et al., U.S. Pat. No. 5,814,506 (1998). This enzyme, which is a Bst DNA polymerase belongs to the Family A DNA polymerase and shares about 45% sequence identity with its better known relative Taq DNA polymerase. Whereas Taq DNA polymerase is from a hyperthermophilic organism and is able to survive the high temperatures of the polymerase chain reaction, the Bst DNA polymerase reported in Kong, et al., is from a thermophilic organism, is optimally active between 60-70° C., but does not survive the high temperatures of PCR. The full length (FL) Bst DNA polymerase is 876 amino acid residues and has 5'-3' endonuclease activity but not 3'-5' exonuclease activity. The large fragment (LF) of Bst DNA polymerase lacks both 5'-3' exonuclease activity and 3'-5' exonuclease activity and is only 587 amino acid residues with 289 amino acids being deleted from the N-terminal end. The full length Bst DNA polymerase and the large fragment Bst DNA polymerase have been found to be useful for isothermal amplification techniques and DNA sequencing.

SUMMARY OF EMBODIMENTS OF THE INVENTION

Compositions and methods are described herein that utilize novel improved synthetic DNA polymerases for isothermal DNA replication and other uses, the improvements being determined by comparison with a naturally occurring Bst polymerase.

In one embodiment, a protein consisting of a synthetic protein with polymerase properties is provided having at least 99% sequence identity with any of SEQ ID NOs:1-126.

In a second embodiment, a protein comprises an amino acid sequence that has at least 98% sequence identity with at least one sequence selected from SEQ ID NOs:1-42.

In a third embodiment, a protein comprises an amino acid sequence that has at least 99% sequence identity with at least one sequence selected from SEQ ID NOs:43-84.

In a fourth embodiment, a protein comprises an amino acid sequence that has greater than 98% sequence identity with at least one sequence selected from SEQ ID NOs:85-126.

In embodiment 5, a protein according to any of embodiments 1 through 4, further comprises DNA polymerase activity.

In embodiment 6, a protein according to any of embodiments 1 through 4 is capable of replicating DNA.

In embodiment 7, a protein according to embodiment 6, is capable of replicating DNA in an isothermal amplification reaction.

In embodiment 8, a protein according to any of embodiments 1 through 4 is contained in a storage buffer, or a reaction buffer.

In embodiment 9, a protein according to embodiment 8, is contained in a buffer that further comprises temperature dependent inhibitor of polymerase activity.

In embodiment 10, a protein according to any of embodiments 1 through 4 fused to a peptide either directly or by means of a linker.

In embodiment 11, a protein according to any of embodiments 1 through 4, is contained in a buffer that further comprises dNTPs.

In embodiment 12, a DNA encodes the protein of any of the embodiments 1 through 4.

In embodiment 13, a host cell comprises the DNA according to embodiment 12.

In embodiment 14, a method for determining whether a protein according to any of embodiments 1 through 4 has improved polymerase activity compared with a wild type Bst polymerase; includes synthesizing a protein according to any of the embodiments 1 through 4; and determining polymerase activity.

In embodiment 15, a method according to embodiment 14 is described which includes characterizing the polymerase activity; and determining in comparison with a wild type Bst polymerase, at least one improved property selected from the group consisting of: thermostability; stability in storage; tolerance to salt; performance in isothermal amplification; strand displacement; kinetics; processivity; fidelity; altered ribonucleotide incorporation; 2'-deoxyuridine 5'-triphosphate incorporation; reverse transcriptase activity (Rtx) and modified nucleotide incorporation.

In embodiment 16, a method is described which includes:
(a) selecting a protein according to any of embodiments 1 through 4; and
(b) expressing the protein as a fusion protein with an additional peptide at an end of the amino acid sequence, the additional peptide attached either directly or by means of a linker.

In embodiment 17, a method of isothermal amplification is described that includes:
(a) providing a reaction mixture comprising a protein according to any of embodiments 1 through 4, primers and dNTPs;
(b) combining a target DNA with the preparation; and
(c) amplifying the target DNA at a temperature less than 90° C.

In embodiment 18, a method according to embodiment 17, is described where the amplification reaction results in a quantitative measure of the amount of target DNA in the preparation.

In embodiment 19, a protein according to any of embodiments 1 through 4 is further characterized by one or more improved properties for isothermal amplification compared with a wild type Bst polymerase, selected from the group consisting of:
(a) an increased reaction speed where the increase is at least 10% and as much as 200%, 500% or 1000%;
(b) an increased temperature stability in the range of 50° C.-100° C., 50° C.-90° C. or 60° C.-90° C.;
(c) an increased salt tolerance in the range of 10 mM-1 M, or 20 mM-200 or 500 mM monovalent salt;
(d) an increase in storage stability at 25° C., retaining at least 50% activity over 45, weeks, over 1 year, or over 2 years;
(e) an enhanced dUTP tolerance of the range of an increase of 50% to 100% dUTP; and
(f) an increased reverse transcriptase activity by at least 2 fold.

BRIEF DESCRIPTION OF THE FIGURES

FIGS. 1A and 1B show melt peaks for a Bst DNA polymerase FL or LF and a synthetic DNA polymerases.

FIG. 1A shows the melt peaks for a synthetic DNA polymerase (FL) which has a melting temperature (Tm)=73.5° C. (Δ) and the parent Bst DNA polymerase (FL) has a Tm=68° C. (O).

FIG. 1B shows the melt peaks for a Bst DNA polymerase LF (O) which has a Tm=65° C. while the synthetic DNA polymerase (Δ) has a Tm=70° C.

The reactions were performed in 1× Detergent-free ThermoPol™ Buffer (New England Biolabs, Ipswich, Mass.) and 1× SYPRO Orange (Life Technologies, Carlsbad, Calif.).

FIGS. 2A-E show how the properties of a synthetic DNA polymerase can be screened for significant beneficial properties using an isothermal amplification protocol (Notomi, et al., *Nucleic Acids Research,* 28:E63 (2000)) and lambda DNA.

FIG. 2A shows an analysis of reaction speed. The synthetic DNA polymerase shows faster DNA amplification than the parent Bst DNA polymerase.

FIG. 2B shows the results of an assay to determine salt tolerance. The time in which the amplification reaction took to reach a threshold level of product was graphed against increasing KCl concentration in the reaction. The synthetic DNA polymerase was more tolerant to changes in salt concentration than the parent Bst DNA polymerase.

Figure 2C:
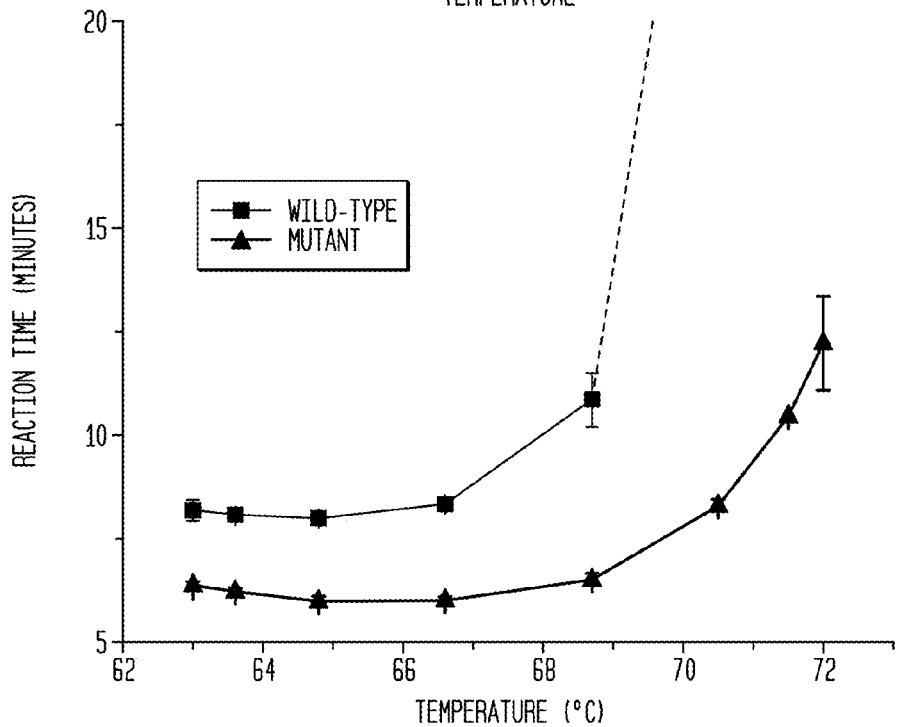

FIG. 2C shows the results of an assay to determine an increase in thermostability of a synthetic DNA polymerase by at least 3° C. compared with the Bst DNA polymerase. The time in which the amplification reaction took to reach a threshold level of product was graphed against increasing reaction temperature. The synthetic DNA polymerase was able to amplify DNA at a higher temperature than the naturally occurring Bst DNA polymerase.

Figure 2D:
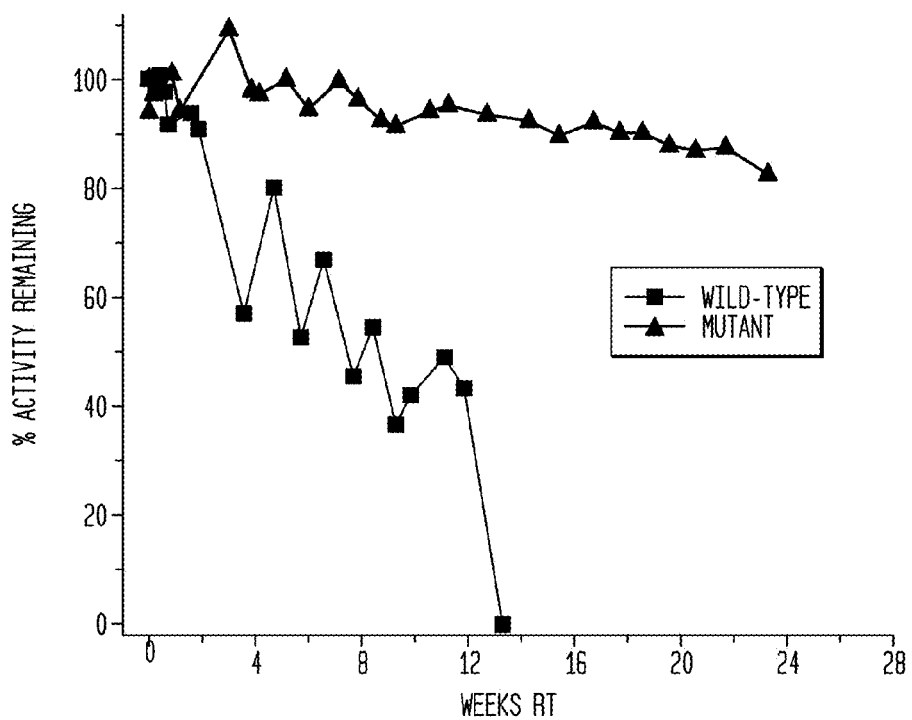

FIG. 2D shows the results of an assay for storage stability in which a synthetic DNA polymerase remains stable for at least 28 weeks at room temperature (22° C.) versus about 13 weeks for the Bst DNA polymerase (8000 U/ml for each enzyme was used).

FIG. 2E shows the results of an assay for dUTP tolerance in which a Bst DNA polymerase is significantly inhibited by increasing amounts of dUTP while the synthetic DNA polymerase activity is relatively stable as dUTP levels increase (1.4 mM dUTP corresponds to complete substitution of dTTP with dUTP). The ability to incorporate dUTP without inhibition of the polymerase is a useful feature of a DNA polymerase for various applications including strand modification and differentiation. Thermophilic archaeal DNA polymerases do not amplify DNA effectively in the presence of dUTP. Taq DNA polymerase can incorporate dUTP into substrate but Taq DNA polymerase is not suitable for isothermal amplification because it is not capable of the requisite amount of strand displacement.

3A and 3B shows that the DNA polymerase mutants described herein with improved polymerase activity also have improved reverse transcriptase activity.

Figure 3A:
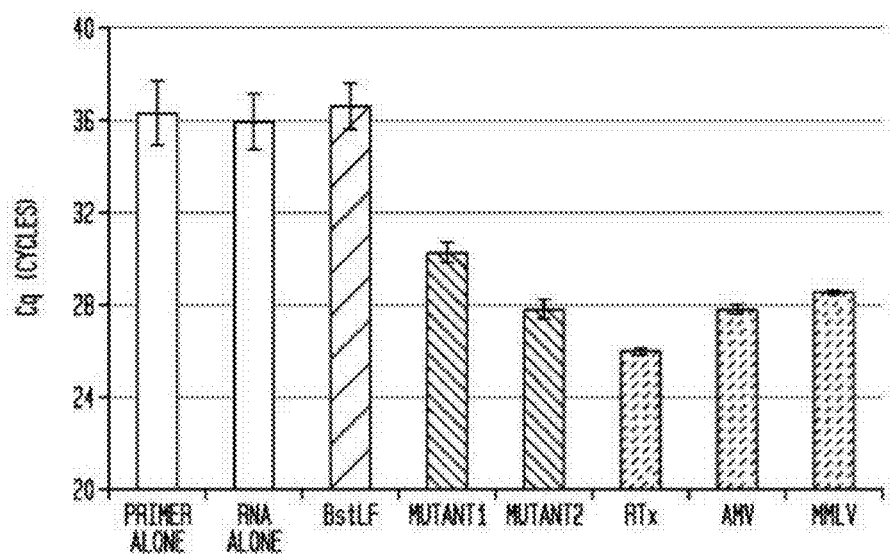

FIG. 3A shows the results of determining Rtx activity using RT-qPCR. The lower the value of cycles (Cq) the greater the activity of the Rtx. From left to right, the bar chart shows Primer alone, RNA alone, Bst polymerase large fragment (BstLF), 2 mutants of the DNA polymerase described herein, Rtx, Avian Myeloblastosis Virus Reverse Transcriptase (AMV) and Moloney Murine Leukemia Virus Reverse Transcriptase (MMLV).

Figure 3B:
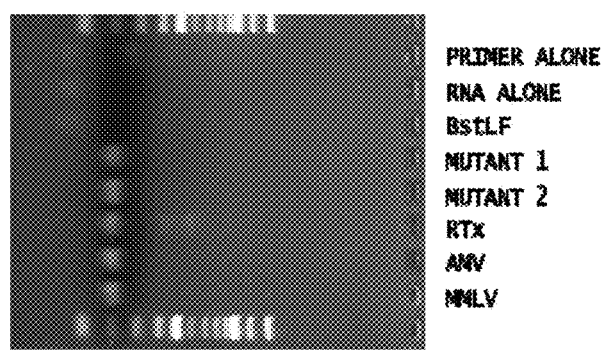

FIG. 3B shows gel electrophoresis of amplified DNA resulting from an RNA template and BstLF DNA polymerase or mutants. The lanes are labeled left to right as follows: Primer alone, RNA alone, BstLF, Mutant 1 and 2, Rtx, AMV and MMLV.

DETAILED DESCRIPTION OF THE EMBODIMENTS

As used herein, the term "synthetic" with respect to proteins or peptides refers to a non-naturally occurring amino acid sequence that is generated either by expression of a gene encoding the non-naturally occurring amino acid sequence or is generated by chemical synthesis. The gene encoding the non-naturally occurring amino acid sequence may be generated, for example, by mutagenesis of a naturally occurring gene sequence or by total chemical synthesis.

A "variant" or "mutant" protein refers to a protein that differs from a parent protein by at least one amino acid that is the product of a mutation. A variant polymerase is intended to include a "synthetic" protein and vice versa as the context permits. The examples utilize a variant DNA polymerase but it will be understood to a person of ordinary skill in the art that the assays described in the examples are applicable to analyzing synthetic proteins also.

"Non-naturally occurring" refers to a sequence or protein that at the date in which the embodiments of the invention are presented herein, no naturally occurring amino acid sequence corresponding to the alleged non-naturally occurring amino acid has been described in the publically available databases.

"Isothermal amplification" refers to a DNA amplification protocol that is conducted at a temperature below 90° C. after an initial denaturation step, where an initial denaturation step is required.

98% percent sequence identity may be calculated by any method known in the art such as for example, using the BLOSUM62 matrix and the methods described in Henikoff, et al., *PNAS,* 89 (22):10915-10919 (1992).

We have developed a set of proteins that have properties of the type observed for DNA polymerases belonging to Family A DNA polymerases. These proteins have improved polymerase activity when compared with wild type Bst DNA polymerase.

The DNA polymerase may have one or more improved properties as compared with the wild type Family A DNA polymerases such as those including one of specific activity, reaction speed, thermostability, storage stability, dUTP tolerance, salt tolerance and reverse transcriptase activity.

The proteins described herein generally retain DNA binding properties making these synthetic proteins useful for example as DNA detection reagents. The variants may be screened using at least one method described in Examples 1-6, or by other screening methods common used in the art, so as to identify those variants having at least one of the functional properties that are at least typical of a Family A DNA polymerase and/or have one or more improved properties selected from at least one of specific activity, reaction speed, thermostability, storage stability, dUTP tolerance and salt tolerance, increased performance in isothermal amplification, non-interference of pH during sequencing, improved strand displacement, altered processivity, altered ribonucleotide incorporation, altered modified nucleotide incorporation, reverse transcriptase activity, and altered fidelity when compared to the corresponding parent polymerase. The improved properties of these mutant enzymes have been demonstrated to enhance the performance of sequencing platforms (for example, the Ion Torrent™ sequencer (Life Technologies, Carlsbad, Calif.)). The improved properties of these mutant enzymes enhance their use in isothermal amplification for diagnostic applications.

The DNA polymerase variants and synthetic proteins described herein may be expressed in suitable non-native host cells such as *E. coli* according to standard methods known in the art. To facilitate expression, the variant DNA polymerase may additionally have a methionine in front of the first amino acid at the N-terminal end. Host cells may be transformed with DNA encoding the variant optionally contained in a suitable expression vector (see New England Biolabs catalog 2009-10 or 2011-12 for expression vectors known in the art for this purpose). Transformation is achieved using methods well known in the art.

The DNA polymerase variants and synthetic proteins characterized herein may further be modified by additions and/or deletions of peptides at their N-terminal and/or C-terminal ends. For example, fusion of a peptide to a synthetic protein may include fusion of one or more of a DNA binding domain (such as Sso7d from archaea), an exonuclease domain (such as amino acids 1-289 of Bst DNA polymerase), a peptide lacking exonuclease activity (for example a mutated exonuclease domain similar to amino acids 1-289 of Bst DNA polymerase), an affinity binding domain such as a Histidine tag, chitin binding domain, or intein, and a solubility tag such as maltose binding domain or an antibody. The addition of a peptide fused to an end of the amino acid sequence of the DNA polymerase may be used to enhance one or more of the functional features described in Examples 1-6. Aptamers may be added to the preparation of the mutant DNA polymerase to enhance temperature sensitive amplification.

The proteins described herein may be stored in a storage or reaction buffer that includes a detergent such as a non-ionic detergent, a zwitterionic detergent, an anionic detergent or a cationic detergent. The storage or reaction buffer may further include one or more of: a polynucleotide, for example, an aptamer for facilitating a hot start; polynucleotide primers, dNTPs, target polynucleotides; additional polymerases including additional DNA polymerases; RNA polymerases and/or reverse transcriptases; crowding agents such as polyethylene glycol; and/or other molecules known in the art for enhancing the activity of the DNA polymerase variants.

The DNA polymerase variant and synthetic proteins may be used for DNA synthesis, DNA repair, cloning and sequencing (see for example U.S. Pat. No. 7,700,283 and US Application Publication No. US 2011/0201056) and such as illustrated in the examples and also for temperature dependent amplification methods. Examples of isothermal amplification methods in addition to loop-mediated isothermal amplification (LAMP) used in the present examples include helicase dependent amplification (HDA) (see for example U.S. Pat. No. 7,829,284, U.S. Pat. No. 7,662,594, and U.S. Pat. No. 7,282,328); strand displacement amplification (SDA); nicking enzyme amplification reaction, recombinase polymerase amplification, padlock amplification, rolling circle amplification, and multiple displacement amplification (see for example Gill, et al., *Nucleosides, Nucleotides and Nucleic Acids*, 27:224-243 (2008)). The proteins described herein may also be used in sample preparation for sequencing by synthesis techniques known in the art. The proteins may also be used in quantitative amplification techniques known in the art that may be performed at a temperature at which the variant or synthetic protein effectively polymerizes nucleotides.

EXAMPLES

The Examples provided below illustrate assays for the Bst DNA polymerase variants described herein.

Example 1

Assay for Determining the Properties of a Variant DNA Polymerase (a) Loop-Mediated Isothermal Amplification (LAMP)

The properties of a variant polymerase can be determined using an isothermal amplification procedure such as a LAMP protocol (Nagamine, et al., *Mol. Cell. Probes*, 16:223-229 (2002); Notomi, et al., *Nucleic Acids Research*, 28:E63 (2000)).

The LAMP reaction used bacteriophage λ genomic DNA (New England Biolabs, Ipswich, Mass.) as the template. The LAMP primers used here were:

FIP (5'-CAGCCAGCCGCAGCACGTTCGCTCATAG-GAGATATGGTAGAGCCGC-3') (SEQ ID NO:127),
BIP (5' GAGAGAATTTGTACCACCTCCCAC-CGGGCACATAGCAGTCCTAGGG ACAGT-3') (SEQ ID NO:128),
F3 (5'-GGCTTGGCTCTGCTAACACGTT-3') (SEQ ID NO:129),
B3 (5'-GGACGTTTGTAATGTCCGCTCC-3') (SEQ ID NO:130),
LoopF (5'-CTGCATACGACGTGTCT-3') (SEQ ID NO:131),
LoopB (5'-ACCATCTATGACTGTACGCC-3') (SEQ ID NO:132).

The LAMP reaction used 0.4 U-0.2 U variant Polymerase/μL, 1.6 μM FIP/BIP, 0.2 μM F3/B3, 0.4 μM LoopF/LoopB, and 5 ngλ DNA in a buffer containing 1× Detergent-free ThermoPol, 0.1% Tween 20, 6-8 mM MgSO$_4$ and 1.4 μMdNTP. The reaction was followed by monitoring turbidity in real time using the Loopamp® Realtime Turbidimeter LA-320c (SA Scientific, San Antonio, Tex.) or with a CFX96™ Real-Time fluorimeter (Bio-Rad, Hercules, Calif.). The reaction conditions were varied to determine the optimum range that the variant DNA polymerase could perform LAMP. This was compared with the parent Bst DNA polymerase. The parent Bst DNA polymerase was typically used at 65° C. in these LAMP reaction conditions. However, the temperature was varied to determine the optimum temperature for a particular variant. Different salt conditions and rates of reaction were tested and variants identified which were 10%-50% faster than the parent polymerase and had an increased salt tolerance to as much as 200 mM KCl. The results are shown in FIG. 2.

(b) DNA Polymerase Activity Assay Using Modified Nucleotides in a Comparison of the Activity of a Fusion Variant Protein with Exonuclease Activity, with Full Length Parent Bst Polymerase This assay was used to determine the activity of the variant polymerase having exonuclease activity as a result of an additional 289 amino acid sequence at the N-terminal end that has been described in detail for parent DNA Bst polymerase. The activity was measured by incorporation of a radioactive $^3$H-dTTP in a DNA substrate using various concentrations of a variant polymerase. A DNA polymerase reaction cocktail (40 μl) was prepared by mixing 30 nM single-stranded M13mp18, 82 nM primer #1224 (5'-CGCCAGGGTTTTC-CCAGTCACGAC-3') (SEQ ID NO:133), 200 μM dATP, 200 μM dCTP, 200 μM dGTP, and 100 or 200 μM dTTP including 0.6 to 0.8 μCi [3H]-dTTP. The DNA polymerase reaction cocktail was mixed with DNA polymerase (2.2 to 8.7 ng for the parent Bst DNA polymerase (FL), 0.27 to 1 ng for the fusion variant, or 2.5 to 20 ng for the parent Bst DNA polymerase LF), or water for the no enzyme control, and incubated at 65° C. for 5 minutes. Reactions were halted and precipitated by acid precipitation as follows. A 30 μl aliquot of each reaction was spotted onto 3 mm Whatman discs and immediately submerged into cold 10% Trichloroacetic acid (TCA) in 1 L beaker in an ice bucket. A total counts control was spotted as described but not washed. Filters were washed three times with cold 10% TCA for 10 minutes with vigorous shaking and twice with room temperature 95% isopropanol for 5 minutes. Filters were dried under a heat lamp for 10 minutes and counted using a scintillation counter. The pmoles of dNTPs incorporated were calculated for each sample from the fraction of radioactive counts incorporated, multiplied by the total amount of dNTPs and the volume of the reaction.

A tenfold increase in specific activity of the fusion variant polymerase was found compared with the parent FL Bst polymerase where the fusion variant DNA polymerase was present in the mixture at 506,000 U/mg while the parent Bst DNA polymerase was present at 48,000 U/mg (1 unit=incorporation of 10 nmol dNTP in 30 minutes at 65° C.).

A 15% increase in activity of the variant polymerase compared with the parent BstLF DNA polymerases was observed in which the variant DNA polymerase was present in the mixture at 370,000 U/mg and the parent DNA polymerase Bst (LF) was present at 260,000 U/mg.

Example 2

Variant DNA Polymerase Thermostability

The thermostability of the variant DNA polymerase was assessed by incubating the polymerase at differing temperatures followed by performing either one or both of the DNA polymerase assay described in Example 1. The results are shown in FIG. 2C.

Example 3

Inhibitor Resistance of the Variant DNA Polymerase

The resistance of a variant DNA polymerase to inhibitors such as blood is determined by adding increasing concentrations of the inhibitor into the DNA polymerase assay and determining the change, if any, in the apparent specific activity of the protein. The DNA polymerase assay was performed as described in Example 1 at 65° C.

Another inhibitor of DNA polymerase is dUTP which is used to prevent carryover contamination in isothermal amplification by replacing dTTP. In this case it is desirable for the polymerase to be insensitive to dUTP inhibition so as to utilize dUTP as a substrate for LAMP. FIG. 2E shows that the mutant polymerase can efficiently utilize dUTP while the wild type Bst polymerase is inhibited by substituting dTTP with dUTP in the amplification reaction.

Example 4

Increased Resistance to High Salt Concentration

The resistance of a variant DNA polymerase to increased salt concentration was determined by adding increasing concentrations of salt (for example, KCl or NaCl) to the DNA polymerase assay described in Example 1 and determining the activity of the protein at 65° C. and comparing its activity to parent Bst DNA polymerase (see FIG. 2B).

Example 5

Increased Stability in Storage

The stability of a variant DNA polymerase during storage was determined by incubating the enzyme in storage buffer (10 mMTris-HCl pH 7.5, 50 mM KCl, 1 mM Dithiothreitol, 0.1 mM EDTA, 50% Glycerol, 0.1% Triton X-100) at a temperature ranging from 4° C. to 65° C. for a time period ranging from 1 day to 28 weeks, and assaying DNA polymerase activity remaining after storage using the LAMP method described in Example 1. The remaining activity was compared to a sample stored at −20° C. for the same amount of time. The stability of the variant was then compared to the stability of parent Bst DNA polymerase (See FIG. 2D). When this period was extended to 60 weeks, no detectable loss of activity of the mutants was observed even in the absence of glycerol.

Example 6

Assay for Determining the Melting Temperature of a Variant Polymerase for Comparison with a Parent DNA Polymerase Using a SYPRO Orange Assay The assay was performed as follows: Each 50 µl reaction contains 1× Detergent-free ThermoPol Buffer (20 mM Tris-HCl pH 8.8, 10 mM $(NH_4)_2SO_4$, 10 mM KCl, 2 mM $MgSO_4$, 1× SYPRO Orange protein gel stain, and DNA polymerase concentrations ranging from 2.2 to 17.5 µg (parent BstLF mutant) or 0.6 to 4.8 µg (parent Bst FL mutant). The reactions were placed in a CFX96 Real-Time System. The temperature was raised 1° C. per second from 20° C. to 100° C., and the fluorescence (in the FRET channel) was read at each temperature. Here, the melting temperature (Tm) is the inflection point of the sigmodial curve of fluorescence plotted against temperature. The inverted first derivative of the fluorescence emission in FIGS. 1A and 1B is shown in relation to temperature, where the location of the minima corresponded to the value of the melting temperature (see FIG. 1).

Example 7

Whole Genome Amplification Using a Variant Bst DNA Polymerase

The variant DNA polymerase can be tested for suitability in whole genome amplification using the methods termed hyperbranched strand displacement amplification (Lage, et al., *Genome Research,* 13 (2):294-307 (2003)) or multiple-strand displacement amplification (Aviel-Ronen, et al., *BMC Genomics,* 7:312 (2006)).

Example 8

DNA Sequencing on a Semiconductor Device Using a Variant DNA Polymerase

The variant DNA polymerase can be tested for its suitability in DNA sequencing, for example, as described in Rothberg, et al., *Nature,* 475(7356):348-352(2011)), an integrated semiconductor device enabling non-optical genome sequencing.

Example 9

Solid-Phase DNA Amplification Using a Variant Polymerase

Variant DNA polymerase can be tested for its suitability in solid-phase DNA amplification, for example as described in (Adessi, et al., *Nucleic Acids Research,* 28:E87 (2000)), which describes a method for the amplification of target sequences with surface bound oligonucleotides.

Example 10

Enhanced Reverse Transcriptase Activity

The reverse activity of the mutant Bst DNA polymerase was determined using a two-step RT-qPCR assay. The first step was for complementary DNA (cDNA) synthesis using the mutant enzymes and various traditional reverse transcriptases. The second measures the amount of synthesized cDNA by qPCR. The RT step was performed using 6 uM Hexamer (Random Primer Mix, New England Biolabs, Ipswich, Mass.) as primers in Isothermal Amplification Buffer (New England Biolabs, Ipswich, Mass.) supplemented with 6 mM Mg and 200 uM dNTP with 0.1 ug Jurkat Total RNA (Life Technologies, Carlsbad, Calif.) and incubated at 65° C. for 20 minutes. 1 ul of the RT product was added to qPCR reaction for GAPDH gene with 200 nM of forward (5'AGAACGGGAAGCTTGTCATC) (SEQ ID NO:134) and reverse primer (5'CGAACATGGGGGCATCAG) (SEQ ID NO:135), 200 uM dNTP, 1.25 unit of Taq DNA polymerase in 25 ul of 1× Standard Taq Buffer (New England Biolabs, Ipswich, Mass.) containing 2 uM of dsDNA-binding fluorescent dye SYTO®9 (Life Technologies, Carlsbad, Calif.). The PCR cycles were: 95° C. for 1 minute, then 50 cycles at 95° C. for 10 seconds, 61° C. for 15 seconds and 68° C. for 30 seconds, and a final step of 68° C. for 5 minutes. The PCR was performed on a CFX96 Real-Time PCR machine and the Cq value was obtained as an indication of the amount of specific cDNA being synthesized (FIG. 3A). Mutant 1 and mutant 2 (4$^{th}$ and 5$^{th}$ bar from left in bar chart) make abundant cDNA as indicated by having Cq values similar to that of traditional RTs (6$^{TH}$, 7$^{th}$, and 8$^{th}$ bar from left) in qPCR. Wild type BstLF (3rd bar from the left) is the same as controls (1st and 2$^{nd}$ bar from left) without RT. After completion of the PCR reaction, 10 ul of PCR product was analyzed by electrophoresis in a 1.5% agarose gel (FIG. 3B) to verify the size of the PCR product. The lanes from left to right are primer alone, RNA alone, BstLF, mutant 1, mutant 2, Rtx, AMV and MMLV. Mutant 1, mutant 2 and all RTs (Rtx, AMV and MMLV) lanes gave a band of expected size (207 base pairs) but no specific band with wild type BstLF or controls. These results demonstrate that mutant 1 and mutant 2 has much improved Rtx activity compared to wild type BstLF.

All references cited herein are incorporated by reference.

What is claimed is:

1. A variant of Bst (*Bacillus stearothermophilus*) polymerase, wherein the variant, that excludes a large fragment Bst polymerase having a wild type sequence with a 289 amino acid truncation deleted from the N-terminal end, is characterized by one or more improved properties for isothermal amplification compared with a wild type Bst polymerase or the large fragment Bst polymerase, selected from the group consisting of:
   (a) an increased reaction speed at 65° C., where the increase is at least 10%
   (b) an increased temperature stability in the range of 50° C.-100° C.;
   (c) an increased salt tolerance in the range of 10 mM-1 M monovalent salt;
   (d) an increase in storage stability at 25° C., retaining at least 50% activity over 45 weeks;
   (e) an enhanced dUTP tolerance of the range of an increase of 50% to 100% dUTP; or
   (f) an increased reverse transcriptase activity by at least 2 fold
   wherein the variant polymerase lacks 3' to 5' exonuclease activity and comprises an amino acid sequence that has at least 99% identity to a sequence selected from the group consisting of SEQ ID NOs: 43, 47, 48, 65, 75, 85, 86, 111, 112 and 117.

2. A variant according to claim 1, further comprising DNA polymerase activity.

3. A variant according to claim 1, wherein the protein is capable of replicating DNA.

4. A variant according to claim 3, wherein the protein is capable of replicating DNA in an isothermal amplification reaction.

5. A variant according to claim 1 in a storage buffer, or a reaction buffer.

6. A variant according to claim 5, wherein the buffer further comprises temperature dependent inhibitor of polymerase activity.

7. A variant according to claim 1, fused to a peptide either directly or by means of a linker.

8. A variant according to claim 5, wherein the buffer further comprises dNTPs.

9. A variant according to claim 1, having at least two or three or four or five or six of the improved properties.

10. A DNA encoding the protein of claim 1.

11. A host cell comprising the DNA according to claim 10.

12. A method for determining whether a protein according to claim 1 has improved polymerase activity compared with a wild type Bst polymerase; comprising synthesizing a protein according to claim 1; and determining the polymerase activity.

13. A method according to claim 12, wherein characterizing the polymerase activity further comprises: determining in comparison with a wild type Bst polymerase, at last one improved property selected from the group consisting of: thermostability; stability in storage; tolerance to salt; performance in isothermal amplification; strand displacement; kinetics; processivity; fidelity; altered ribonucleotide incorporation; 2'-deoxyuridine 5'-triphosphate incorporation; reverse transcriptase activity; and modified nucleotide incorporation.

14. A method, comprising:
   (a) selecting a protein according to claim 1; and
   (b) expressing the protein as a fusion protein with an additional peptide at an end of the amino acid sequence, the additional peptide attached either directly or by means of a linker.

15. A method of isothermal amplification, comprising:
   (a) providing a reaction mixture comprising a protein according to claim 1, primers and dNTPs;
   (b) combining a target DNA with the preparation; and
   (c) amplifying the target DNA at a temperature less than 90° C.

16. A method according to claim 15, wherein the amplification reaction results in a quantitative measure of the amount of target DNA in the preparation.

* * * * *

UNITED STATES PATENT AND TRADEMARK OFFICE
CERTIFICATE OF CORRECTION

PATENT NO. : 8,993,298 B1  
APPLICATION NO. : 13/600408  
DATED : March 31, 2015  
INVENTOR(S) : Jennifer Ong et al.

Page 1 of 1

It is certified that error appears in the above-identified patent and that said Letters Patent is hereby corrected as shown below:

In the Claims

At column 283, claim number 1, line number 24, replace "99%" with "98%".

Signed and Sealed this  
Thirtieth Day of June, 2015

Michelle K. Lee  
*Director of the United States Patent and Trademark Office*

SEQUENCE LISTING

<160> NUMBER OF SEQ ID NOS: 135

<210> SEQ ID NO 1
<211> LENGTH: 587
<212> TYPE: PRT
<213> ORGANISM: Artificial Sequence
<220> FEATURE:
<223> OTHER INFORMATION: Synthetic construct

<400> SEQUENCE: 1

Glu Glu Glu Glu Lys Pro Leu Glu Asp Ile Glu Phe Ala Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Asn
        35                  40                  45

Val Asn Glu His Gly Arg Phe Phe Leu Arg Pro Glu Thr Ala Leu Ala
    50                  55                  60

Ser Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Thr Ala Glu Asp Ile Ala Ala Val Ala Lys Met Lys
        115                 120                 125

Gln Tyr Glu Ala Val Arg Ser Asp Glu Ala Val Tyr Gly Lys Gly Val
    130                 135                 140

Lys Arg Ser Leu Pro Asp Glu Gln Ala Leu Ala Glu His Leu Val Arg
145                 150                 155                 160

Lys Ala Ala Ala Ile Trp Ala Leu Glu Gln Pro Phe Met Asp Asp Leu
                165                 170                 175

Arg Lys Asn Glu Gln Asp Arg Leu Leu Thr Glu Leu Glu Gln Pro Leu
            180                 185                 190

Ala Ser Ile Leu Ala Glu Met Glu Phe Thr Gly Val Asn Val Asp Thr
        195                 200                 205

Lys Arg Leu Glu Gln Met Gly Ser Glu Leu Ala Glu Gln Leu Lys Glu
    210                 215                 220

```
Gln Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
            245                 250                 255

Val Leu Lys Lys Thr Lys Thr Gly Tyr Ser Thr Ser Ala Asp Val Leu
        260                 265                 270

Glu Lys Leu Ala Pro His His Glu Ile Val Glu Asn Ile Leu His Tyr
    275                 280                 285

Arg Gln Leu Gly Lys Leu Gln Ser Thr Tyr Ile Glu Gly Leu Leu Lys
290                 295                 300

Val Val His Pro Asp Thr Gly Lys Val His Thr Arg Phe Asn Gln Ala
305                 310                 315                 320

Leu Thr Gln Thr Gly Arg Leu Ser Ser Ala Glu Pro Asn Leu Gln Asn
            325                 330                 335

Ile Pro Ile Arg Leu Glu Glu Gly Arg Lys Ile Arg Gln Ala Phe Val
        340                 345                 350

Pro Ser Glu Pro Asp Trp Leu Ile Phe Ala Ala Asp Tyr Ser Gln Ile
    355                 360                 365

Glu Leu Arg Val Leu Ala His Ile Ala Asp Asp Asp Asn Leu Ile Glu
370                 375                 380

Ala Phe Gln Arg Asp Leu Asp Ile His Thr Lys Thr Ala Met Asp Ile
385                 390                 395                 400

Phe His Val Ser Glu Glu Val Thr Ala Asn Met Arg Arg Gln Ala
            405                 410                 415

Lys Ala Val Asn Phe Gly Ile Val Tyr Gly Ile Ser Asp Tyr Gly Leu
        420                 425                 430

Ala Gln Asn Leu Asn Ile Thr Arg Lys Glu Ala Ala Glu Phe Ile Glu
    435                 440                 445

Arg Tyr Phe Ala Ser Phe Pro Gly Val Lys Glu Tyr Met Glu Asn Ile
450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
        500                 505                 510

Asp Ile Ile Lys Lys Ala Met Ile Asp Leu Ala Ala Arg Leu Lys Glu
    515                 520                 525

Glu Gln Leu Gln Ala Arg Leu Leu Leu Gln Val His Asp Glu Leu Ile
530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
            565                 570                 575

Tyr His Tyr Gly Pro Thr Trp Tyr Asp Ala Lys
            580                 585

<210> SEQ ID NO 2
<211> LENGTH: 587
<212> TYPE: PRT
<213> ORGANISM: Artificial Sequence
<220> FEATURE:
<223> OTHER INFORMATION: Synthetic construct
```

```
<400> SEQUENCE: 2

Ala Glu Glu Glu Lys Pro Leu Glu Glu Met Glu Phe Thr Asp Val Asp
1               5                   10                  15

Glu Ile Thr Glu Glu Met Leu Ala Asp Lys Ala Ala Leu Val Val Glu
            20                  25                  30

Val Gln Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Val Ala Trp Leu Glu Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Asp Asp Val Ala Val Ala Lys Met Lys
            115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ile Arg Ala Leu Glu Gln Pro Phe Ile Asp Glu Leu
                165                 170                 175

Arg Arg Arg Glu Gln Asp Glu Leu Phe Thr Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Lys Glu
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Arg Phe Asn Gln Ala
305                 310                 315                 320

Leu Thr Gln Thr Gly Arg Leu Ser Ser Ala Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Glu Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415
```

-continued

Lys Ala Val Asn Phe Gly Ile Val Tyr Gly Ile Ser Asp Tyr Gly Leu
            420                 425                 430

Ala Gln Asn Leu Asn Ile Lys Arg Lys Glu Ala Ala Glu Phe Ile Glu
                435                 440                 445

Arg Tyr Phe Ala Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Glu Gln Leu Val Pro
545                 550                 555                 560

Glu Val Met Glu Gln Ala Val Arg Leu Arg Val Pro Leu Lys Val Asp
                565                 570                 575

Tyr His Tyr Gly Pro Thr Trp Tyr Asp Ala Lys
            580                 585

<210> SEQ ID NO 3
<211> LENGTH: 587
<212> TYPE: PRT
<213> ORGANISM: Artificial Sequence
<220> FEATURE:
<223> OTHER INFORMATION: Synthetic construct

<400> SEQUENCE: 3

Glu Glu Glu Gly Lys Pro Leu Ala Glu Met Glu Phe Thr Ile Ala Asp
1               5                   10                  15

Glu Val Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu Arg Gly Arg Phe Phe Leu Arg Thr Glu Thr Ala Leu Ala
        50                  55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Leu Pro Asp Glu Pro Thr Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Glu Asn Glu Gln Asp Glu Leu Leu Thr Glu Leu Glu Gln Pro Leu
            180                 185                 190

Ala Leu Ile Leu Ala Glu Met Glu Phe Thr Gly Val Lys Val Asp Thr
    195                 200                 205

Lys Arg Leu Glu Gln Met Gly Glu Leu Ala Glu Gln Leu Lys Glu
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                    245                 250                 255

Val Leu Lys Lys Thr Lys Thr Gly Tyr Ser Thr Ser Ala Asp Val Leu
                    260                 265                 270

Glu Lys Leu Ala Pro His Arg Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Arg Phe Asn Gln Ala
305                 310                 315                 320

Leu Thr Gln Thr Gly Arg Leu Ser Ser Ala Glu Pro Asn Leu Gln Asn
                    325                 330                 335

Ile Pro Ile Arg Leu Glu Glu Gly Arg Lys Ile Arg Gln Ala Phe Val
                    340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
            370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                    405                 410                 415

Lys Ala Val Asn Phe Gly Ile Val Tyr Gly Ile Ser Asp Tyr Gly Leu
                    420                 425                 430

Ala Gln Asn Leu Asn Ile Thr Arg Lys Glu Ala Ala Glu Phe Ile Glu
            435                 440                 445

Arg Tyr Phe Gln Ser Phe Pro Gly Val Lys Arg Tyr Met Glu Asp Ile
            450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                    485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Leu Gln Val His Asp Glu Leu Ile
            530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
                    565                 570                 575

Tyr Arg Tyr Gly Pro Thr Trp Tyr Asp Ala Lys
            580                 585

<210> SEQ ID NO 4
<211> LENGTH: 587

```
<212> TYPE: PRT
<213> ORGANISM: Artificial Sequence
<220> FEATURE:
<223> OTHER INFORMATION: Synthetic construct

<400> SEQUENCE: 4

Ala Glu Glu Lys Pro Leu Glu Asp Ile Glu Phe Asp Ile Ala Asp
  1               5                  10                  15

Glu Val Thr Glu Glu Met Leu Ala Asp Lys Ala Ala Leu Val Val Glu
                 20                  25                  30

Val Gln Glu Asp Asn Tyr His Asp Ala Pro Ile Val Gly Phe Ala Ile
             35                  40                  45

Val Asn Glu His Gly Arg Phe Phe Ile Arg Thr Glu Thr Ala Leu Ala
 50                  55                  60

Ser Pro Gln Phe Lys Ala Trp Leu Ala Asp Glu Thr Lys Lys Ser
 65                  70                  75                  80

Val Phe Asp Ala Lys Arg Ala Ile Val Ala Leu Lys Trp Lys Gly Ile
                 85                  90                  95

Glu Leu Arg Gly Val Asp Phe Asp Leu Leu Ala Ala Tyr Leu Leu
            100                 105                 110

Asn Pro Ala Gln Thr Ala Asp Asp Val Ala Ala Val Ala Lys Met Lys
            115                 120                 125

Gln Tyr His Ala Val Arg Ser Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Lys Asn Glu Gln Asp Glu Leu Leu Thr Glu Leu Glu Leu Pro Leu
                180                 185                 190

Ala Leu Ile Leu Ala Glu Met Glu Phe Thr Gly Val Lys Val Asp Thr
            195                 200                 205

Lys Arg Leu Glu Gln Met Gly Glu Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asn Asp Asn Leu Ile Glu
    370                 375                 380
```

```
Ala Phe Arg Arg Asp Met Asp Ile His Thr Lys Thr Ala Met Asp Val
385                 390                 395                 400

Phe His Val Ser Glu Asp Glu Val Thr Ser Asn Met Arg Arg Gln Ala
            405                 410                 415

Lys Ala Val Asn Phe Gly Ile Val Tyr Gly Ile Ser Asp Tyr Gly Leu
            420                 425                 430

Ser Gln Asn Leu Gly Ile Thr Arg Lys Glu Ala Ala Glu Phe Ile Glu
            435                 440                 445

Arg Tyr Phe Glu Ser Phe Pro Gly Val Lys Tyr Met Glu Asp Ile
450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Met Ala Ala Arg Leu Lys Glu
            515                 520                 525

Glu Arg Leu Gln Ala Arg Leu Leu Leu Gln Val His Asp Glu Leu Ile
530                 535                 540

Phe Glu Ala Pro Lys Glu Glu Ile Glu Arg Leu Cys Lys Leu Val Pro
545                 550                 555                 560

Glu Val Met Glu His Ala Val Glu Leu Arg Val Pro Leu Lys Val Asp
                565                 570                 575

Tyr His Tyr Gly Pro Thr Trp Tyr Asp Ala Lys
                580                 585

<210> SEQ ID NO 5
<211> LENGTH: 587
<212> TYPE: PRT
<213> ORGANISM: Artificial Sequence
<220> FEATURE:
<223> OTHER INFORMATION: Synthetic construct

<400> SEQUENCE: 5

Thr Glu Glu Val Glu Leu Glu Asp Ile Asn Val Lys Thr Val Thr
1               5                   10                  15

Glu Val Thr Ser Glu Met Leu Thr Asp Pro Ser Ala Leu Val Val Glu
            20                  25                  30

Gln Leu Gly Asp Asn Tyr His Glu Ala Asp Ile Ile Gly Phe Ala Ile
            35                  40                  45

Val Asn Glu Asn Gly Ala Phe Phe Ile Pro Lys Glu Thr Ala Leu Gln
50                  55                  60

Ser Glu Ala Phe Lys Glu Trp Val Glu Asp Thr Lys Lys Lys Trp
65                  70                  75                  80

Val Phe Asp Ser Lys Arg Ala Val Val Ala Leu Arg Trp His Gly Ile
                85                  90                  95

Glu Leu Lys Gly Val Asp Phe Asp Val Leu Leu Ala Ser Tyr Ile Ile
            100                 105                 110

Asn Pro Ser Asn Ser Tyr Asp Asp Val Ala Ser Val Ala Lys Glu Tyr
            115                 120                 125

Gly Leu Asn Ile Val Ser Ser Asp Glu Ala Val Tyr Gly Lys Gly Ala
            130                 135                 140

Lys Arg Ala Val Pro Ala Glu Asp Glu Leu Ala Glu His Leu Gly Arg
145                 150                 155                 160
```

```
Lys Ala Ala Ala Ile Ser Ala Leu Arg Asp Lys Leu Leu Gln Ala Leu
                165                 170                 175
Glu Glu Asn Asp Gln Tyr Glu Leu Phe Glu Asp Leu Glu Met Pro Leu
            180                 185                 190
Ala Leu Ile Leu Gly Glu Met Glu Ser Thr Gly Val Lys Val Asp Val
        195                 200                 205
Glu Arg Leu Lys Arg Met Gly Glu Glu Leu Thr Glu Lys Leu Lys Glu
    210                 215                 220
Tyr Glu Glu Lys Ile His Glu Leu Ala Gly Glu Pro Phe Asn Ile Asn
225                 230                 235                 240
Ser Pro Lys Gln Leu Gly Val Ile Leu Phe Glu Lys Leu Gly Leu Pro
                245                 250                 255
Val Ile Lys Lys Thr Lys Thr Gly Tyr Ser Thr Ser Ala Asp Val Leu
            260                 265                 270
Glu Lys Leu Ala Asp Lys His Glu Ile Ile Arg Tyr Ile Leu His Tyr
        275                 280                 285
Arg Gln Ile Gly Lys Leu Gln Ser Thr Tyr Ile Glu Gly Leu Leu Lys
    290                 295                 300
Val Thr Arg Lys Asp Thr His Lys Val His Thr Arg Phe Asn Gln Ala
305                 310                 315                 320
Leu Thr Gln Thr Gly Arg Leu Ser Ser Thr Asp Pro Asn Leu Gln Asn
                325                 330                 335
Ile Pro Ile Arg Leu Glu Glu Gly Arg Lys Ile Arg Gln Ala Phe Val
            340                 345                 350
Pro Ser Glu Glu Gly Trp Leu Ile Phe Ala Ala Asp Tyr Ser Gln Ile
        355                 360                 365
Glu Leu Arg Val Leu Ala His Ile Ser Lys Asp Glu Asn Leu Ile Glu
    370                 375                 380
Ala Phe Thr His Asp Met Asp Ile His Thr Lys Thr Ala Met Asp Val
385                 390                 395                 400
Phe His Val Ser Glu Asp Glu Val Thr Ser Ala Met Arg Arg Gln Ala
                405                 410                 415
Lys Ala Val Asn Phe Gly Ile Val Tyr Gly Ile Ser Asp Tyr Gly Leu
            420                 425                 430
Ser Gln Asn Leu Gly Ile Thr Arg Lys Glu Ala Gly Ala Phe Ile Glu
        435                 440                 445
Arg Tyr Leu Glu Ser Phe Pro Gly Val Lys Ala Tyr Met Glu Asp Ile
    450                 455                 460
Val Gln Glu Ala Lys Gln Lys Gly Tyr Val Thr Thr Leu Leu His Arg
465                 470                 475                 480
Arg Arg Tyr Ile Pro Glu Ile Thr Ser Arg Asn Phe Asn Ile Arg Ser
                485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Met Ala Ala Arg Leu Lys Glu
        515                 520                 525
Glu Asn Leu Gln Ala Arg Leu Leu Leu Gln Val His Asp Glu Leu Ile
    530                 535                 540
Phe Glu Ala Pro Lys Glu Ile Glu Ile Leu Glu Lys Ile Val Pro
545                 550                 555                 560
Glu Val Met Glu His Ala Leu Glu Leu Asp Val Pro Leu Lys Val Asp
                565                 570                 575
Tyr Ala Ser Gly Pro Ser Trp Tyr Asp Ala Lys
```

-continued

```
            580                 585

<210> SEQ ID NO 6
<211> LENGTH: 587
<212> TYPE: PRT
<213> ORGANISM: Artificial Sequence
<220> FEATURE:
<223> OTHER INFORMATION: Synthetic construct

<400> SEQUENCE: 6

Glu Glu Glu Glu Val Pro Leu Glu Glu Ile Glu Phe Ala Ile Ala Asp
1               5                   10                  15

Glu Val Thr Glu Glu Met Leu Ala Asp Lys Ala Ala Leu Val Val Glu
            20                  25                  30

Val Leu Glu Glu Asn Tyr His Asp Ala Pro Ile Val Gly Phe Ala Leu
        35                  40                  45

Val Asn Glu His Gly Arg Phe Phe Ile Arg Pro Glu Thr Ala Leu Ala
    50                  55                  60

Ser Ser Gln Phe Lys Ala Trp Leu Glu Asp Glu Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
            100                 105                 110

Asn Pro Ala Gln Ser Ala Glu Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Val Leu Ala Glu His Leu Val Arg
145                 150                 155                 160

Lys Ala Ala Ile Trp Ala Leu Glu Glu Pro Phe Ile Asp Glu Leu
                165                 170                 175

Arg Glu Asn Glu Gln Asp Glu Leu Phe Thr Asp Leu Glu Gln Pro Leu
            180                 185                 190

Ala Leu Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Lys Glu
    210                 215                 220

Ile Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
```

```
                355                 360                 365
Glu Leu Arg Val Leu Ala His Ile Ala Asp Asp Glu Asn Leu Ile Glu
370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ser Gln Asn Leu Asn Ile Thr Arg Lys Glu Ala Ala Glu Phe Ile Glu
                435                 440                 445

Arg Tyr Phe Ala Ser Phe Pro Gly Val Lys Gln Tyr Met Glu Asn Ile
                450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Leu Ala Ala Arg Leu Lys Glu
                515                 520                 525

Glu Arg Leu Gln Ala Arg Leu Leu Leu Gln Val His Asp Glu Leu Ile
                530                 535                 540

Leu Glu Ala Pro Lys Glu Glu Ile Glu Arg Leu Cys Lys Leu Val Pro
545                 550                 555                 560

Glu Val Met Glu Asn Ala Val Thr Leu Arg Val Pro Leu Lys Val Asp
                565                 570                 575

Tyr His Tyr Gly Pro Thr Trp Tyr Asp Ala Lys
                580                 585

<210> SEQ ID NO 7
<211> LENGTH: 587
<212> TYPE: PRT
<213> ORGANISM: Artificial Sequence
<220> FEATURE:
<223> OTHER INFORMATION: Synthetic construct

<400> SEQUENCE: 7

Ala Glu Glu Glu Ala Pro Leu Glu Asp Ile Glu Phe Asp Ile Ala Asp
1               5                   10                  15

Glu Val Thr Glu Glu Met Leu Ala Asp Lys Ala Ala Leu Val Val Glu
                20                  25                  30

Val Gln Glu Asp Asn Tyr His Asp Ala Pro Ile Val Gly Phe Ala Ile
                35                  40                  45

Val Asn Glu Arg Gly Arg Phe Phe Ile Arg Thr Glu Thr Ala Leu Ala
50                  55                  60

Ser Glu Ala Phe Lys Ala Trp Leu Ala Asp Glu Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
                100                 105                 110

Asn Pro Ala Gln Thr Ala Asp Asp Val Ala Val Ala Lys Met Lys
                115                 120                 125

Gln Tyr His Ala Val Arg Ser Asp Glu Ala Val Tyr Gly Lys Gly Ala
```

```
            130                 135                 140
Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Lys Asn Glu Gln Asp Glu Leu Phe Thr Glu Leu Glu Leu Pro Leu
                180                 185                 190

Ala Leu Ile Leu Ala Glu Met Glu Phe Thr Gly Val Lys Val Asp Thr
            195                 200                 205

Lys Arg Leu Glu Gln Met Gly Glu Glu Leu Ala Glu Gln Leu Lys Glu
            210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
                260                 265                 270

Glu Lys Leu Ala Pro His Arg Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
                325                 330                 335

Ile Pro Ile Arg Leu Glu Glu Gly Arg Lys Ile Arg Gln Ala Phe Val
                340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asn Asp Asp Asn Leu Ile Glu
            370                 375                 380

Ala Phe Arg Arg Asp Met Asp Ile His Thr Lys Thr Ala Met Asp Val
385                 390                 395                 400

Phe His Val Ser Glu Asp Glu Val Thr Ser Asn Met Arg Arg Gln Ala
                405                 410                 415

Lys Ala Val Asn Phe Gly Ile Val Tyr Gly Ile Ser Asp Tyr Gly Leu
                420                 425                 430

Ser Gln Asn Leu Gly Ile Thr Arg Lys Glu Ala Ala Glu Phe Ile Glu
            435                 440                 445

Arg Tyr Phe Gln Ser Phe Pro Gly Val Lys Glu Tyr Met Glu Asp Ile
            450                 455                 460

Val Gln Glu Ala Lys Gln Lys Gly Tyr Val Thr Thr Leu Leu His Arg
465                 470                 475                 480

Arg Arg Phe Leu Pro Glu Ile Thr Ser Arg Asn Phe Asn Leu Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Met Ala Ala Arg Leu Lys Glu
            515                 520                 525

Glu Arg Leu Gln Ala Arg Leu Leu Leu Gln Val His Asp Glu Leu Ile
            530                 535                 540

Phe Glu Ala Pro Lys Glu Glu Ile Glu Arg Leu Glu Lys Leu Val Pro
545                 550                 555                 560
```

```
Glu Val Met Glu His Ala Val Glu Leu Arg Val Pro Leu Lys Val Asp
            565                 570                 575

Tyr Arg Tyr Gly Pro Thr Trp Tyr Asp Ala Lys
            580                 585

<210> SEQ ID NO 8
<211> LENGTH: 587
<212> TYPE: PRT
<213> ORGANISM: Artificial Sequence
<220> FEATURE:
<223> OTHER INFORMATION: Synthetic construct

<400> SEQUENCE: 8

Ala Glu Glu Glu Lys Pro Leu Glu Glu Met Glu Phe Ala Ile Ala Asp
1               5                   10                  15

Glu Val Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
50                  55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Asp Asp Val Ala Val Ala Lys Met Lys
        115                 120                 125

Gln Tyr Glu Ala Val Arg Ser Asp Glu Ala Val Tyr Gly Lys Gly Ala
130                 135                 140

Lys Arg Ala Val Pro Asp Glu Pro Val Leu Ala Glu His Leu Val Arg
145                 150                 155                 160

Lys Ala Ala Ala Ile Arg Ala Leu Glu Arg Pro Phe Leu Asp Glu Leu
                165                 170                 175

Arg Asn Asn Glu Gln Asp Glu Leu Leu Thr Glu Leu Glu Gln Pro Leu
            180                 185                 190

Ala Ala Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
290                 295                 300

Val Val His Pro Asp Thr Lys Lys Val His Thr Arg Phe Asn Gln Ala
305                 310                 315                 320

Leu Thr Gln Thr Gly Arg Leu Ser Ser Thr Glu Pro Asn Leu Gln Asn
                325                 330                 335
```

Ile Pro Ile Arg Leu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
            370                 375                 380

Ala Phe Arg Arg Asp Leu Asp Ile His Thr Lys Thr Ala Met Asp Ile
385                 390                 395                 400

Phe His Val Ser Glu Asp Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ser Gln Asn Leu Asn Ile Thr Arg Lys Glu Ala Ala Glu Phe Ile Glu
            435                 440                 445

Arg Tyr Phe Glu Ser Phe Pro Gly Val Lys Arg Tyr Met Glu Asn Ile
            450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Lys Arg Leu Lys Glu
            515                 520                 525

Glu Arg Leu Gln Ala Arg Leu Leu Leu Gln Val His Asp Glu Leu Ile
            530                 535                 540

Leu Glu Ala Pro Lys Glu Glu Ile Glu Arg Leu Glu Lys Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 9
<211> LENGTH: 587
<212> TYPE: PRT
<213> ORGANISM: Artificial Sequence
<220> FEATURE:
<223> OTHER INFORMATION: Synthetic construct

<400> SEQUENCE: 9

Ala Glu Glu Glu Lys Pro Leu Ala Glu Met Glu Phe Ala Ile Ala Asp
1               5                   10                  15

Ser Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
50                  55                  60

Asp Pro Gln Phe Leu Ala Trp Leu Gly Asp Glu Thr Lys Lys Lys Ser
65                  70                  75                  80

Met Phe Asp Ser Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

-continued

```
Asn Pro Ala Gln Ala Ala Gly Asp Val Ala Ala Val Ala Lys Met Lys
        115                 120                 125
Gln Tyr Glu Ala Val Arg Ser Asp Glu Ala Val Tyr Gly Lys Gly Ala
130                 135                 140
Lys Arg Ser Val Pro Asp Glu Pro Thr Leu Ala Glu His Leu Val Arg
145                 150                 155                 160
Lys Ala Ala Ile Trp Ala Leu Glu Gln Pro Phe Met Asp Glu Leu
            165                 170                 175
Arg Arg Asn Glu Gln Asp Arg Leu Leu Thr Glu Leu Glu Gln Pro Leu
            180                 185                 190
Ala Ser Ile Leu Ala Glu Met Glu Phe Thr Gly Val Lys Val Asp Thr
        195                 200                 205
Lys Arg Leu Glu Gln Met Gly Glu Glu Leu Thr Glu Gln Leu Arg Ala
210                 215                 220
Val Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
            245                 250                 255
Val Leu Lys Lys Thr Lys Thr Gly Tyr Ser Thr Ser Ala Asp Val Leu
        260                 265                 270
Glu Lys Leu Ala Pro His His Glu Ile Val Glu Asn Ile Leu His Tyr
        275                 280                 285
Arg Gln Leu Gly Lys Leu Gln Ser Thr Tyr Ile Glu Gly Leu Leu Lys
        290                 295                 300
Val Val His Pro Asp Thr Gly Lys Val His Thr Met Phe Asn Gln Ala
305                 310                 315                 320
Leu Thr Gln Thr Gly Arg Leu Ser Ser Thr Glu Pro Asn Leu Gln Asn
            325                 330                 335
Ile Pro Ile Arg Leu Glu Glu Gly Arg Lys Ile Arg Gln Ala Phe Val
            340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Asp Asp Asn Leu Ile Glu
        370                 375                 380
Ala Phe Arg Arg Asp Leu Asp Ile His Thr Lys Thr Ala Met Asp Ile
385                 390                 395                 400
Phe His Val Ser Glu Glu Val Thr Ala Asn Met Arg Arg Gln Ala
            405                 410                 415
Lys Ala Val Asn Phe Gly Ile Val Tyr Gly Ile Ser Asp Tyr Gly Leu
            420                 425                 430
Ala Gln Asn Leu Asn Ile Thr Arg Lys Glu Ala Ala Glu Phe Ile Glu
        435                 440                 445
Arg Tyr Phe Ala Ser Phe Pro Gly Val Lys Gln Tyr Met Glu Asn Ile
    450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
            485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Leu Ala Ala Arg Leu Lys Glu
        515                 520                 525
```

```
Glu Arg Leu Gln Ala Arg Leu Leu Gln Val His Asp Glu Leu Ile
530                 535                 540
Leu Glu Ala Pro Lys Glu Ile Glu Arg Leu Cys Arg Leu Val Pro
545                 550                 555                 560
Glu Val Met Glu Gln Ala Val Thr Leu Arg Val Pro Leu Lys Val Asp
                565                 570                 575
Tyr His Tyr Gly Pro Thr Trp Tyr Asp Ala Lys
            580                 585

<210> SEQ ID NO 10
<211> LENGTH: 587
<212> TYPE: PRT
<213> ORGANISM: Artificial Sequence
<220> FEATURE:
<223> OTHER INFORMATION: Synthetic construct

<400> SEQUENCE: 10

Ala Glu Asp Glu Thr Pro Leu Met Glu Met Glu Phe Val Ile Ala Asp
1               5                   10                  15
Gly Ile Thr Asp Glu Met Leu Ala Asp Lys Ala Ala Leu Val Val Glu
                20                  25                  30
Val Gln Glu Glu Asn Tyr His Asp Ala Pro Ile Val Gly Ile Ala Leu
            35                  40                  45
Val Asn Glu His Gly Arg Phe Phe Leu Arg Ala Glu Met Ala Leu Ala
50                  55                  60
Asp Pro Gln Phe Val Ala Trp Leu Ala Asp Glu Thr Lys Lys Lys Ser
65                  70                  75                  80
Met Phe Asp Ala Lys Arg Ala Ala Val Ala Leu Lys Trp Lys Gly Ile
                85                  90                  95
Glu Leu Arg Gly Val Asp Phe Asp Leu Leu Ala Ala Tyr Leu Leu
                100                 105                 110
Asn Pro Ala Gln Thr Asp Glu Asp Val Ala Val Ala Lys Met Lys
            115                 120                 125
Gln Tyr Glu Ala Val Arg Pro Asp Glu Ala Val Tyr Gly Lys Gly Ala
    130                 135                 140
Lys Arg Pro Leu Pro Asp Glu Pro Ala Leu Ala Glu His Leu Val Arg
145                 150                 155                 160
Lys Ala Ala Ala Ile Trp Ala Leu Glu Arg Pro Phe Leu Asp Glu Leu
                165                 170                 175
Arg Ser Asn Glu Gln Asp Glu Leu Leu Ile Lys Leu Glu Leu Pro Leu
            180                 185                 190
Ala Thr Ile Leu Ala Glu Met Glu Phe Thr Gly Val Lys Val Asp Thr
        195                 200                 205
Lys Arg Leu Glu Gln Met Gly Ser Glu Leu Ala Glu Gln Leu Arg Ala
    210                 215                 220
Val Glu Gln Arg Ile Tyr Glu Leu Ala Gly Gln Glu Phe Asn Ile Asn
225                 230                 235                 240
Ser Pro Lys Gln Leu Gly Ile Ile Leu Phe Glu Lys Leu Gln Leu Pro
                245                 250                 255
Val Leu Lys Lys Thr Lys Thr Gly Tyr Ser Thr Ser Ala Asp Val Leu
            260                 265                 270
Glu Lys Leu Ala Pro His His Glu Ile Val Glu Asn Ile Leu His Tyr
        275                 280                 285
Arg Gln Leu Gly Lys Leu Gln Ser Thr Tyr Ile Glu Gly Leu Leu Lys
    290                 295                 300
```

```
Val Val His Pro Asp Thr Gly Lys Val His Thr Arg Phe Asn Gln Ala
305                 310                 315                 320

Leu Thr Gln Thr Gly Arg Leu Ser Ser Ala Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
            370                 375                 380

Ala Phe Arg Arg Asp Leu Asp Ile His Thr Lys Thr Ala Met Asp Ile
385                 390                 395                 400

Phe His Val Ser Glu Glu Val Thr Ala Arg Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
            435                 440                 445

Arg Tyr Phe Glu Ser Phe Pro Gly Val Lys Arg Tyr Met Glu Thr Ile
450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Leu Gln Val His Asp Glu Leu Ile
            530                 535                 540

Leu Glu Ala Pro Lys Glu Glu Met Glu Arg Leu Cys Gln Leu Val Pro
545                 550                 555                 560

Glu Val Met Glu Gln Ala Val Ala Leu Arg Val Pro Leu Lys Val Asp
                565                 570                 575

Tyr His Tyr Gly Pro Thr Trp Tyr Asp Ala Lys
            580                 585

<210> SEQ ID NO 11
<211> LENGTH: 587
<212> TYPE: PRT
<213> ORGANISM: Artificial Sequence
<220> FEATURE:
<223> OTHER INFORMATION: Synthetic construct

<400> SEQUENCE: 11

Ala Glu Glu Glu Lys Pro Leu Ala Glu Met Glu Phe Thr Ile Ala Asp
1               5                   10                  15

Glu Val Thr Glu Glu Met Leu Ala Asp Lys Ala Ala Leu Val Val Glu
            20                  25                  30

Val Leu Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Ser Gln Phe Leu Ala Trp Leu Glu Asp Glu Thr Lys Lys Lys Ser
65                  70                  75                  80
```

-continued

```
Met Phe Asp Ala Lys Arg Ala Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Ala Ala Gly Asp Val Ala Ala Val Ala Lys Met Lys
            115                 120                 125

Gln Tyr Glu Ala Val Arg Ser Asp Glu Ala Val Tyr Gly Lys Gly Ala
            130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Ile Asp Glu Leu
                165                 170                 175

Arg Arg Asn Glu Gln Asp Arg Leu Leu Thr Asp Leu Glu Gln Pro Leu
            180                 185                 190

Ser Ser Ile Leu Ala Glu Met Glu Phe Thr Gly Val Lys Val Asp Thr
            195                 200                 205

Lys Arg Leu Glu Gln Met Gly Glu Glu Leu Ala Glu Gln Leu Arg Ala
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Ile Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asn Asp Asp Asn Leu Ile Glu
            370                 375                 380

Ala Phe Arg Arg Asp Leu Asp Ile His Thr Lys Thr Ala Met Asp Ile
385                 390                 395                 400

Phe His Val Ser Glu Asp Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
            435                 440                 445

Arg Tyr Phe Glu Ser Phe Pro Gly Val Lys Gln Tyr Met Glu Asn Ile
            450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
```

```
                500             505             510
Asp Ile Ile Lys Lys Ala Met Ile Asp Leu Ala Ala Arg Leu Lys Glu
            515                 520             525

Glu Arg Leu Gln Ala Arg Leu Leu Gln Val His Asp Glu Leu Ile
        530                 535             540

Leu Glu Ala Pro Lys Glu Ile Glu Arg Leu Cys Gln Leu Val Pro
545             550             555             560

Glu Val Met Glu Gln Ala Val Thr Leu Arg Val Pro Leu Lys Val Asp
                565             570             575

Tyr His Tyr Gly Pro Thr Trp Tyr Asp Ala Lys
            580             585

<210> SEQ ID NO 12
<211> LENGTH: 587
<212> TYPE: PRT
<213> ORGANISM: Artificial Sequence
<220> FEATURE:
<223> OTHER INFORMATION: Synthetic construct

<400> SEQUENCE: 12

Ala Glu Glu Lys Pro Leu Ala Glu Met Glu Phe Ala Ile Ala Asp
1               5                   10                  15

Ser Val Thr Glu Glu Met Leu Ala Asp Lys Ala Ala Leu Val Val Glu
                20                  25                  30

Val Val Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
50                  55                  60

Asp Pro Gln Phe Leu Ala Trp Leu Gly Asp Glu Thr Lys Lys Ser
65                  70                  75                  80

Met Phe Asp Ser Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Arg Asn Glu Gln Asp Arg Leu Leu Thr Glu Leu Glu Gln Pro Leu
            180                 185                 190

Ala Ser Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Arg Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
```

```
            275                 280                 285
Arg Gln Leu Gly Lys Leu Gln Ser Thr Tyr Ile Glu Gly Leu Leu Lys
290                 295                 300

Val Val His Pro Asp Thr Gly Lys Val His Thr Met Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
                340                 345                 350

Pro Ser Glu Pro Asp Trp Leu Ile Phe Ala Ala Asp Tyr Ser Gln Ile
                355                 360                 365

Glu Leu Arg Val Leu Ala His Ile Ala Asp Asp Asn Leu Ile Glu
370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Thr Arg Lys Glu Ala Ala Glu Phe Ile Glu
                435                 440                 445

Arg Tyr Phe Ala Ser Phe Pro Gly Val Lys Gln Tyr Met Glu Asn Ile
                450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Leu Ala Ala Arg Leu Lys Glu
                515                 520                 525

Glu Arg Leu Gln Ala Arg Leu Leu Leu Gln Val His Asp Glu Leu Ile
530                 535                 540

Leu Glu Ala Pro Lys Glu Glu Ile Glu Arg Leu Cys Arg Leu Val Pro
545                 550                 555                 560

Glu Val Met Glu Gln Ala Val Thr Leu Arg Val Pro Leu Lys Val Asp
                565                 570                 575

Tyr His Tyr Gly Pro Thr Trp Tyr Asp Ala Lys
                580                 585

<210> SEQ ID NO 13
<211> LENGTH: 587
<212> TYPE: PRT
<213> ORGANISM: Artificial Sequence
<220> FEATURE:
<223> OTHER INFORMATION: Synthetic construct

<400> SEQUENCE: 13

Ser Glu Glu Glu Lys Pro Leu Ala Lys Met Ala Phe Thr Leu Ala Asp
1               5                   10                  15

Glu Val Thr Glu Glu Met Leu Ala Asp Lys Ala Ala Leu Val Val Glu
                20                  25                  30

Val Val Glu Glu Asn Tyr His Asp Ala Pro Ile Val Gly Ile Ala Val
                35                  40                  45

Val Asn Glu His Gly Arg Phe Phe Leu Arg Pro Glu Thr Ala Leu Ala
```

```
                  50                  55                  60
Ser Pro Gln Phe Val Ala Trp Leu Gly Asp Glu Thr Lys Lys Ser
 65                  70                  75                  80

Met Phe Asp Ser Lys Arg Ala Ile Val Ala Leu Lys Trp Lys Gly Ile
                     85                  90                  95

Glu Leu Cys Gly Val Ser Phe Asp Leu Leu Ala Ala Tyr Leu Leu
                100                 105                 110

Asp Pro Ala Gln Gly Val Asp Val Ala Ala Ala Lys Met Lys
                115                 120                 125

Gln Tyr Glu Ala Val Arg Pro Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Arg Leu Leu Thr Glu Leu Glu Gln Pro Leu
                180                 185                 190

Ser Ser Ile Leu Ala Glu Met Glu Phe Ala Gly Val Lys Val Asp Thr
        195                 200                 205

Lys Arg Leu Glu Gln Met Gly Glu Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
                260                 265                 270

Glu Lys Leu Ala Pro Tyr His Glu Ile Val Glu Asn Ile Leu His Tyr
        275                 280                 285

Arg Gln Leu Gly Lys Leu Gln Ser Thr Tyr Ile Glu Gly Leu Leu Lys
        290                 295                 300

Val Val His Pro Asp Thr Lys Lys Val His Thr Arg Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
                340                 345                 350

Pro Ser Glu Ser Asp Trp Leu Ile Phe Ala Ala Asp Tyr Ser Gln Ile
            355                 360                 365

Glu Leu Arg Val Leu Ala His Ile Ala Glu Asp Asp Asn Leu Met Glu
        370                 375                 380

Ala Phe Arg Arg Asp Leu Asp Ile His Thr Lys Thr Ala Met Asp Ile
385                 390                 395                 400

Phe Gln Val Ser Glu Asp Glu Val Thr Pro Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Ser Arg Lys Glu Ala Ala Glu Phe Ile Glu
        435                 440                 445

Arg Tyr Phe Glu Ser Phe Pro Gly Val Lys Arg Tyr Met Glu Asn Ile
        450                 455                 460

Val Gln Glu Ala Lys Gln Lys Gly Tyr Val Thr Thr Leu Leu His Arg
465                 470                 475                 480
```

```
Arg Arg Tyr Leu Pro Asp Ile Thr Ser Arg Asn Phe Asn Val Arg Ser
                485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Asn Ala Arg Leu Lys Glu
        515                 520                 525

Glu Arg Leu Gln Ala Arg Leu Leu Gln Val His Asp Glu Leu Ile
    530                 535                 540

Leu Glu Ala Pro Lys Glu Glu Met Glu Arg Leu Cys Lys Leu Val Pro
545                 550                 555                 560

Glu Val Met Glu Gln Ala Val Glu Leu Arg Val Pro Leu Lys Val Asp
                565                 570                 575

Tyr His Tyr Gly Ser Thr Trp Tyr Asp Ala Lys
                580                 585

<210> SEQ ID NO 14
<211> LENGTH: 587
<212> TYPE: PRT
<213> ORGANISM: Artificial Sequence
<220> FEATURE:
<223> OTHER INFORMATION: Synthetic construct

<400> SEQUENCE: 14

Ala Glu Glu Lys Pro Leu Ala Glu Met Glu Phe Val Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
        50                  55                  60

Ser Pro Gln Phe Val Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Glu Leu Leu Thr Glu Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Lys Glu
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255
```

Val Leu Lys Lys Thr Lys Thr Gly Tyr Ser Thr Ser Ala Asp Val Leu
        260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
        290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Ala Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 15
<211> LENGTH: 587
<212> TYPE: PRT
<213> ORGANISM: Artificial Sequence
<220> FEATURE:
<223> OTHER INFORMATION: Synthetic construct

<400> SEQUENCE: 15

Ala Glu Glu Glu Lys Pro Leu Ala Glu Met Glu Phe Val Ile Ala Asp
1               5                   10                  15

Gly Ile Thr Glu Glu Met Leu Ala Asp Lys Ala Ala Leu Val Val Glu
            20                  25                  30

```
Val Met Glu Glu Asn Tyr His Asp Ala Pro Ile Val Gly Ile Ala Leu
     35                  40                  45

Val Asn Glu His Gly Arg Phe Phe Leu Arg Pro Glu Thr Ala Leu Ala
 50                  55                  60

Asp Pro Gln Phe Val Ala Trp Leu Ala Asp Glu Thr Lys Lys Lys Ser
 65                  70                  75                  80

Met Phe Asp Ala Lys Arg Ala Ala Val Ala Leu Lys Trp Lys Gly Ile
                 85                  90                  95

Glu Leu Arg Gly Val Ala Phe Asp Leu Leu Leu Ala Ala Tyr Leu Leu
                100                 105                 110

Asn Pro Ala Gln Asp Ala Gly Asp Val Ala Ala Val Ala Lys Met Lys
                115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Glu Leu Leu Ile Lys Leu Glu Gln Pro Leu
                180                 185                 190

Ala Thr Ile Leu Ala Glu Met Glu Phe Thr Gly Val Lys Val Asp Thr
    195                 200                 205

Lys Arg Leu Glu Gln Met Gly Glu Glu Leu Ala Glu Gln Leu Gly Ala
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
                260                 265                 270

Glu Lys Leu Ala Pro His His Glu Ile Val Glu Asn Ile Leu His Tyr
    275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
                340                 345                 350

Pro Ser Glu Pro Asp Trp Leu Ile Phe Ala Ala Asp Tyr Ser Gln Ile
    355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Thr Arg Lys Glu Ala Ala Glu Phe Ile Glu
    435                 440                 445
```

```
Arg Tyr Phe Ala Ser Phe Pro Gly Val Lys Arg Tyr Met Glu Asn Ile
            450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
                515                 520                 525

Glu Arg Leu Gln Ala Arg Leu Leu Gln Val His Asp Glu Leu Ile
530                 535                 540

Leu Glu Ala Pro Lys Glu Glu Ile Glu Arg Leu Cys Arg Leu Val Pro
545                 550                 555                 560

Glu Val Met Glu Gln Ala Val Thr Leu Arg Val Pro Leu Lys Val Asp
                565                 570                 575

Tyr His Tyr Gly Pro Thr Trp Tyr Asp Ala Lys
                580                 585

<210> SEQ ID NO 16
<211> LENGTH: 587
<212> TYPE: PRT
<213> ORGANISM: Artificial Sequence
<220> FEATURE:
<223> OTHER INFORMATION: Synthetic construct

<400> SEQUENCE: 16

Glu Glu Glu Glu Lys Pro Leu Glu Asp Ile Ser Phe Glu Ile Ala Asp
1               5                   10                  15

Glu Val Thr Glu Asp Met Leu Thr Asp Glu Ser Ala Leu Val Val Glu
                20                  25                  30

Val Leu Glu Glu Asn Tyr His Lys Ala Asp Ile Val Gly Phe Ala Ile
            35                  40                  45

Ala Asn Glu Asn Gly Asn Phe Phe Ile Pro Thr Asp Thr Ala Leu Ala
50                  55                  60

Ser Pro Gln Phe Lys Lys Trp Leu Glu Asp Glu Thr Lys Lys Lys Ser
65                  70                  75                  80

Val Phe Asp Ala Lys Arg Ala Ile Val Ala Leu Lys Trp His Gly Ile
                85                  90                  95

Glu Leu Lys Gly Val Asp Phe Asp Leu Leu Ile Ala Ser Tyr Leu Leu
            100                 105                 110

Asn Pro Ser Glu Ser Ser Asp Phe Ala Ser Val Ala Lys Thr Lys
                115                 120                 125

Gly Tyr Asn Ala Val Gln Ser Asp Glu Ala Val Tyr Gly Lys Gly Ala
130                 135                 140

Lys Arg Ala Val Pro Asp Glu Glu Lys Leu Ala Glu His Leu Ala Arg
145                 150                 155                 160

Lys Ala Ala Ala Ile Ser Ala Leu Lys Glu Thr Phe Ile His Glu Leu
                165                 170                 175

Lys Glu Asn Glu Gln Tyr Glu Leu Leu Thr Glu Leu Glu Met Pro Leu
            180                 185                 190

Ala Leu Ile Leu Ala Asp Met Glu Tyr Thr Gly Val Lys Val Asp Val
                195                 200                 205

Glu Arg Leu Lys Glu Met Gly Glu Glu Leu Thr Glu Arg Leu Lys Glu
210                 215                 220
```

-continued

Ile Glu Gln Lys Ile Tyr Glu Leu Ala Gly Gln Glu Phe Asn Ile Asn
225                 230                 235                 240

Ser Pro Lys Gln Leu Gly Val Ile Leu Phe Glu Lys Leu Gly Leu Pro
            245                 250                 255

Val Ile Lys Lys Thr Lys Thr Gly Tyr Ser Thr Ser Ala Asp Val Leu
        260                 265                 270

Glu Lys Leu Ala Ser His His Glu Ile Ile Arg His Ile Leu His Tyr
    275                 280                 285

Arg Gln Leu Gly Lys Leu Gln Ser Thr Tyr Ile Glu Gly Leu Leu Lys
290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
            325                 330                 335

Ile Pro Ile Arg Leu Glu Glu Gly Arg Lys Ile Arg Gln Ala Phe Val
        340                 345                 350

Pro Ser Glu Pro Gly Trp Val Ile Phe Ala Ala Asp Tyr Ser Gln Ile
    355                 360                 365

Glu Leu Arg Val Leu Ala His Ile Ala Asn Asp Glu Asn Leu Ile Glu
370                 375                 380

Ala Phe Arg His Asp Met Asp Ile His Thr Lys Thr Ala Met Asp Val
385                 390                 395                 400

Phe His Val Ser Glu Asp Glu Val Thr Ser Asn Met Arg Arg Gln Ala
            405                 410                 415

Lys Ala Val Asn Phe Gly Ile Val Tyr Gly Ile Ser Asp Tyr Gly Leu
        420                 425                 430

Ser Gln Asn Leu Gly Ile Thr Arg Lys Glu Ala Gly Glu Phe Ile Glu
    435                 440                 445

Arg Tyr Leu Glu Ser Phe Pro Gly Val Lys Glu Tyr Met Asp Asp Ile
450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
            485                 490                 495

Phe Ala Glu Arg Thr Ala Met Asn Thr Pro Ile Gln Gly Ser Ala Ala
        500                 505                 510

Asp Ile Ile Lys Lys Ala Met Ile Asp Met Ala Asp Arg Leu Lys Glu
    515                 520                 525

Glu Asn Leu Gln Ala Arg Leu Leu Leu Gln Val His Asp Glu Leu Ile
530                 535                 540

Phe Glu Ala Pro Lys Glu Glu Ile Glu Lys Leu Cys Lys Leu Val Pro
545                 550                 555                 560

Glu Val Met Glu Asn Ala Val Glu Leu Lys Val Pro Leu Lys Val Asp
            565                 570                 575

Tyr Ser Tyr Gly Pro Thr Trp Tyr Asp Ala Lys
            580                 585

<210> SEQ ID NO 17
<211> LENGTH: 587
<212> TYPE: PRT
<213> ORGANISM: Artificial Sequence
<220> FEATURE:
<223> OTHER INFORMATION: Synthetic construct

<400> SEQUENCE: 17

-continued

```
Ala Glu Asp Glu Lys Pro Leu Glu Glu Ile Glu Phe Ala Ile Ala Asp
 1               5                  10                  15
Glu Ile Thr Glu Glu Met Leu Ala Asp Lys Ala Ala Leu Val Val Glu
             20                  25                  30
Val Leu Glu Glu Asn Tyr His Asp Ala Pro Ile Val Gly Phe Ala Ile
         35                  40                  45
Val Asn Glu His Gly Arg Phe Phe Ile Arg Pro Glu Thr Ala Leu Ala
 50                  55                  60
Ser Ser Gln Phe Lys Ala Trp Leu Glu Asp Thr Lys Lys Lys Ser
 65                  70                  75                  80
Met Phe Asp Ala Lys Arg Ala Ala Val Ala Leu Lys Trp Lys Gly Ile
                 85                  90                  95
Glu Leu Arg Gly Val Ala Phe Asp Leu Leu Ala Ala Tyr Leu Leu
             100                 105                 110
Asn Pro Ala Gln Ser Ala Gly Asp Val Ala Ala Val Ala Lys Met Lys
         115                 120                 125
Gln Tyr Glu Ala Val Arg Ser Asp Glu Ala Val Tyr Gly Lys Gly Ala
130                 135                 140
Lys Arg Ala Val Pro Asp Glu Pro Thr Leu Ala Glu His Leu Val Arg
145                 150                 155                 160
Lys Ala Ala Ile Trp Ala Leu Glu Gln Pro Phe Leu Asp Glu Leu
                 165                 170                 175
Arg Glu Asn Glu Gln Asp Glu Leu Leu Thr Lys Leu Glu Gln Pro Leu
             180                 185                 190
Ala Leu Ile Leu Ala Glu Met Glu Phe Thr Gly Val Lys Val Asp Thr
         195                 200                 205
Lys Arg Leu Glu Gln Met Gly Glu Leu Ala Glu Gln Leu Lys Glu
210                 215                 220
Ile Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
                 245                 250                 255
Val Leu Lys Lys Thr Lys Thr Gly Tyr Ser Thr Ser Ala Asp Val Leu
             260                 265                 270
Glu Lys Leu Ala Pro His His Glu Ile Val Glu Asn Ile Leu His Tyr
         275                 280                 285
Arg Gln Leu Gly Lys Leu Gln Ser Thr Tyr Ile Glu Gly Leu Leu Lys
290                 295                 300
Val Val Arg Pro Asp Thr Gly Lys Val His Thr Met Phe Asn Gln Ala
305                 310                 315                 320
Leu Thr Gln Thr Gly Arg Leu Ser Ser Thr Glu Pro Asn Leu Gln Asn
                 325                 330                 335
Ile Pro Ile Arg Leu Glu Glu Gly Arg Lys Ile Arg Gln Ala Phe Val
             340                 345                 350
Pro Ser Glu Pro Asp Trp Leu Ile Phe Ala Ala Asp Tyr Ser Gln Ile
         355                 360                 365
Glu Leu Arg Val Leu Ala His Ile Ala Asp Asp Asn Leu Ile Glu
370                 375                 380
Ala Phe Arg Arg Asp Leu Asp Ile His Thr Lys Thr Ala Met Asp Ile
385                 390                 395                 400
Phe His Val Ser Glu Glu Glu Val Thr Ala Asn Met Arg Arg Gln Ala
                 405                 410                 415
Lys Ala Val Asn Phe Gly Ile Val Tyr Gly Ile Ser Asp Tyr Gly Leu
```

```
                    420                 425                 430
Ser Gln Asn Leu Asn Ile Thr Arg Lys Glu Ala Ala Glu Phe Ile Glu
                435                 440                 445

Arg Tyr Phe Ala Ser Phe Pro Gly Val Lys Arg Tyr Met Glu Glu Ile
            450                 455                 460

Val Gln Glu Ala Lys Gln Lys Gly Tyr Val Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 18
<211> LENGTH: 587
<212> TYPE: PRT
<213> ORGANISM: Artificial Sequence
<220> FEATURE:
<223> OTHER INFORMATION: Synthetic construct

<400> SEQUENCE: 18

Ala Glu Glu Glu Lys Pro Leu Ala Asp Met Glu Phe Ala Ile Ala Asp
1               5                   10                  15

Glu Val Thr Glu Glu Met Leu Ala Asp Lys Ala Ala Leu Val Val Glu
                20                  25                  30

Val Met Glu Asp Asn Tyr His Asp Ala Pro Ile Val Gly Phe Ala Asn
            35                  40                  45

Val Asn Glu His Gly Arg Phe Phe Leu Arg Ala Glu Leu Ala Leu Ala
        50                  55                  60

Asp Ser Gln Phe Leu Ala Trp Leu Glu Asp Glu Thr Lys Lys Lys Ser
65                  70                  75                  80

Met Phe Asp Arg Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Asp Asp Val Ala Ala Val Ala Lys Met Lys
        115                 120                 125

Gln Tyr Glu Ala Val Arg Pro Asp Glu Ala Val Tyr Gly Lys Gly Ala
    130                 135                 140

Lys Arg Ser Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Arg Leu Leu Thr Glu Leu Glu Gln Pro Leu
            180                 185                 190

Ala Thr Ile Leu Ala Glu Met Glu Phe Thr Gly Val Lys Val Asp Thr
```

```
            195                 200                 205
Lys Arg Leu Glu Gln Met Gly Ser Glu Leu Ala Glu Gln Leu Arg Ala
210                 215                 220

Val Glu Gln Arg Ile Tyr Glu Leu Ala Gly Gln Phe Asn Ile Asn
225                 230                 235                 240

Ser Pro Lys Gln Leu Gly Val Ile Leu Phe Glu Lys Leu Gln Leu Pro
            245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asn Asp Asp Asn Leu Ile Glu
370                 375                 380

Ala Phe Arg Arg Asp Leu Asp Ile His Thr Lys Thr Ala Met Asp Val
385                 390                 395                 400

Phe His Val Ser Glu Glu Val Thr Ala Arg Met Arg Arg Gln Ala
            405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Ala Ser Phe Pro Gly Val Lys Arg Tyr Met Glu Asn Ile
450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
530                 535                 540

Leu Glu Ala Pro Lys Glu Glu Ile Glu Arg Leu Cys Gln Leu Val Pro
545                 550                 555                 560

Glu Val Met Glu Gln Ala Val Thr Leu Arg Val Pro Leu Lys Val Asp
            565                 570                 575

Tyr His Tyr Gly Pro Thr Trp Tyr Asp Ala Lys
            580                 585

<210> SEQ ID NO 19
<211> LENGTH: 587
<212> TYPE: PRT
<213> ORGANISM: Artificial Sequence
```

<220> FEATURE:
<223> OTHER INFORMATION: Synthetic construct

<400> SEQUENCE: 19

```
Ala Glu Gly Glu Lys Pro Leu Ala Glu Met Glu Phe Ala Ile Val Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ile Trp Ala Leu Glu Gln Pro Phe Ile Asp Glu Leu
                165                 170                 175

Arg Arg Asn Glu Gln Asp Glu Leu Leu Thr Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Gly Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400
```

```
Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Glu Phe Ile Glu
            435                 440                 445

Arg Tyr Phe Ala Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Leu Ala Ala Arg Leu Lys Glu
                515                 520                 525

Glu Arg Leu Gln Ala Arg Leu Leu Gln Val His Asp Glu Leu Ile
    530                 535                 540

Leu Glu Ala Pro Lys Glu Glu Ile Glu Arg Leu Cys Gln Leu Val Pro
545                 550                 555                 560

Glu Val Met Glu Gln Ala Val Thr Leu Arg Val Pro Leu Lys Val Asp
                565                 570                 575

Tyr His Tyr Gly Pro Thr Trp Tyr Asp Ala Lys
                580                 585

<210> SEQ ID NO 20
<211> LENGTH: 587
<212> TYPE: PRT
<213> ORGANISM: Artificial Sequence
<220> FEATURE:
<223> OTHER INFORMATION: Synthetic construct

<400> SEQUENCE: 20

Ala Glu Glu Glu Lys Pro Leu Glu Glu Met Glu Phe Ala Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Met Arg Pro Glu Thr Ala Leu Ala
50                  55                  60

Ser Pro Gln Phe Leu Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Ile Ala Ala Val Ala Lys Met Lys
        115                 120                 125

Gln Tyr Glu Ala Val Arg Ser Asp Glu Ala Val Tyr Gly Lys Gly Val
    130                 135                 140

Lys Arg Ser Leu Pro Asp Glu Gln Thr Leu Ala Glu His Leu Val Arg
145                 150                 155                 160

Lys Ala Ala Ala Ile Trp Ala Leu Glu Gln Pro Phe Met Asp Asp Leu
                165                 170                 175
```

-continued

Arg Asn Asn Glu Gln Asp Gln Leu Leu Thr Glu Leu Glu Gln Pro Leu
            180                 185                 190

Ala Ala Ile Leu Ala Glu Met Glu Phe Thr Gly Val Asn Val Asp Thr
        195                 200                 205

Lys Arg Leu Glu Gln Met Gly Ser Glu Leu Ala Glu Gln Leu Lys Glu
    210                 215                 220

Ile Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Arg Phe Asn Gln Ala
305                 310                 315                 320

Leu Thr Gln Thr Gly Arg Leu Ser Ser Ala Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Gln Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Ala Ser Phe Pro Gly Val Lys Gln Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Gln Leu Gln Ala Arg Leu Leu Leu Gln Val His Asp Glu Leu Ile
    530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 21
<211> LENGTH: 587
<212> TYPE: PRT
<213> ORGANISM: Artificial Sequence
<220> FEATURE:
<223> OTHER INFORMATION: Synthetic construct

<400> SEQUENCE: 21

```
Thr Glu Glu Glu Lys Glu Leu Glu Asp Ile Asn Val Lys Thr Ala Asp
1               5                   10                  15

Glu Val Thr Ser Glu Met Leu Thr Asp Pro Ser Ala Leu Val Val Glu
            20                  25                  30

Gln Leu Gly Asp Asn Tyr His Glu Ala Asp Ile Ile Gly Phe Ala Ile
        35                  40                  45

Val Asn Glu Asn Gly Ala Phe Phe Ile Pro Lys Glu Thr Ala Leu Gln
50                  55                  60

Ser Pro Gln Phe Lys Glu Trp Val Glu Asp Thr Lys Lys Lys Trp
65                  70                  75                  80

Val Phe Asp Ser Lys Arg Ala Ile Val Ala Leu Arg Trp His Gly Ile
                85                  90                  95

Glu Leu Lys Gly Val Asp Phe Asp Val Leu Leu Ala Ser Tyr Ile Ile
            100                 105                 110

Asn Pro Ser Asn Ser Tyr Asp Asp Val Ala Ser Val Ala Lys Glu Tyr
        115                 120                 125

Gly Leu Asn Ile Val Ser Ser Asp Glu Ala Val Tyr Gly Lys Gly Ala
    130                 135                 140

Lys Arg Ala Val Pro Ala Glu Asp Glu Leu Ala Glu His Leu Gly Arg
145                 150                 155                 160

Lys Ala Ala Ala Ile Ser Ala Leu Arg Asp Lys Leu Leu Gln Ala Leu
                165                 170                 175

Glu Glu Asn Asp Gln Tyr Glu Leu Leu Thr Glu Leu Glu Met Pro Leu
            180                 185                 190

Ala Leu Ile Leu Gly Glu Met Glu Ser Thr Gly Val Lys Val Asp Val
        195                 200                 205

Glu Arg Leu Lys Arg Met Gly Glu Glu Leu Thr Glu Lys Leu Lys Glu
    210                 215                 220

Tyr Glu Glu Lys Ile His Glu Leu Ala Gly Glu Pro Phe Asn Ile Asn
225                 230                 235                 240

Ser Pro Lys Gln Leu Gly Val Ile Leu Phe Glu Lys Leu Gly Leu Pro
                245                 250                 255

Val Ile Lys Lys Thr Lys Thr Gly Tyr Ser Thr Ser Ala Asp Val Leu
            260                 265                 270

Glu Lys Leu Ala Asp Lys His Glu Ile Ile Arg Tyr Ile Leu His Tyr
        275                 280                 285

Arg Gln Ile Gly Lys Leu Gln Ser Thr Tyr Ile Glu Gly Leu Leu Lys
    290                 295                 300

Val Thr Arg Lys Asp Thr His Lys Val His Thr Arg Phe Asn Gln Ala
305                 310                 315                 320

Leu Thr Gln Thr Gly Arg Leu Ser Ser Thr Asp Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Glu Gly Trp Leu Ile Phe Ala Ala Asp Tyr Ser Gln Ile
        355                 360                 365
```

```
Glu Leu Arg Val Leu Ala His Ile Ser Lys Asp Glu Asn Leu Ile Glu
    370                 375                 380

Ala Phe Thr His Asp Met Asp Ile His Thr Lys Thr Ala Met Asp Val
385                 390                 395                 400

Phe His Val Ser Glu Asp Glu Val Thr Ser Ala Met Arg Arg Gln Ala
                405                 410                 415

Lys Ala Val Asn Phe Gly Ile Val Tyr Gly Ile Ser Asp Tyr Gly Leu
            420                 425                 430

Ser Gln Asn Leu Gly Ile Thr Arg Lys Glu Ala Gly Ala Phe Ile Glu
            435                 440                 445

Arg Tyr Leu Glu Ser Phe Pro Gly Val Lys Ala Tyr Met Glu Asp Ile
    450                 455                 460

Val Gln Glu Ala Lys Gln Lys Gly Tyr Val Thr Thr Leu Leu His Arg
465                 470                 475                 480

Arg Arg Tyr Ile Pro Glu Ile Thr Ser Arg Asn Phe Asn Ile Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Met Ala Ala Arg Leu Lys Glu
            515                 520                 525

Glu Asn Leu Gln Ala Arg Leu Leu Leu Gln Val His Asp Glu Leu Ile
    530                 535                 540

Phe Glu Ala Pro Lys Glu Glu Ile Glu Ile Leu Cys Lys Leu Val Pro
545                 550                 555                 560

Glu Val Met Glu His Ala Val Glu Leu Asp Val Pro Leu Lys Val Asp
                565                 570                 575

Tyr Ala Ser Gly Pro Ser Trp Tyr Asp Ala Lys
            580                 585

<210> SEQ ID NO 22
<211> LENGTH: 587
<212> TYPE: PRT
<213> ORGANISM: Artificial Sequence
<220> FEATURE:
<223> OTHER INFORMATION: Synthetic construct

<400> SEQUENCE: 22

Ala Glu Glu Glu Lys Pro Leu Glu Glu Met Glu Phe Ala Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
    50                  55                  60

Ser Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
    115                 120                 125

Gln Tyr Glu Ala Val Arg Ser Asp Glu Ala Val Tyr Gly Lys Gly Ala
130                 135                 140
```

```
Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
            165                 170                 175

Arg Asn Asn Glu Gln Asp Glu Leu Leu Thr Glu Leu Glu Gln Pro Leu
        180                 185                 190

Ala Leu Ile Leu Ala Glu Met Glu Phe Thr Gly Val Lys Val Asp Thr
    195                 200                 205

Lys Arg Leu Glu Gln Met Gly Glu Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
            245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
            405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Ala Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Gln Val His Asp Glu Leu Ile
    530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
```

```
                    565                 570                 575

Tyr His Tyr Gly Pro Thr Trp Tyr Asp Ala Lys
            580                 585

<210> SEQ ID NO 23
<211> LENGTH: 587
<212> TYPE: PRT
<213> ORGANISM: Artificial Sequence
<220> FEATURE:
<223> OTHER INFORMATION: Synthetic construct

<400> SEQUENCE: 23

Glu Glu Glu Glu Lys Pro Leu Glu Asp Ile Ser Phe Glu Ile Ala Asp
1               5                   10                  15

Glu Val Thr Glu Glu Met Leu Thr Asp Glu Ser Ala Leu Val Val Glu
            20                  25                  30

Val Leu Glu Glu Asn Tyr His Lys Ala Asp Ile Val Gly Phe Ala Ile
        35                  40                  45

Val Asn Glu Asn Gly Asn Phe Phe Ile Pro Thr Asp Thr Ala Leu Ala
    50                  55                  60

Ser Pro Gln Phe Lys Lys Trp Leu Glu Asp Glu Thr Lys Lys Lys Thr
65                  70                  75                  80

Val Phe Asp Ala Lys Arg Ala Ile Val Ala Leu Lys Trp Lys Gly Ile
                85                  90                  95

Glu Leu Lys Gly Val Asp Phe Asp Leu Leu Ile Ala Ser Tyr Leu Leu
            100                 105                 110

Asn Pro Ser Glu Thr Asn Asp Asp Phe Ala Ser Val Ala Lys Thr Lys
        115                 120                 125

Gly Tyr Asn Ala Val Gln Ser Asp Glu Ala Val Tyr Gly Lys Gly Ala
    130                 135                 140

Lys Arg Ala Val Pro Glu Glu Glu Lys Leu Ala Glu His Leu Ala Arg
145                 150                 155                 160

Lys Ala Ala Ala Ile Ser Ala Leu Lys Glu Thr Phe Ile Gln Glu Leu
                165                 170                 175

Lys Glu Asn Glu Gln Tyr Glu Leu Leu Thr Glu Leu Glu Met Pro Leu
            180                 185                 190

Ala Leu Ile Leu Ala Asp Met Glu Tyr Thr Gly Val Lys Val Asp Val
        195                 200                 205

Glu Arg Leu Lys Glu Met Gly Glu Glu Leu Ala Glu Arg Leu Lys Glu
    210                 215                 220

Ile Glu Gln Lys Ile Tyr Glu Leu Ala Gly Glu Glu Phe Asn Ile Asn
225                 230                 235                 240

Ser Pro Lys Gln Leu Gly Val Ile Leu Phe Glu Lys Leu Gly Leu Pro
                245                 250                 255

Val Ile Lys Lys Thr Lys Thr Gly Tyr Ser Thr Ser Ala Asp Val Leu
            260                 265                 270

Glu Lys Leu Ala Ser Lys His Glu Ile Ile Arg Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
                325                 330                 335

Ile Pro Ile Arg Leu Glu Glu Gly Arg Lys Ile Arg Gln Ala Phe Val
```

```
            340                 345                 350
Pro Ser Glu Glu Gly Trp Val Ile Phe Ala Ala Asp Tyr Ser Gln Ile
        355                 360                 365

Glu Leu Arg Val Leu Ala His Ile Ala Asn Asp Glu Lys Leu Ile Glu
    370                 375                 380

Ala Phe Arg His Asp Met Asp Ile His Thr Lys Thr Ala Met Asp Val
385                 390                 395                 400

Phe His Val Ser Glu Asp Glu Val Thr Ser Asn Met Arg Arg Gln Ala
                405                 410                 415

Lys Ala Val Asn Phe Gly Ile Val Tyr Gly Ile Ser Asp Tyr Gly Leu
            420                 425                 430

Ser Gln Asn Leu Gly Ile Thr Arg Lys Glu Ala Ala Glu Phe Ile Glu
        435                 440                 445

Arg Tyr Leu Glu Ser Phe Pro Gly Val Lys Glu Tyr Met Asp Asp Ile
    450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Met Ala Asn Arg Leu Lys Glu
        515                 520                 525

Glu Asn Leu Gln Ala Arg Leu Leu Leu Gln Val His Asp Glu Leu Ile
    530                 535                 540

Phe Glu Ala Pro Lys Glu Glu Ile Glu Lys Cys Lys Lys Ile Val Pro
545                 550                 555                 560

Glu Val Met Glu His Ala Val Glu Leu Lys Val Pro Leu Lys Val Asp
                565                 570                 575

Tyr Ser Tyr Gly Pro Thr Trp Tyr Asp Ala Lys
            580                 585

<210> SEQ ID NO 24
<211> LENGTH: 587
<212> TYPE: PRT
<213> ORGANISM: Artificial Sequence
<220> FEATURE:
<223> OTHER INFORMATION: Synthetic construct

<400> SEQUENCE: 24

Ala Glu Glu Glu Lys Pro Leu Ala Glu Met Glu Phe Ala Ile Ala Asp
1               5                   10                  15

Glu Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Ser Pro Gln Phe Leu Ala Trp Leu Gly Asp Glu Thr Lys Lys Lys Ser
65                  70                  75                  80

Met Phe Asp Ser Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Ala Ala Gly Asp Val Ala Ala Val Ala Lys Met Lys
```

-continued

```
                115                 120                 125
Gln Tyr Glu Ala Val Arg Ser Asp Glu Ala Val Tyr Gly Lys Gly Ala
130                 135                 140
Lys Arg Ser Val Pro Asp Glu Pro Thr Leu Ala Glu His Leu Val Arg
145                 150                 155                 160
Lys Ala Ala Ala Ile Trp Ala Leu Glu Gln Pro Phe Met Asp Glu Leu
                165                 170                 175
Arg Arg Asn Glu Gln Asp Arg Leu Leu Thr Glu Leu Glu Gln Pro Leu
                180                 185                 190
Ala Ser Ile Leu Ala Glu Met Glu Phe Thr Gly Val Lys Val Asp Thr
                195                 200                 205
Lys Arg Leu Glu Gln Met Gly Glu Glu Leu Thr Glu Gln Leu Lys Glu
210                 215                 220
Val Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
                245                 250                 255
Val Leu Lys Lys Thr Lys Thr Gly Tyr Ser Thr Ser Ala Asp Val Leu
                260                 265                 270
Glu Lys Leu Ala Pro His His Glu Ile Val Glu Asn Ile Leu His Tyr
                275                 280                 285
Arg Gln Leu Gly Lys Leu Gln Ser Thr Tyr Ile Glu Gly Leu Leu Lys
                290                 295                 300
Val Val His Pro Asp Thr Gly Lys Val His Thr Arg Phe Asn Gln Ala
305                 310                 315                 320
Leu Thr Gln Thr Gly Arg Leu Ser Ser Thr Glu Pro Asn Leu Gln Asn
                325                 330                 335
Ile Pro Ile Arg Leu Glu Glu Gly Arg Lys Ile Arg Gln Ala Phe Val
                340                 345                 350
Pro Ser Glu Pro Asp Trp Leu Ile Phe Ala Ala Asp Tyr Ser Gln Ile
                355                 360                 365
Glu Leu Arg Val Leu Ala His Ile Ala Asp Asp Asn Leu Ile Glu
370                 375                 380
Ala Phe Arg Arg Asp Leu Asp Ile His Thr Lys Thr Ala Met Asp Ile
385                 390                 395                 400
Phe His Val Ser Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
                420                 425                 430
Ala Gln Asn Leu Asn Ile Thr Arg Lys Glu Ala Ala Glu Phe Ile Glu
                435                 440                 445
Arg Tyr Phe Ala Ser Phe Pro Gly Val Lys Gln Tyr Met Glu Asn Ile
                450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
                485                 490                 495
Phe Ala Glu Arg Thr Ala Met Asn Thr Pro Ile Gln Gly Ser Ala Ala
                500                 505                 510
Asp Ile Ile Lys Lys Ala Met Ile Asp Leu Ala Ala Arg Leu Lys Glu
                515                 520                 525
Glu Arg Leu Gln Ala Arg Leu Leu Leu Gln Val His Asp Glu Leu Ile
530                 535                 540
```

-continued

Leu Glu Ala Pro Lys Glu Ile Glu Arg Leu Cys Lys Leu Val Pro
545                 550                 555                 560

Glu Val Met Glu Gln Ala Val Glu Leu Arg Val Pro Leu Lys Val Asp
            565                 570                 575

Tyr His Tyr Gly Pro Thr Trp Tyr Asp Ala Lys
        580                 585

<210> SEQ ID NO 25
<211> LENGTH: 587
<212> TYPE: PRT
<213> ORGANISM: Artificial Sequence
<220> FEATURE:
<223> OTHER INFORMATION: Synthetic construct

<400> SEQUENCE: 25

Ala Glu Glu Val Pro Leu Glu Glu Met Glu Phe Thr Ile Ala Asp
1               5                   10                  15

Glu Ile Thr Glu Glu Met Leu Ala Asp Lys Ala Ala Leu Val Val Glu
            20                  25                  30

Val Leu Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Val Ala Trp Leu Glu Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Glu Asn Glu Gln Asp Glu Leu Leu Thr Asp Leu Glu Gln Pro Leu
            180                 185                 190

Ser Ser Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Arg Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Ile Phe Asn Gln Ala
305                 310                 315                 320

```
Leu Thr Gln Thr Gly Arg Leu Ser Ser Thr Glu Pro Asn Leu Gln Asn
            325                 330                 335

Ile Pro Ile Arg Leu Glu Glu Gly Arg Lys Ile Arg Gln Ala Phe Val
        340                 345                 350

Pro Ser Glu Pro Asp Trp Leu Ile Phe Ala Ala Asp Tyr Ser Gln Ile
    355                 360                 365

Glu Leu Arg Val Leu Ala His Ile Ala Asp Asp Asn Leu Ile Glu
370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Glu Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Cys Gln Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 26
<211> LENGTH: 587
<212> TYPE: PRT
<213> ORGANISM: Artificial Sequence
<220> FEATURE:
<223> OTHER INFORMATION: Synthetic construct

<400> SEQUENCE: 26

Ala Glu Glu Glu Ala Pro Leu Glu Asp Ile Glu Phe Asp Ile Ala Asp
1               5                   10                  15

Glu Val Thr Glu Glu Met Leu Ala Asp Lys Ala Ala Leu Val Val Glu
                20                  25                  30

Val Gln Glu Asp Asn Tyr His Asp Ala Pro Ile Val Gly Phe Ala Ile
        35                  40                  45

Val Asn Glu His Gly Arg Phe Phe Ile Arg Thr Glu Thr Ala Leu Ala
    50                  55                  60

Ser Glu Ala Phe Lys Ala Trp Leu Ala Asp Glu Thr Lys Lys Lys Ser
65                  70                  75                  80

Val Phe Asp Ala Lys Arg Ala Ile Val Ala Leu Lys Trp Lys Gly Ile
                85                  90                  95
```

Glu Leu Arg Gly Val Asp Phe Asp Leu Leu Ala Ala Tyr Leu Leu
            100                 105                 110

Asn Pro Ala Gln Thr Ala Asp Val Ala Ala Val Ala Lys Met Lys
            115                 120                 125

Gln Tyr His Ala Val Arg Ser Asp Glu Ala Val Tyr Gly Lys Gly Ala
            130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Lys Asn Glu Gln Asp Glu Leu Phe Thr Glu Leu Glu Leu Pro Leu
            180                 185                 190

Ala Leu Ile Leu Ala Glu Met Glu Phe Thr Gly Val Lys Val Asp Thr
            195                 200                 205

Lys Arg Leu Glu Gln Met Gly Glu Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
            245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asn Asp Asp Asn Leu Ile Glu
            370                 375                 380

Ala Phe Arg Arg Asp Met Asp Ile His Thr Lys Thr Ala Met Asp Val
385                 390                 395                 400

Phe His Val Ser Glu Asp Val Thr Ser Asn Met Arg Arg Gln Ala
                405                 410                 415

Lys Ala Val Asn Phe Gly Ile Val Tyr Gly Ile Ser Asp Tyr Gly Leu
            420                 425                 430

Ser Gln Asn Leu Gly Ile Thr Arg Lys Glu Ala Ala Glu Phe Ile Glu
            435                 440                 445

Arg Tyr Phe Glu Ser Phe Pro Gly Val Lys Glu Tyr Met Glu Asp Ile
            450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Met Ala Ala Arg Leu Lys Glu
            515                 520                 525

Glu Arg Leu Gln Ala Arg Leu Leu Gln Val His Asp Glu Leu Ile
    530                 535                 540

Phe Glu Ala Pro Lys Glu Ile Glu Arg Leu Glu Lys Leu Val Pro
545                 550                 555                 560

Glu Val Met Glu His Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 27
<211> LENGTH: 587
<212> TYPE: PRT
<213> ORGANISM: Artificial Sequence
<220> FEATURE:
<223> OTHER INFORMATION: Synthetic construct

<400> SEQUENCE: 27

Ala Glu Glu Glu Val Pro Leu Glu Glu Met Glu Phe Val Ile Ala Asp
1               5                   10                  15

Glu Ile Thr Glu Glu Met Leu Ala Asp Lys Ala Leu Val Val Glu
            20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Ala Glu Thr Ala Leu Ala
    50                  55                  60

Asp Pro Gln Phe Val Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Glu Asn Glu Gln Asp Glu Leu Leu Ile Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Arg Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
        435                 440                 445

Arg Tyr Phe Ala Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Cys Gln Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 28
<211> LENGTH: 587
<212> TYPE: PRT
<213> ORGANISM: Artificial Sequence
<220> FEATURE:
<223> OTHER INFORMATION: Synthetic construct

<400> SEQUENCE: 28

Glu Glu Glu Glu Lys Pro Leu Ala Lys Ile Ala Phe Thr Leu Ala Asp
1               5                   10                  15

Arg Val Thr Asp Glu Met Leu Ala Asp Lys Ala Ala Leu Val Val Glu
            20                  25                  30

Val Val Glu Asp Asn Tyr His Asp Ala Pro Ile Val Gly Ile Ala Val
        35                  40                  45

Val Asn Glu His Gly Arg Phe Phe Leu Arg Pro Glu Thr Ala Leu Ala
    50                  55                  60

```
Asp Pro Gln Phe Val Ala Trp Leu Gly Asp Glu Thr Lys Lys Lys Ser
 65                  70                  75                  80

Val Phe Asp Ser Lys Arg Ala Ala Val Ala Leu Lys Trp Lys Gly Ile
                 85                  90                  95

Glu Leu Cys Gly Val Ser Phe Asp Leu Leu Ala Ala Tyr Leu Leu
            100                 105                 110

Asp Pro Ala Gln Gly Val Asp Val Ala Ala Ala Lys Met Lys
            115                 120                 125

Gln Tyr His Ala Val Arg Pro Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ile Trp Ala Leu Glu Arg Pro Phe Leu Asp Glu Leu
                165                 170                 175

Arg Arg Asn Glu Gln Asp Arg Leu Leu Val Glu Leu Glu Gln Pro Leu
            180                 185                 190

Ser Ser Ile Leu Ala Glu Met Glu Phe Ala Gly Val Lys Val Asp Thr
        195                 200                 205

Lys Arg Leu Glu Gln Met Gly Glu Glu Leu Ala Glu Gln Leu Lys Glu
210                 215                 220

Gln Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro Tyr His Glu Ile Val Glu Asn Ile Leu His Tyr
        275                 280                 285

Arg Gln Leu Gly Lys Leu Gln Ser Thr Tyr Ile Glu Gly Leu Leu Lys
        290                 295                 300

Val Val Arg Pro Asp Thr Lys Lys Val His Thr Ile Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Ser Asp Trp Leu Ile Phe Ala Ala Asp Tyr Ser Gln Ile
        355                 360                 365

Glu Leu Arg Val Leu Ala His Ile Ala Glu Asp Glu Asn Leu Met Glu
        370                 375                 380

Ala Phe Arg Arg Asp Leu Asp Ile His Thr Lys Thr Ala Met Asp Ile
385                 390                 395                 400

Phe Gln Val Ser Glu Asp Glu Val Thr Pro Asn Met Arg Arg Gln Ala
                405                 410                 415

Lys Ala Val Asn Phe Gly Ile Val Tyr Gly Ile Ser Tyr Gly Leu
            420                 425                 430

Ser Gln Asn Leu Gly Ile Ser Arg Lys Glu Ala Ala Glu Phe Ile Glu
        435                 440                 445

Arg Tyr Phe Glu Ser Phe Pro Gly Val Lys Arg Tyr Met Glu Asn Ile
        450                 455                 460

Val Gln Glu Ala Lys Gln Lys Gly Tyr Val Thr Thr Leu Leu His Arg
465                 470                 475                 480

Arg Arg Tyr Asp Pro Asp Ile Thr Ser Arg Asn Phe Asn Val Arg Ser
```

```
                      485                 490                 495
Phe Ala Glu Arg Met Ala Met Asn Thr Pro Ile Gln Gly Ser Ala Ala
                500                 505                 510

Asp Ile Ile Lys Lys Ala Met Ile Asp Leu Asn Ala Arg Leu Lys Glu
            515                 520                 525

Glu Arg Leu Gln Ala Arg Leu Leu Gln Val His Asp Glu Leu Ile
        530                 535                 540

Leu Glu Ala Pro Lys Glu Glu Met Glu Arg Leu Cys Arg Leu Val Pro
545                 550                 555                 560

Glu Val Met Glu Gln Ala Val Thr Leu Arg Val Pro Leu Lys Val Asp
                565                 570                 575

Tyr His Tyr Gly Ser Thr Trp Tyr Asp Ala Lys
                580                 585
```

<210> SEQ ID NO 29
<211> LENGTH: 587
<212> TYPE: PRT
<213> ORGANISM: Artificial Sequence
<220> FEATURE:
<223> OTHER INFORMATION: Synthetic construct

<400> SEQUENCE: 29

```
Ala Glu Glu Glu Lys Pro Leu Ala Glu Met Glu Phe Ala Ile Ala Asp
1               5                   10                  15

Glu Val Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
        50                  55                  60

Asp Ser Gln Phe Leu Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Leu Asp Glu Leu
                165                 170                 175

Arg Arg Asn Glu Gln Asp Arg Leu Leu Thr Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Arg Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
```

```
                260                 265                 270
Glu Lys Leu Ala Pro His His Glu Ile Val Glu Asn Ile Leu His Tyr
            275                 280                 285
Arg Gln Leu Gly Lys Leu Gln Ser Thr Tyr Ile Glu Gly Leu Leu Lys
        290                 295                 300
Val Val His Pro Asp Thr Gly Lys Val His Thr Met Phe Asn Gln Ala
305                 310                 315                 320
Leu Thr Gln Thr Gly Arg Leu Ser Ser Thr Glu Pro Asn Leu Gln Asn
                325                 330                 335
Ile Pro Ile Arg Leu Glu Glu Gly Arg Lys Ile Arg Gln Ala Phe Val
            340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Asp Asp Asn Leu Ile Glu
            370                 375                 380
Ala Phe Arg Arg Asp Leu Asp Ile His Thr Lys Thr Ala Met Asp Ile
385                 390                 395                 400
Phe His Val Ser Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
            420                 425                 430
Ala Gln Asn Leu Asn Ile Thr Arg Lys Glu Ala Ala Glu Phe Ile Glu
        435                 440                 445
Arg Tyr Phe Ala Ser Phe Pro Gly Val Lys Arg Tyr Met Glu Asn Ile
    450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
                485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Leu Ala Ala Arg Leu Lys Glu
        515                 520                 525
Glu Arg Leu Gln Ala Arg Leu Leu Leu Gln Val His Asp Glu Leu Ile
    530                 535                 540
Leu Glu Ala Pro Lys Glu Glu Ile Glu Arg Leu Cys Gln Leu Val Pro
545                 550                 555                 560
Glu Val Met Glu Gln Ala Val Thr Leu Arg Val Pro Leu Lys Val Asp
                565                 570                 575
Tyr His Tyr Gly Pro Thr Trp Tyr Asp Ala Lys
            580                 585

<210> SEQ ID NO 30
<211> LENGTH: 587
<212> TYPE: PRT
<213> ORGANISM: Artificial Sequence
<220> FEATURE:
<223> OTHER INFORMATION: Synthetic construct

<400> SEQUENCE: 30

Ala Glu Glu Glu Val Pro Leu Ala Glu Met Glu Phe Val Ile Ala Asp
1               5                  10                  15
Glu Ile Thr Glu Glu Met Leu Ala Asp Lys Ala Ala Leu Val Val Glu
            20                  25                  30
Val Met Glu Glu Asn Tyr His Asp Ala Pro Ile Val Gly Ile Ala Leu
```

```
                35                  40                  45
Val Asn Glu His Gly Arg Phe Phe Leu Arg Pro Glu Thr Ala Leu Ala
 50                  55                  60
Asp Pro Gln Phe Leu Ala Trp Leu Ala Asp Glu Thr Lys Lys Lys Ser
 65                  70                  75                  80
Met Phe Asp Ala Lys Arg Ala Ala Val Ala Leu Lys Trp Lys Gly Ile
                 85                  90                  95
Glu Leu Arg Gly Val Ala Phe Asp Leu Leu Ala Ala Tyr Leu Leu
                100                 105                 110
Asn Pro Ala Gln Asp Ala Gly Asp Val Ala Val Ala Lys Met Lys
                115                 120                 125
Gln Tyr Glu Ala Val Arg Ser Asp Glu Ala Val Tyr Gly Lys Gly Ala
                130                 135                 140
Lys Arg Ser Leu Pro Asp Glu Pro Thr Leu Ala Glu His Leu Val Arg
145                 150                 155                 160
Lys Ala Ala Ala Ile Trp Ala Leu Glu Arg Pro Phe Leu Asp Glu Leu
                165                 170                 175
Arg Arg Asn Glu Gln Asp Glu Leu Leu Thr Lys Leu Glu Gln Pro Leu
                180                 185                 190
Ala Thr Ile Leu Ala Glu Met Glu Phe Thr Gly Val Lys Val Asp Thr
                195                 200                 205
Lys Arg Leu Glu Gln Met Gly Ser Glu Leu Ala Glu Gln Leu Arg Ala
                210                 215                 220
Val Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
                245                 250                 255
Val Leu Lys Lys Thr Lys Thr Gly Tyr Ser Thr Ser Ala Asp Val Leu
                260                 265                 270
Glu Lys Leu Ala Pro His His Glu Ile Val Glu Asn Ile Leu His Tyr
                275                 280                 285
Arg Gln Leu Gly Lys Leu Gln Ser Thr Tyr Ile Glu Gly Leu Leu Lys
                290                 295                 300
Val Val His Pro Asp Thr Gly Lys Val His Thr Met Phe Asn Gln Ala
305                 310                 315                 320
Leu Thr Gln Thr Gly Arg Leu Ser Ser Ala Glu Pro Asn Leu Gln Asn
                325                 330                 335
Ile Pro Ile Arg Leu Glu Glu Gly Arg Lys Ile Arg Gln Ala Phe Val
                340                 345                 350
Pro Ser Glu Pro Asp Trp Leu Ile Phe Ala Ala Asp Tyr Ser Gln Ile
                355                 360                 365
Glu Leu Arg Val Leu Ala His Ile Ala Asp Asp Asn Leu Ile Glu
                370                 375                 380
Ala Phe Arg Arg Asp Leu Asp Ile His Thr Lys Thr Ala Met Asp Ile
385                 390                 395                 400
Phe His Val Ser Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
                420                 425                 430
Ala Gln Asn Leu Asn Ile Thr Arg Lys Glu Ala Ala Glu Phe Ile Glu
                435                 440                 445
Arg Tyr Phe Ala Ser Phe Pro Gly Val Lys Arg Tyr Met Glu Asn Ile
450                 455                 460
```

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
        500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Gln Val His Asp Glu Leu Ile
        530                 535                 540

Leu Glu Ala Pro Lys Glu Ile Glu Arg Leu Cys Gln Leu Val Pro
545                 550                 555                 560

Glu Val Met Glu Gln Ala Val Glu Leu Arg Val Pro Leu Lys Val Asp
            565                 570                 575

Tyr His Tyr Gly Pro Thr Trp Tyr Asp Ala Lys
            580                 585

<210> SEQ ID NO 31
<211> LENGTH: 587
<212> TYPE: PRT
<213> ORGANISM: Artificial Sequence
<220> FEATURE:
<223> OTHER INFORMATION: Synthetic construct

<400> SEQUENCE: 31

Ala Glu Asp Glu Lys Pro Leu Ala Glu Met Glu Phe Val Ile Ala Asp
1               5                   10                  15

Gly Ile Thr Asp Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Val Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Pro Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Arg Leu Leu Ile Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Arg Ala
    210                 215                 220

Val Glu Gln Arg Ile Tyr Glu Leu Ala Gly Gln Glu Phe Asn Ile Asn
225                 230                 235                 240

```
Ser Pro Lys Gln Leu Gly Val Ile Leu Phe Glu Lys Leu Gln Leu Pro
            245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
            370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
            405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
            435                 440                 445

Arg Tyr Phe Ala Ser Phe Pro Gly Val Lys Arg Tyr Met Glu Asn Ile
            450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Leu Gln Val His Asp Glu Leu Ile
            530                 535                 540

Leu Glu Ala Pro Lys Glu Glu Met Glu Arg Leu Cys Arg Leu Val Pro
545                 550                 555                 560

Glu Val Met Glu Gln Ala Val Thr Leu Arg Val Pro Leu Lys Val Asp
            565                 570                 575

Tyr His Tyr Gly Pro Thr Trp Tyr Asp Ala Lys
            580                 585

<210> SEQ ID NO 32
<211> LENGTH: 587
<212> TYPE: PRT
<213> ORGANISM: Artificial Sequence
<220> FEATURE:
<223> OTHER INFORMATION: Synthetic construct

<400> SEQUENCE: 32

Glu Glu Glu Glu Glu Pro Leu Glu Asp Ile Ser Phe Glu Ile Val Glu
1               5                   10                  15
```

```
Glu Val Thr Glu Glu Met Leu Thr Asp Glu Ser Ala Leu Val Val Glu
                 20                  25                  30

Val Leu Glu Glu Asn Tyr His Lys Ala Asp Ile Val Gly Phe Ala Ile
             35                  40                  45

Val Asn Glu Asn Gly Asn Phe Phe Ile Pro Thr Asp Thr Ala Leu Ala
         50                  55                  60

Ser Glu Ala Phe Lys Lys Trp Leu Glu Asp Glu Thr Lys Lys Lys Thr
 65                  70                  75                  80

Val Phe Asp Ala Lys Arg Ala Ile Val Ala Leu Lys Trp Lys Gly Ile
                 85                  90                  95

Glu Leu Lys Gly Val Asp Phe Asp Leu Leu Ile Ala Ser Tyr Leu Leu
            100                 105                 110

Asn Pro Ser Glu Thr Asn Asp Asp Phe Ala Ser Val Ala Lys Thr Lys
            115                 120                 125

Gly Tyr Asn Ala Val Gln Ser Asp Glu Ala Val Tyr Gly Lys Gly Ala
        130                 135                 140

Lys Arg Ala Val Pro Glu Glu Glu Lys Leu Ala Glu His Leu Ala Arg
145                 150                 155                 160

Lys Ala Ala Ala Ile Ser Ala Leu Lys Glu Thr Phe Ile Gln Glu Leu
                165                 170                 175

Lys Glu Asn Glu Gln Tyr Glu Leu Phe Thr Asp Leu Glu Met Pro Leu
            180                 185                 190

Ala Leu Ile Leu Ala Asp Met Glu Tyr Thr Gly Val Lys Val Asp Val
        195                 200                 205

Glu Arg Leu Lys Glu Met Gly Glu Glu Leu Ala Glu Arg Leu Lys Glu
            210                 215                 220

Ile Glu Gln Lys Ile Tyr Glu Leu Ala Gly Glu Glu Phe Asn Ile Asn
225                 230                 235                 240

Ser Pro Lys Gln Leu Gly Val Ile Leu Phe Glu Lys Leu Gly Leu Pro
                245                 250                 255

Val Ile Lys Lys Thr Lys Thr Gly Tyr Ser Thr Ser Ala Asp Val Leu
            260                 265                 270

Glu Lys Leu Ala Ser Lys His Glu Ile Ile Arg Asn Ile Leu His Tyr
        275                 280                 285

Arg Gln Leu Gly Lys Leu Gln Ser Thr Tyr Ile Glu Gly Leu Leu Lys
    290                 295                 300

Val Val His Gln Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Glu Gly Trp Val Ile Phe Ala Ala Asp Tyr Ser Gln Ile
        355                 360                 365

Glu Leu Arg Val Leu Ala His Ile Ala Asn Asp Glu Lys Leu Ile Glu
    370                 375                 380

Ala Phe Arg His Asp Met Asp Ile His Thr Lys Thr Ala Met Asp Val
385                 390                 395                 400

Phe His Val Ser Glu Asp Glu Val Thr Ser Asn Met Arg Arg Gln Ala
                405                 410                 415

Lys Ala Val Asn Phe Gly Ile Val Tyr Gly Ile Ser Asp Tyr Gly Leu
            420                 425                 430
```

-continued

```
Ser Gln Asn Leu Gly Ile Thr Arg Lys Glu Ala Ala Glu Phe Ile Glu
        435                 440                 445

Arg Tyr Leu Glu Ser Phe Pro Gly Val Lys Glu Tyr Met Asp Asp Ile
450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Met Ala Asn Arg Leu Lys Glu
            515                 520                 525

Glu Asn Leu Gln Ala Arg Leu Leu Gln Val His Asp Glu Leu Ile
        530                 535                 540

Phe Glu Ala Pro Lys Glu Glu Ile Glu Lys Leu Lys Lys Ile Val Pro
545                 550                 555                 560

Glu Val Met Glu His Ala Val Glu Leu Lys Val Pro Leu Lys Val Asp
                565                 570                 575

Tyr Ser Tyr Gly Pro Thr Trp Tyr Asp Ala Lys
                580                 585
```

<210> SEQ ID NO 33
<211> LENGTH: 587
<212> TYPE: PRT
<213> ORGANISM: Artificial Sequence
<220> FEATURE:
<223> OTHER INFORMATION: Synthetic construct

<400> SEQUENCE: 33

```
Ala Glu Lys Glu Leu Pro Leu Met Glu Met Glu Phe Ala Asp Ala Asp
1               5                   10                  15

Thr Ile Thr Met Glu Met Leu Ala Asp Lys Ala Ala Leu Val Val Glu
                20                  25                  30

Val Met Glu Glu Asn Tyr His Asp Ala Pro Ile Val Gly Ile Ala Asn
            35                  40                  45

Val Asn Glu His Gly Arg Phe Phe Leu Arg Thr Glu Leu Ala Leu Ala
        50                  55                  60

Asp Phe Gln Phe Val Ala Trp Leu Glu Asp Glu Thr Lys Lys Lys Ser
65                  70                  75                  80

Met Phe Asp Arg Lys Arg Ala Ala Val Ala Leu Lys Trp Lys Gly Ile
                85                  90                  95

Glu Leu Val Gly Val Asp Phe Asp Leu Leu Ala Ala Tyr Leu Leu
                100                 105                 110

Ala Pro Ala Gln Asp Asp Gly Asp Ala Ala Lys Ala Lys Met Lys
        115                 120                 125

Gln Tyr Glu Ala Val Arg Glu Asp Gly Ala Val Tyr Gly Lys Gly Ala
130                 135                 140

Lys Arg Pro Asp Pro Asp Glu Leu Ala Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Glu Asn Glu Gln Asp Leu Leu Leu Leu Glu Leu Gln Pro Leu
                180                 185                 190

Ile Leu Ile Leu Ala Glu Met Glu Phe Thr Gly Val Asp Val Asp Thr
                195                 200                 205
```

Lys Arg Leu Glu Gln Met Gly Leu Glu Leu Ala Glu Gln Leu Val Glu
210                 215                 220

Gln Glu Gln Arg Ile Tyr Glu Leu Ala Gly Gln Glu Phe Asn Ile Asn
225                 230                 235                 240

Ser Pro Lys Gln Leu Gly Leu Ile Leu Phe Glu Lys Leu Gln Leu Pro
            245                 250                 255

Val Leu Lys Lys Thr Lys Thr Gly Tyr Ser Thr Ser Ala Asp Val Leu
260                 265                 270

Glu Lys Leu Ala Pro Glu His Glu Ile Val Glu Asn Ile Leu His Tyr
            275                 280                 285

Arg Gln Leu Gly Lys Leu Gln Ser Thr Tyr Ile Glu Gly Leu Leu Lys
290                 295                 300

Val Val Asp Thr Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Leu Trp Leu Ile Phe Ala Ala Asp Tyr Ser Gln Ile
            355                 360                 365

Glu Leu Arg Val Leu Ala His Ile Ala Asp Asp Asn Leu Ala Glu
370                 375                 380

Ala Phe Arg Arg Asp Leu Asp Ile His Thr Lys Thr Ala Met Asp Ile
385                 390                 395                 400

Phe His Val Ser Glu Glu Val Thr Ala Arg Met Arg Arg Gln Ala
            405                 410                 415

Lys Ala Val Asn Phe Gly Ile Val Tyr Gly Ile Ser Asp Tyr Gly Leu
            420                 425                 430

Ala Gln Asn Leu Asn Ile Lys Arg Lys Glu Ala Ala Glu Phe Ile Glu
            435                 440                 445

Arg Tyr Phe Ala Ser Phe Pro Gly Val Lys Arg Tyr Met Glu Val Ile
            450                 455                 460

Val Gln Glu Ala Lys Gln Lys Gly Tyr Val Thr Thr Leu Leu His Arg
465                 470                 475                 480

Arg Arg Tyr Asp Pro Asp Ile Thr Ser Arg Asn Phe Asn Val Arg Ser
            485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Gln Leu Gln Ala Arg Leu Leu Leu Gln Val His Asp Glu Leu Ile
            530                 535                 540

Leu Glu Ala Pro Lys Glu Glu Met Glu Arg Leu Cys Val Leu Val Pro
545                 550                 555                 560

Glu Val Met Glu Gln Ala Val Arg Leu Arg Val Pro Leu Lys Val Asp
            565                 570                 575

Tyr His Tyr Gly Trp Thr Trp Tyr Asp Ala Lys
            580                 585

<210> SEQ ID NO 34
<211> LENGTH: 587
<212> TYPE: PRT
<213> ORGANISM: Artificial Sequence
<220> FEATURE:
<223> OTHER INFORMATION: Synthetic construct

```
<400> SEQUENCE: 34

Ser Glu Glu Lys Pro Leu Ala Lys Ile Ala Phe Asp Leu Ala Asp
1               5                   10                  15

Arg Val Thr Glu Glu Met Leu Ala Asp Lys Ala Ala Leu Val Val Glu
            20                  25                  30

Val Gln Glu Asp Asn Tyr His Asp Ala Pro Ile Val Gly Ile Ala Val
        35                  40                  45

Val Asn Glu His Gly Arg Phe Leu Arg Ala Glu Leu Ala Leu Ala
    50                  55                  60

Ser Pro Gln Phe Val Ala Trp Leu Gly Asp Glu Thr Lys Lys Ser
65              70                  75                  80

Met Phe Asp Ser Lys Arg Ala Ile Val Ala Leu Lys Trp Lys Gly Ile
                85                  90                  95

Glu Leu Cys Gly Val Asp Phe Asp Leu Leu Ala Ala Tyr Leu Leu
            100                 105                 110

Asp Pro Ala Gln Thr Asp Asp Ala Ala Lys Ala Lys Met Lys
            115                 120                 125

Gln Tyr His Ala Val Arg Pro Asp Glu Ala Val Tyr Gly Lys Gly Ala
        130                 135                 140

Lys Arg Ala Val Pro Asp Glu Pro Val Leu Ala Glu His Leu Val Arg
145             150                 155                 160

Lys Ala Ala Ile Trp Ala Leu Glu Glu Pro Phe Leu Asp Glu Leu
                165                 170                 175

Arg Arg Asn Glu Gln Asp Arg Leu Leu Ile Glu Leu Glu Met Pro Leu
            180                 185                 190

Ser Ser Ile Leu Ala Glu Met Glu Phe Ala Gly Val Lys Val Asp Thr
        195                 200                 205

Lys Arg Leu Glu Gln Met Gly Glu Glu Leu Ala Glu Gln Leu Arg Thr
210                 215                 220

Val Glu Gln Arg Ile Tyr Glu Leu Ala Gly Glu Phe Asn Ile Asn
225                 230                 235                 240

Ser Pro Lys Gln Leu Gly Leu Ile Leu Phe Glu Lys Leu Gln Leu Pro
            245                 250                 255

Val Leu Lys Lys Thr Lys Thr Gly Tyr Ser Thr Ser Ala Asp Val Leu
            260                 265                 270

Glu Lys Leu Ala Pro Tyr His Glu Ile Val Glu Asn Ile Leu His Tyr
        275                 280                 285

Arg Gln Leu Gly Lys Leu Gln Ser Thr Tyr Ile Glu Gly Leu Leu Lys
290                 295                 300

Val Val His Pro Asp Thr Lys Lys Val His Thr Ile Phe Asn Gln Ala
305                 310                 315                 320

Leu Thr Gln Thr Gly Arg Leu Ser Ser Thr Glu Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Ser Asp Trp Leu Ile Phe Ala Ala Asp Tyr Ser Gln Ile
        355                 360                 365

Glu Leu Arg Val Leu Ala His Ile Ala Glu Asp Asn Leu Met Glu
        370                 375                 380

Ala Phe Arg Arg Asp Leu Asp Ile His Thr Lys Thr Ala Met Asp Val
385                 390                 395                 400

Phe Gln Val Ser Glu Asp Glu Val Thr Pro Arg Met Arg Arg Gln Ala
```

```
                    405                 410                 415
Lys Ala Val Asn Phe Gly Ile Val Tyr Gly Ile Ser Asp Tyr Gly Leu
                420                 425                 430

Ser Gln Asn Leu Gly Ile Ser Arg Lys Glu Ala Ala Glu Phe Ile Glu
            435                 440                 445

Arg Tyr Phe Glu Ser Phe Pro Gly Val Lys Arg Tyr Met Glu Asn Ile
        450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Met Ala Met Asn Thr Pro Ile Gln Gly Ser Ala Ala
                500                 505                 510

Asp Ile Ile Lys Lys Ala Met Ile Asp Leu Asn Ala Arg Leu Lys Glu
                515                 520                 525

Glu Arg Leu Gln Ala Arg Leu Leu Leu Gln Val His Asp Glu Leu Ile
            530                 535                 540

Leu Glu Ala Pro Lys Glu Glu Met Glu Arg Leu Cys Arg Leu Val Pro
545                 550                 555                 560

Glu Val Met Glu Gln Ala Val Thr Leu Arg Val Pro Leu Lys Val Asp
                565                 570                 575

Tyr His Tyr Gly Ser Thr Trp Tyr Asp Ala Lys
                580                 585

<210> SEQ ID NO 35
<211> LENGTH: 587
<212> TYPE: PRT
<213> ORGANISM: Artificial Sequence
<220> FEATURE:
<223> OTHER INFORMATION: Synthetic construct

<400> SEQUENCE: 35

Ala Glu Glu Glu Lys Pro Leu Glu Glu Met Glu Phe Ala Ile Ala Asp
1               5                   10                  15

Glu Val Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
        50                  55                  60

Ser Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Asn Asn Glu Gln Asp Glu Leu Leu Thr Glu Leu Glu Gln Pro Leu
```

```
            180                 185                 190
Ala Ala Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Lys Glu
        210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
        290                 295                 300

Val Val His Pro Asp Thr Gly Lys Val His Thr Arg Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
        370                 375                 380

Ala Phe Arg Arg Asp Leu Asp Ile His Thr Lys Thr Ala Met Asp Ile
385                 390                 395                 400

Phe His Val Ser Glu Asp Glu Val Thr Ala Asn Met Arg Arg Gln Ala
                405                 410                 415

Lys Ala Val Asn Phe Gly Ile Val Tyr Gly Ile Ser Asp Tyr Gly Leu
            420                 425                 430

Ser Gln Asn Leu Asn Ile Thr Arg Lys Glu Ala Ala Glu Phe Ile Glu
        435                 440                 445

Arg Tyr Phe Glu Ser Phe Pro Gly Val Lys Arg Tyr Met Glu Asn Ile
        450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Leu Gln Val His Asp Glu Leu Ile
        530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
            580                 585

<210> SEQ ID NO 36
```

<211> LENGTH: 587
<212> TYPE: PRT
<213> ORGANISM: Artificial Sequence
<220> FEATURE:
<223> OTHER INFORMATION: Synthetic construct

<400> SEQUENCE: 36

```
Ala Glu Glu Lys Pro Leu Glu Asp Ile Glu Phe Glu Ile Ala Asp
1               5                   10                  15

Glu Val Thr Glu Met Leu Ala Asp Glu Ala Ala Leu Val Val Glu
            20                  25                  30

Val Leu Glu Glu Asn Tyr His Asp Ala Pro Ile Val Gly Phe Ala Leu
            35                  40                  45

Val Asn Glu His Gly Arg Phe Phe Ile Arg Thr Glu Thr Ala Leu Ala
50                  55                  60

Ser Ser Gln Phe Lys Ala Trp Leu Glu Asp Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
                100                 105                 110

Asn Pro Ala Gln Ser Ala Gly Asp Val Ala Ala Val Ala Lys Met Lys
            115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ile Trp Ala Leu Glu Glu Pro Phe Ile Asp Glu Leu
                165                 170                 175

Arg Glu Asn Glu Gln Asp Glu Leu Phe Thr Glu Leu Glu Met Pro Leu
            180                 185                 190

Ala Leu Ile Leu Ala Glu Met Glu Phe Thr Gly Val Lys Val Asp Thr
        195                 200                 205

Lys Arg Leu Glu Gln Met Gly Glu Glu Leu Ala Glu Gln Leu Lys Ala
210                 215                 220

Ile Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asn Asp Glu Asn Leu Ile Glu
    370                 375                 380
```

```
Ala Phe Arg Arg Asp Leu Asp Ile His Thr Lys Thr Ala Met Asp Ile
385                 390                 395                 400

Phe His Val Ser Glu Asp Glu Val Thr Ala Asn Met Arg Arg Gln Ala
            405                 410                 415

Lys Ala Val Asn Phe Gly Ile Val Tyr Gly Ile Ser Asp Tyr Gly Leu
        420                 425                 430

Ser Gln Asn Leu Asn Ile Thr Arg Lys Glu Ala Ala Glu Phe Ile Glu
            435                 440                 445

Arg Tyr Phe Glu Ser Phe Pro Gly Val Lys Gln Tyr Met Glu Asp Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Leu Gln Val His Asp Glu Leu Ile
    530                 535                 540

Leu Glu Ala Pro Lys Glu Glu Ile Glu Arg Leu Cys Lys Leu Val Pro
545                 550                 555                 560

Glu Val Met Glu Gln Ala Val Glu Leu Arg Val Pro Leu Lys Val Asp
            565                 570                 575

Tyr His Tyr Gly Pro Thr Trp Tyr Asp Ala Lys
            580                 585

<210> SEQ ID NO 37
<211> LENGTH: 587
<212> TYPE: PRT
<213> ORGANISM: Artificial Sequence
<220> FEATURE:
<223> OTHER INFORMATION: Synthetic construct

<400> SEQUENCE: 37

Ala Glu Glu Glu Lys Pro Leu Ala Glu Met Glu Phe Val Ile Ala Asp
1               5                   10                  15

Glu Ile Thr Asp Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
50                  55                  60

Ser Pro Gln Phe Val Ala Trp Leu Ala Asp Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Pro Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160
```

-continued

```
Lys Ala Ala Ala Ile Trp Ala Leu Glu Arg Pro Phe Leu Asp Glu Leu
                165                 170                 175
Arg Arg Asn Glu Gln Asp Arg Leu Leu Thr Glu Leu Glu Gln Pro Leu
            180                 185                 190
Ala Thr Ile Leu Ala Glu Met Glu Phe Thr Gly Val Lys Val Asp Thr
        195                 200                 205
Lys Arg Leu Glu Gln Met Gly Ser Glu Leu Ala Glu Gln Leu Lys Glu
    210                 215                 220
Val Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
                245                 250                 255
Val Leu Lys Lys Thr Lys Thr Gly Tyr Ser Thr Ser Ala Asp Val Leu
            260                 265                 270
Glu Lys Leu Ala Pro His His Glu Ile Val Glu Asn Ile Leu His Tyr
        275                 280                 285
Arg Gln Leu Gly Lys Leu Gln Ser Thr Tyr Ile Glu Gly Leu Leu Lys
    290                 295                 300
Val Val His Pro Asp Thr Gly Lys Val His Thr Arg Phe Asn Gln Ala
305                 310                 315                 320
Leu Thr Gln Thr Gly Arg Leu Ser Ser Ala Glu Pro Asn Leu Gln Asn
                325                 330                 335
Ile Pro Ile Arg Leu Glu Glu Gly Arg Lys Ile Arg Gln Ala Phe Val
            340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Asp Asp Asn Leu Ile Glu
    370                 375                 380
Ala Phe Arg Arg Asp Leu Asp Ile His Thr Lys Thr Ala Met Asp Ile
385                 390                 395                 400
Phe His Val Ser Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
            420                 425                 430
Ala Gln Asn Leu Asn Ile Thr Arg Lys Glu Ala Ala Glu Phe Ile Glu
        435                 440                 445
Arg Tyr Phe Ala Ser Phe Pro Gly Val Lys Arg Tyr Met Glu Asn Ile
    450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
                485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Leu Ala Ala Arg Leu Lys Glu
        515                 520                 525
Glu Arg Leu Gln Ala Arg Leu Leu Gln Val His Asp Glu Leu Ile
    530                 535                 540
Leu Glu Ala Pro Lys Glu Glu Met Glu Arg Leu Cys Lys Leu Val Pro
545                 550                 555                 560
Glu Val Met Glu Gln Ala Val Glu Leu Arg Val Pro Leu Lys Val Asp
                565                 570                 575
```

```
Tyr His Tyr Gly Pro Thr Trp Tyr Asp Ala Lys
            580                 585
```

<210> SEQ ID NO 38
<211> LENGTH: 587
<212> TYPE: PRT
<213> ORGANISM: Artificial Sequence
<220> FEATURE:
<223> OTHER INFORMATION: Synthetic construct

<400> SEQUENCE: 38

```
Ala Glu Gly Glu Lys Pro Leu Ala Glu Met Glu Phe Ala Ile Val Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Gln Pro Phe Ile Asp Glu Leu
                165                 170                 175

Arg Arg Asn Glu Gln Asp Glu Leu Leu Thr Lys Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Ser Glu Leu Ala Glu Gln Leu Gly Ala
    210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
        275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
                325                 330                 335

Ile Pro Ile Arg Leu Glu Glu Gly Arg Lys Ile Arg Gln Ala Phe Val
            340                 345                 350
```

```
Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Thr Arg Lys Glu Ala Glu Phe Ile Glu
            435                 440                 445

Arg Tyr Phe Ala Ser Phe Pro Gly Val Lys Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
                500                 505                 510

Asp Ile Ile Lys Lys Ala Met Ile Asp Leu Ala Ala Arg Leu Lys Glu
                515                 520                 525

Glu Arg Leu Gln Ala Arg Leu Leu Leu Gln Val His Asp Glu Leu Ile
            530                 535                 540

Leu Glu Ala Pro Lys Glu Glu Ile Glu Arg Leu Cys Gln Leu Val Pro
545                 550                 555                 560

Glu Val Met Glu Gln Ala Val Thr Leu Arg Val Pro Leu Lys Val Asp
                565                 570                 575

Tyr His Tyr Gly Pro Thr Trp Tyr Asp Ala Lys
                580                 585

<210> SEQ ID NO 39
<211> LENGTH: 587
<212> TYPE: PRT
<213> ORGANISM: Artificial Sequence
<220> FEATURE:
<223> OTHER INFORMATION: Synthetic construct

<400> SEQUENCE: 39

Ala Glu Glu Glu Lys Pro Leu Ala Glu Met Glu Phe Ala Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Thr Glu Thr Ala Leu Ala
        50                  55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
                100                 105                 110

Asn Pro Ala Gln Asp Ala Gly Asp Val Ala Ala Val Ala Lys Met Lys
            115                 120                 125
```

-continued

```
Gln Tyr Glu Ala Val Arg Ser Asp Glu Ala Val Tyr Gly Lys Gly Ala
    130                 135                 140

Lys Arg Ala Leu Pro Asp Glu Pro Thr Leu Ala Glu His Leu Val Arg
145                 150                 155                 160

Lys Ala Ala Ile Trp Ala Leu Glu Glu Pro Phe Leu Asp Glu Leu
                165                 170                 175

Arg Glu Asn Glu Gln Asp Glu Leu Leu Thr Glu Leu Glu Gln Pro Leu
                180                 185                 190

Ala Leu Ile Leu Ala Glu Met Glu Phe Thr Gly Val Lys Val Asp Thr
            195                 200                 205

Lys Arg Leu Glu Gln Met Gly Glu Glu Leu Ala Glu Gln Leu Lys Ala
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
    290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Thr Arg Lys Glu Ala Ala Glu Phe Ile Glu
            435                 440                 445

Arg Tyr Phe Ala Ser Phe Pro Gly Val Lys Arg Tyr Met Glu Asp Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Arg Leu Gln Ala Arg Leu Leu Gln Val His Asp Glu Leu Ile
    530                 535                 540

Leu Glu Ala Pro Lys Glu Glu Ile Glu Arg Leu Cys Lys Leu Val Pro
```

```
                    545                 550                 555                 560
            Glu Val Met Glu Gln Ala Val Glu Leu Arg Val Pro Leu Lys Val Asp
                                565                 570                 575
            Tyr His Tyr Gly Pro Thr Trp Tyr Asp Ala Lys
                                580                 585

<210> SEQ ID NO 40
<211> LENGTH: 587
<212> TYPE: PRT
<213> ORGANISM: Artificial Sequence
<220> FEATURE:
<223> OTHER INFORMATION: Synthetic construct

<400> SEQUENCE: 40

Ala Glu Asp Glu Lys Pro Leu Ala Met Glu Phe Ala Ile Ala Asp
1               5                   10                  15

Gly Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Ala Ala Tyr Leu Leu
                100                 105                 110

Asn Pro Ala Gln Asp Ala Gly Asp Val Ala Val Ala Lys Met Lys
                115                 120                 125

Gln Tyr Glu Ala Val Arg Ser Asp Glu Ala Val Tyr Gly Lys Gly Ala
            130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Ser Asn Glu Gln Asp Gln Leu Leu Thr Lys Leu Glu Gln Pro Leu
                180                 185                 190

Ala Ser Ile Leu Ala Glu Met Glu Phe Thr Gly Val Lys Val Asp Thr
            195                 200                 205

Lys Arg Leu Glu Gln Met Gly Ser Glu Leu Ala Glu Gln Leu Arg Ala
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
                260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val His Pro Asp Thr Gly Lys Val His Thr Met Phe Asn Gln Ala
305                 310                 315                 320

Leu Thr Gln Thr Gly Arg Leu Ser Ser Ala Glu Pro Asn Leu Gln Asn
```

```
            325                 330                 335
Ile Pro Ile Arg Leu Glu Glu Gly Arg Lys Ile Arg Gln Ala Phe Val
            340                 345                 350

Pro Ser Glu Pro Asp Trp Leu Ile Phe Ala Ala Asp Tyr Ser Gln Ile
            355                 360                 365

Glu Leu Arg Val Leu Ala His Ile Ala Asp Asp Asn Leu Ile Glu
    370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
            405                 410                 415

Lys Ala Val Asn Phe Gly Ile Val Tyr Gly Ile Ser Asp Tyr Gly Leu
            420                 425                 430

Ala Gln Asn Leu Asn Ile Thr Arg Lys Glu Ala Ala Glu Phe Ile Glu
            435                 440                 445

Arg Tyr Phe Ala Ser Phe Pro Gly Val Lys Gln Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
            515                 520                 525

Glu Arg Leu Gln Ala Arg Leu Leu Leu Gln Val His Asp Glu Leu Ile
            530                 535                 540

Leu Glu Ala Pro Lys Glu Glu Ile Glu Arg Leu Cys Gln Leu Val Pro
545                 550                 555                 560

Glu Val Met Glu Gln Ala Val Thr Leu Arg Val Pro Leu Lys Val Asp
            565                 570                 575

Tyr His Tyr Gly Pro Thr Trp Tyr Asp Ala Lys
            580                 585

<210> SEQ ID NO 41
<211> LENGTH: 587
<212> TYPE: PRT
<213> ORGANISM: Artificial Sequence
<220> FEATURE:
<223> OTHER INFORMATION: Synthetic construct

<400> SEQUENCE: 41

Ala Glu Glu Glu Lys Pro Leu Glu Glu Met Glu Phe Ala Ile Ala Asp
1               5                   10                  15

Glu Val Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Val Ala Leu Lys Trp Lys Gly Ile
            85                  90                  95

Glu Leu Arg Gly Val Ala Phe Asp Leu Leu Leu Ala Ala Tyr Leu Leu
```

-continued

```
            100                 105                 110
Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn Glu Gln Asp Glu Leu Leu Thr Glu Leu Glu Gln Pro Leu
            180                 185                 190

Ala Thr Ile Leu Ala Glu Met Glu Phe Thr Gly Val Lys Val Asp Thr
        195                 200                 205

Lys Arg Leu Glu Gln Met Gly Glu Leu Ala Glu Gln Leu Lys Glu
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
                260                 265                 270

Glu Lys Leu Ala Pro His His Glu Ile Val Glu Asn Ile Leu His Tyr
            275                 280                 285

Arg Gln Leu Gly Lys Leu Gln Ser Thr Tyr Ile Glu Gly Leu Leu Lys
        290                 295                 300

Val Val His Pro Asp Thr Gly Lys Val His Thr Met Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
                340                 345                 350

Pro Ser Glu Pro Asp Trp Leu Ile Phe Ala Ala Asp Tyr Ser Gln Ile
        355                 360                 365

Glu Leu Arg Val Leu Ala His Ile Ala Asp Asp Asn Leu Ile Glu
        370                 375                 380

Ala Phe Arg Arg Asp Leu Asp Ile His Thr Lys Thr Ala Met Asp Ile
385                 390                 395                 400

Phe His Val Ser Glu Glu Val Thr Ala Asn Met Arg Arg Gln Ala
                405                 410                 415

Lys Ala Val Asn Phe Gly Ile Val Tyr Gly Ile Ser Asp Tyr Gly Leu
                420                 425                 430

Ala Gln Asn Leu Asn Ile Thr Arg Lys Glu Ala Ala Glu Phe Ile Glu
            435                 440                 445

Arg Tyr Phe Glu Ser Phe Pro Gly Val Lys Arg Tyr Met Glu Asn Ile
        450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525
```

```
Glu Arg Leu Gln Ala Arg Leu Leu Gln Val His Asp Glu Leu Ile
        530                 535                 540

Leu Glu Ala Pro Lys Glu Ile Glu Arg Leu Cys Gln Leu Val Pro
545                 550                 555                 560

Glu Val Met Glu Gln Ala Val Glu Leu Arg Val Pro Leu Lys Val Asp
                565                 570                 575

Tyr His Tyr Gly Pro Thr Trp Tyr Asp Ala Lys
                580                 585

<210> SEQ ID NO 42
<211> LENGTH: 587
<212> TYPE: PRT
<213> ORGANISM: Artificial Sequence
<220> FEATURE:
<223> OTHER INFORMATION: Synthetic construct

<400> SEQUENCE: 42

Glu Glu Glu Glu Pro Leu Glu Asp Ile Ser Phe Glu Ile Val Glu
1               5                   10                  15

Glu Val Thr Glu Asp Met Leu Thr Asp Glu Ser Ala Leu Val Val Glu
                20                  25                  30

Val Leu Glu Glu Asn Tyr His Lys Ala Asp Ile Val Gly Phe Ala Ile
            35                  40                  45

Ala Asn Glu Asn Gly Asn Phe Phe Ile Pro Thr Asp Thr Ala Leu Ala
50                  55                  60

Ser Glu Ala Phe Lys Lys Trp Leu Glu Asp Glu Thr Lys Lys Lys Ser
65                  70                  75                  80

Val Phe Asp Ala Lys Arg Ala Ile Val Ala Leu Lys Trp His Gly Ile
                85                  90                  95

Glu Leu Lys Gly Val Asp Phe Asp Leu Leu Ile Ala Ser Tyr Leu Leu
            100                 105                 110

Asn Pro Ser Glu Ser Ser Asp Asp Phe Ala Ser Val Ala Lys Thr Lys
        115                 120                 125

Gly Tyr Asn Ala Val Gln Ser Asp Glu Ala Val Tyr Gly Lys Gly Ala
    130                 135                 140

Lys Arg Ala Val Pro Asp Glu Glu Lys Leu Ala Glu His Leu Ala Arg
145                 150                 155                 160

Lys Ala Ala Ala Ile Ser Ala Leu Lys Glu Thr Phe Ile His Glu Leu
                165                 170                 175

Lys Glu Asn Glu Gln Tyr Glu Leu Phe Thr Asp Leu Glu Met Pro Leu
            180                 185                 190

Ala Leu Ile Leu Ala Asp Met Glu Tyr Thr Gly Val Lys Val Asp Val
        195                 200                 205

Glu Arg Leu Lys Glu Met Gly Glu Glu Leu Thr Glu Arg Leu Lys Glu
    210                 215                 220

Ile Glu Gln Lys Ile Tyr Glu Leu Ala Gly Gln Glu Phe Asn Ile Asn
225                 230                 235                 240

Ser Pro Lys Gln Leu Gly Val Ile Leu Phe Glu Lys Leu Gly Leu Pro
                245                 250                 255

Val Ile Lys Lys Thr Lys Thr Gly Tyr Ser Thr Ser Ala Asp Val Leu
            260                 265                 270

Glu Lys Leu Ala Ser His His Glu Ile Ile Arg His Ile Leu His Tyr
        275                 280                 285

Arg Gln Leu Gly Lys Leu Gln Ser Thr Tyr Ile Glu Gly Leu Leu Lys
    290                 295                 300
```

```
Val Val His Glu Asp Thr Gly Lys Val His Thr Arg Phe Asn Gln Ala
305                 310                 315                 320

Leu Thr Gln Thr Gly Arg Leu Ser Ser Thr Asp Pro Asn Leu Gln Asn
            325                 330                 335

Ile Pro Ile Arg Leu Glu Glu Gly Arg Lys Ile Arg Gln Ala Phe Val
            340                 345                 350

Pro Ser Glu Pro Gly Trp Val Ile Phe Ala Ala Asp Tyr Ser Gln Ile
            355                 360                 365

Glu Leu Arg Val Leu Ala His Ile Ala Asn Asp Glu Asn Leu Ile Glu
370                 375                 380

Ala Phe Arg His Asp Met Asp Ile His Thr Lys Thr Ala Met Asp Val
385                 390                 395                 400

Phe His Val Ser Glu Asp Glu Val Thr Ser Asn Met Arg Arg Gln Ala
            405                 410                 415

Lys Ala Val Asn Phe Gly Ile Val Tyr Gly Ile Ser Asp Tyr Gly Leu
            420                 425                 430

Ser Gln Asn Leu Gly Ile Thr Arg Lys Glu Ala Gly Glu Phe Ile Glu
            435                 440                 445

Arg Tyr Leu Glu Ser Phe Pro Gly Val Lys Glu Tyr Met Asp Asp Ile
450                 455                 460

Val Gln Glu Ala Lys Gln Lys Gly Tyr Val Thr Thr Leu Leu His Arg
465                 470                 475                 480

Arg Arg Tyr Leu Pro Glu Ile Thr Ser Arg Asn Phe Asn Leu Arg Ser
            485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Met Ala Asp Arg Leu Lys Glu
            515                 520                 525

Glu Asn Leu Gln Ala Arg Leu Leu Leu Gln Val His Asp Glu Leu Ile
530                 535                 540

Phe Glu Ala Pro Lys Glu Glu Ile Glu Lys Leu Lys Lys Ile Val Pro
545                 550                 555                 560

Glu Val Met Glu Asn Ala Val Glu Leu Lys Val Pro Leu Lys Val Asp
            565                 570                 575

Tyr Ser Tyr Gly Pro Thr Trp Tyr Asp Ala Lys
            580                 585

<210> SEQ ID NO 43
<211> LENGTH: 408
<212> TYPE: PRT
<213> ORGANISM: Artificial Sequence
<220> FEATURE:
<223> OTHER INFORMATION: Synthetic construct

<400> SEQUENCE: 43

Glu Gln Asp Arg Leu Leu Thr Glu Leu Glu Gln Pro Leu Ala Ser Ile
1               5                   10                  15

Leu Ala Glu Met Glu Phe Thr Gly Val Asn Val Asp Thr Lys Arg Leu
            20                  25                  30

Glu Gln Met Gly Ser Glu Leu Ala Glu Gln Leu Lys Glu Gln Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80
```

```
Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
    130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Gln
        195                 200                 205

Arg Asp Leu Asp Ile His Thr Lys Thr Ala Met Asp Ile Phe His Val
    210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Glu Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Gln Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Lys Leu Val Pro Glu Val Met
    370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 44
<211> LENGTH: 408
<212> TYPE: PRT
<213> ORGANISM: Artificial Sequence
<220> FEATURE:
<223> OTHER INFORMATION: Synthetic construct

<400> SEQUENCE: 44

Glu Gln Tyr Glu Leu Leu Thr Glu Leu Glu Met Pro Leu Ala Leu Ile
1               5                   10                  15

Leu Ala Asp Met Glu Tyr Thr Gly Val Lys Val Asp Val Glu Arg Leu
            20                  25                  30
```

```
Lys Glu Met Gly Glu Glu Leu Thr Glu Arg Leu Lys Glu Ile Glu Gln
         35                  40                  45

Lys Ile Tyr Glu Leu Ala Gly Gln Glu Phe Asn Ile Asn Ser Pro Lys
 50                  55                  60

Gln Leu Gly Val Ile Leu Phe Glu Lys Leu Gly Leu Pro Val Ile Lys
 65                  70                  75                  80

Lys Thr Lys Thr Gly Tyr Ser Thr Ser Ala Asp Val Leu Glu Lys Leu
                     85                  90                  95

Ala Ser His His Glu Ile Ile Arg His Ile Leu His Tyr Arg Gln Leu
                100                 105                 110

Gly Lys Leu Gln Ser Thr Tyr Ile Glu Gly Leu Leu Lys Val Val His
            115                 120                 125

Pro Asp Thr Gly Lys Val His Thr Arg Phe Asn Gln Ala Leu Thr Gln
130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Gly Trp Val Ile Phe Ala Ala Asp Tyr Ser Gln Ile Glu Leu Arg
            180                 185                 190

Val Leu Ala His Ile Ala Asn Asp Glu Asn Leu Ile Glu Ala Phe Arg
            195                 200                 205

His Asp Met Asp Ile His Thr Lys Thr Ala Met Asp Val Phe His Val
210                 215                 220

Ser Glu Asp Glu Val Thr Ser Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Gly Glu Phe Ile Glu Arg Tyr Leu
            260                 265                 270

Glu Ser Phe Pro Gly Val Lys Glu Tyr Met Asp Asp Ile Val Gln Glu
            275                 280                 285

Ala Lys Gln Lys Gly Tyr Val Thr Thr Leu Leu His Arg Arg Arg Tyr
290                 295                 300

Leu Pro Glu Ile Thr Ser Arg Asn Phe Asn Leu Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Asp Arg Leu Lys Glu Glu Asn Leu
            340                 345                 350

Gln Ala Arg Leu Leu Leu Gln Val His Asp Glu Leu Ile Phe Glu Ala
            355                 360                 365

Pro Lys Glu Glu Ile Glu Lys Leu Cys Lys Leu Val Pro Glu Val Met
370                 375                 380

Glu Asn Ala Val Glu Leu Lys Val Pro Leu Lys Val Asp Tyr Ser Tyr
385                 390                 395                 400

Gly Pro Thr Trp Tyr Asp Ala Lys
                405

<210> SEQ ID NO 45
<211> LENGTH: 408
<212> TYPE: PRT
<213> ORGANISM: Artificial Sequence
<220> FEATURE:
```

<223> OTHER INFORMATION: Synthetic construct

<400> SEQUENCE: 45

```
Glu Gln Asp Glu Leu Phe Thr Lys Leu Gln Pro Leu Ala Thr Ile
1               5                   10                  15

Leu Ala Glu Met Glu Phe Thr Gly Val Lys Val Asp Thr Lys Arg Leu
                20                  25                  30

Glu Gln Met Gly Ser Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
                100                 105                 110

Gly Lys Leu Gln Ser Thr Tyr Ile Glu Gly Leu Leu Lys Val Val His
            115                 120                 125

Pro Asp Thr Gly Lys Val His Thr Arg Phe Asn Gln Ala Leu Thr Gln
130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Glu Asn Leu Ile Glu Ala Phe Arg
        195                 200                 205

Arg Asp Leu Asp Ile His Thr Lys Thr Ala Met Asp Ile Phe His Val
210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Lys Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Gln Leu Val Pro Glu Val Met
370                 375                 380

Glu Gln Ala Val Arg Leu Arg Val Pro Leu Lys Val Asp Tyr His Tyr
385                 390                 395                 400
```

```
Gly Pro Thr Trp Tyr Asp Ala Lys
            405
```

<210> SEQ ID NO 46
<211> LENGTH: 408
<212> TYPE: PRT
<213> ORGANISM: Artificial Sequence
<220> FEATURE:
<223> OTHER INFORMATION: Synthetic construct

<400> SEQUENCE: 46

```
Glu Gln Asp Glu Leu Thr Glu Leu Gln Pro Leu Ala Leu Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His Arg Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Gln Ser Phe Pro Gly Val Lys Arg Tyr Met Glu Asp Ile Val Gln Glu
        275                 280                 285

Ala Lys Gln Lys Gly Tyr Val Thr Thr Leu Leu His Arg Arg Arg Tyr
        290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350
```

```
Gln Ala Arg Leu Leu Gln Val His Asp Glu Leu Ile Leu Glu Ala
            355                 360                 365
Pro Lys Glu Glu Ile Glu Arg Leu Cys Lys Leu Val Pro Glu Val Met
370                 375                 380
Glu Gln Ala Val Glu Leu Arg Val Pro Leu Lys Val Asp Tyr Arg Tyr
385                 390                 395                 400
Gly Pro Thr Trp Tyr Asp Ala Lys
                405

<210> SEQ ID NO 47
<211> LENGTH: 408
<212> TYPE: PRT
<213> ORGANISM: Artificial Sequence
<220> FEATURE:
<223> OTHER INFORMATION: Synthetic construct

<400> SEQUENCE: 47

Glu Gln Asp Glu Leu Phe Thr Glu Leu Glu Leu Pro Leu Ala Leu Ile
1               5                   10                  15
Leu Ala Glu Met Glu Phe Thr Gly Val Lys Val Asp Thr Lys Arg Leu
                20                  25                  30
Glu Gln Met Gly Glu Glu Leu Ala Glu Gln Leu Lys Glu Val Glu Gln
            35                  40                  45
Arg Ile Tyr Glu Leu Ala Gly Gln Glu Phe Asn Ile Asn Ser Pro Lys
    50                  55                  60
Gln Leu Gly Val Ile Leu Phe Glu Lys Leu Gln Leu Pro Val Leu Lys
65                  70                  75                  80
Lys Thr Lys Thr Gly Tyr Ser Thr Ser Ala Asp Val Leu Glu Lys Leu
                85                  90                  95
Ala Pro His His Glu Ile Val Glu Asn Ile Leu His Tyr Arg Gln Leu
            100                 105                 110
Gly Lys Leu Gln Ser Thr Tyr Ile Glu Gly Leu Leu Lys Val Val His
        115                 120                 125
Pro Asp Thr Gly Lys Val His Thr Arg Phe Asn Gln Ala Leu Thr Gln
    130                 135                 140
Thr Gly Arg Leu Ser Ser Thr Asp Pro Asn Leu Gln Asn Ile Pro Ile
145                 150                 155                 160
Arg Leu Glu Glu Gly Arg Lys Ile Arg Gln Ala Phe Val Pro Ser Glu
                165                 170                 175
Pro Asp Trp Leu Ile Phe Ala Ala Asp Tyr Ser Gln Ile Glu Leu Arg
            180                 185                 190
Val Leu Ala His Ile Ala Asn Asp Asp Asn Leu Ile Glu Ala Phe Arg
        195                 200                 205
Arg Asp Met Asp Ile His Thr Lys Thr Ala Met Asp Val Phe His Val
    210                 215                 220
Ser Glu Asp Glu Val Thr Ser Asn Met Arg Arg Gln Ala Lys Ala Val
225                 230                 235                 240
Asn Phe Gly Ile Val Tyr Gly Ile Ser Asp Tyr Gly Leu Ser Gln Asn
                245                 250                 255
Leu Gly Ile Thr Arg Lys Glu Ala Ala Glu Phe Ile Glu Arg Tyr Phe
            260                 265                 270
Glu Ser Phe Pro Gly Val Lys Glu Tyr Met Glu Asp Ile Val Gln Glu
        275                 280                 285
Ala Lys Gln Lys Gly Tyr Val Thr Thr Leu Leu His Arg Arg Arg Tyr
    290                 295                 300
```

```
Leu Pro Glu Ile Thr Ser Arg Asn Phe Asn Leu Arg Ser Phe Ala Glu
305                 310                 315                 320

Arg Thr Ala Met Asn Thr Pro Ile Gln Gly Ser Ala Ala Asp Ile Ile
            325                 330                 335

Lys Lys Ala Met Ile Asp Met Ala Ala Arg Leu Lys Glu Glu Arg Leu
            340                 345                 350

Gln Ala Arg Leu Leu Leu Gln Val His Asp Glu Leu Ile Phe Glu Ala
            355                 360                 365

Pro Lys Glu Glu Ile Glu Arg Leu Glu Lys Leu Val Pro Glu Val Met
            370                 375                 380

Glu His Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 48
<211> LENGTH: 408
<212> TYPE: PRT
<213> ORGANISM: Artificial Sequence
<220> FEATURE:
<223> OTHER INFORMATION: Synthetic construct

<400> SEQUENCE: 48

Glu Gln Asp Arg Leu Leu Thr Glu Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Arg Ala Val Glu Gln
        35                  40                  45

Arg Ile Tyr Glu Leu Ala Gly Gln Glu Phe Asn Ile Asn Ser Pro Lys
50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asn Asp Asp Asn Leu Ile Glu Ala Phe Arg
        195                 200                 205

Arg Asp Leu Asp Ile His Thr Lys Thr Ala Met Asp Val Phe His Val
210                 215                 220

Ser Glu Glu Glu Val Thr Ala Arg Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255
```

```
Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Tyr
        290                 295                 300

Leu Pro Asp Ile Thr Ser Arg Asn Phe Asn Val Arg Ser Phe Ala Glu
305                 310                 315                 320

Arg Met Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
                355                 360                 365

Pro Lys Glu Glu Ile Glu Arg Leu Cys Gln Leu Val Pro Glu Val Met
        370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 49
<211> LENGTH: 408
<212> TYPE: PRT
<213> ORGANISM: Artificial Sequence
<220> FEATURE:
<223> OTHER INFORMATION: Synthetic construct

<400> SEQUENCE: 49

Glu Gln Asp Gln Leu Leu Thr Glu Leu Glu Gln Pro Leu Ala Ala Ile
1               5                   10                  15

Leu Ala Glu Met Glu Phe Thr Gly Val Asn Val Asp Thr Lys Arg Leu
            20                  25                  30

Glu Gln Met Gly Ser Glu Leu Ala Glu Gln Leu Lys Glu Ile Glu Gln
        35                  40                  45

Arg Ile Tyr Glu Leu Ala Gly Gln Glu Phe Asn Ile Asn Ser Pro Lys
 50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Gln
        195                 200                 205
```

Arg Asp Leu Asp Ile His Thr Lys Thr Ala Met Asp Ile Phe His Val
210                215                220

Ser Glu Glu Val Thr Ala Asn Met Arg Arg Gln Ala Lys Ala Val
225                230                235                240

Asn Phe Gly Ile Val Tyr Gly Ile Ser Asp Tyr Gly Leu Ala Gln Asn
            245                250                255

Leu Asn Ile Thr Arg Lys Glu Ala Ala Glu Phe Ile Glu Arg Tyr Phe
            260                265                270

Ala Ser Phe Pro Gly Val Lys Gln Tyr Met Glu Asn Ile Val Gln Glu
            275                280                285

Ala Lys Gln Lys Gly Tyr Val Thr Thr Leu Leu His Arg Arg Arg Tyr
290                295                300

Leu Pro Asp Ile Thr Ser Arg Asn Phe Asn Val Arg Ser Phe Ala Glu
305                310                315                320

Arg Thr Ala Met Asn Thr Pro Ile Gln Gly Ser Ala Ala Asp Ile Ile
            325                330                335

Lys Lys Ala Met Ile Asp Leu Ala Ala Arg Leu Lys Glu Glu Gln Leu
            340                345                350

Gln Ala Arg Leu Leu Leu Gln Val His Asp Glu Leu Ile Leu Glu Ala
355                360                365

Pro Lys Glu Glu Ile Glu Arg Leu Cys Lys Leu Val Pro Glu Val Met
370                375                380

Glu Gln Ala Val Glu Leu Arg Val Pro Leu Lys Val Asp Tyr His Tyr
385                390                395                400

Gly Pro Thr Trp Tyr Asp Ala Lys
            405

<210> SEQ ID NO 50
<211> LENGTH: 408
<212> TYPE: PRT
<213> ORGANISM: Artificial Sequence
<220> FEATURE:
<223> OTHER INFORMATION: Synthetic construct

<400> SEQUENCE: 50

Glu Gln Asp Glu Leu Leu Thr Glu Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
            85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
            115                 120                 125

Pro Asp Thr Gly Lys Val His Thr Arg Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

```
Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Lys Leu Val Pro Glu Val Met
    370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 51
<211> LENGTH: 408
<212> TYPE: PRT
<213> ORGANISM: Artificial Sequence
<220> FEATURE:
<223> OTHER INFORMATION: Synthetic construct

<400> SEQUENCE: 51

Glu Gln Asp Gln Leu Leu Thr Lys Leu Glu Gln Pro Leu Ala Ser Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Arg Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110
```

```
Gly Lys Leu Gln Ser Thr Tyr Ile Glu Gly Leu Leu Lys Val Val His
            115                 120                 125

Pro Asp Thr Gly Lys Val His Thr Met Phe Asn Gln Ala Leu Thr Gln
130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
            195                 200                 205

Arg Asp Leu Asp Ile His Thr Lys Thr Ala Met Asp Ile Phe His Val
            210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Gln Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Gln Leu Val Pro Glu Val Met
370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 52
<211> LENGTH: 408
<212> TYPE: PRT
<213> ORGANISM: Artificial Sequence
<220> FEATURE:
<223> OTHER INFORMATION: Synthetic construct

<400> SEQUENCE: 52

Glu Gln Asp Glu Leu Leu Thr Glu Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Lys Glu Val Glu Gln
        35                  40                  45

Arg Ile Tyr Glu Leu Ala Gly Gln Glu Phe Asn Ile Asn Ser Pro Lys
    50                  55                  60
```

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
            85                  90                  95

Ala Pro His His Glu Ile Val Glu Asn Ile Leu His Tyr Arg Gln Leu
        100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
    130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Glu Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Gln Leu Val Pro Glu Val Met
    370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 53
<211> LENGTH: 408
<212> TYPE: PRT
<213> ORGANISM: Artificial Sequence
<220> FEATURE:
<223> OTHER INFORMATION: Synthetic construct

<400> SEQUENCE: 53

Glu Gln Asp Arg Leu Leu Thr Glu Leu Glu Gln Pro Leu Ala Thr Ile
1               5                   10                  15

```
Leu Ala Glu Met Glu Phe Thr Gly Val Lys Val Asp Thr Lys Arg Leu
            20                  25                  30

Glu Gln Met Gly Ser Glu Leu Ala Glu Gln Leu Lys Glu Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
    130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Met Glu Arg Leu Cys Lys Leu Val Pro Glu Val Met
    370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 54
<211> LENGTH: 408
<212> TYPE: PRT
```

<213> ORGANISM: Artificial Sequence
<220> FEATURE:
<223> OTHER INFORMATION: Synthetic construct

<400> SEQUENCE: 54

```
Asp Gln Tyr Glu Leu Leu Thr Glu Leu Glu Met Pro Leu Ala Leu Ile
1               5                   10                  15

Leu Gly Glu Met Glu Ser Thr Gly Val Lys Val Asp Val Glu Arg Leu
            20                  25                  30

Lys Arg Met Gly Glu Glu Leu Thr Glu Lys Leu Lys Glu Tyr Glu Glu
        35                  40                  45

Lys Ile His Glu Leu Ala Gly Glu Pro Phe Asn Ile Asn Ser Pro Lys
    50                  55                  60

Gln Leu Gly Val Ile Leu Phe Glu Lys Leu Gly Leu Pro Val Ile Lys
65                  70                  75                  80

Lys Thr Lys Thr Gly Tyr Ser Thr Ser Ala Asp Val Leu Glu Lys Leu
                85                  90                  95

Ala Asp Lys His Glu Ile Ile Arg Tyr Ile Leu His Tyr Arg Gln Ile
            100                 105                 110

Gly Lys Leu Gln Ser Thr Tyr Ile Glu Gly Leu Leu Lys Val Thr Arg
        115                 120                 125

Lys Asp Thr His Lys Val His Thr Arg Phe Asn Gln Ala Leu Thr Gln
130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Glu Gly Trp Leu Ile Phe Ala Ala Asp Tyr Ser Gln Ile Glu Leu Arg
            180                 185                 190

Val Leu Ala His Ile Ser Lys Asp Glu Asn Leu Ile Glu Ala Phe Thr
        195                 200                 205

His Asp Met Asp Ile His Thr Lys Thr Ala Met Asp Val Phe His Val
    210                 215                 220

Ser Glu Asp Glu Val Thr Ser Ala Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Gly Ala Phe Ile Glu Arg Tyr Leu
            260                 265                 270

Glu Ser Phe Pro Gly Val Lys Ala Tyr Met Glu Asp Ile Val Gln Glu
        275                 280                 285

Ala Lys Gln Lys Gly Tyr Val Thr Thr Leu Leu His Arg Arg Arg Tyr
    290                 295                 300

Ile Pro Glu Ile Thr Ser Arg Asn Phe Asn Ile Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Ala Arg Leu Lys Glu Glu Asn Leu
            340                 345                 350

Gln Ala Arg Leu Leu Leu Gln Val His Asp Glu Leu Ile Phe Glu Ala
        355                 360                 365

Pro Lys Glu Glu Ile Glu Ile Leu Cys Lys Leu Val Pro Glu Val Met
    370                 375                 380

Glu His Ala Val Glu Leu Asp Val Pro Leu Lys Val Asp Tyr Ala Ser
```

Gly Pro Ser Trp Tyr Asp Ala Lys
            405

<210> SEQ ID NO 55
<211> LENGTH: 408
<212> TYPE: PRT
<213> ORGANISM: Artificial Sequence
<220> FEATURE:
<223> OTHER INFORMATION: Synthetic construct

<400> SEQUENCE: 55

Glu Gln Tyr Glu Leu Leu Thr Glu Leu Glu Met Pro Leu Ala Leu Ile
1               5                   10                  15

Leu Ala Asp Met Glu Tyr Thr Gly Val Lys Val Asp Val Glu Arg Leu
            20                  25                  30

Lys Glu Met Gly Glu Glu Leu Ala Glu Arg Leu Lys Glu Ile Glu Gln
        35                  40                  45

Lys Ile Tyr Glu Leu Ala Gly Glu Glu Phe Asn Ile Asn Ser Pro Lys
    50                  55                  60

Gln Leu Gly Val Ile Leu Phe Glu Lys Leu Gly Leu Pro Val Ile Lys
65                  70                  75                  80

Lys Thr Lys Thr Gly Tyr Ser Thr Ser Ala Asp Val Leu Glu Lys Leu
                85                  90                  95

Ala Ser Lys His Glu Ile Ile Arg Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
    130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Glu Gly Trp Val Ile Phe Ala Ala Asp Tyr Ser Gln Ile Glu Leu Arg
            180                 185                 190

Val Leu Ala His Ile Ala Asn Asp Glu Lys Leu Ile Glu Ala Phe Arg
        195                 200                 205

His Asp Met Asp Ile His Thr Lys Thr Ala Met Asp Val Phe His Val
    210                 215                 220

Ser Glu Asp Glu Val Thr Ser Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Ala Glu Phe Ile Glu Arg Tyr Leu
            260                 265                 270

Glu Ser Phe Pro Gly Val Lys Gln Tyr Met Asp Asp Ile Val Gln Glu
        275                 280                 285

Ala Lys Gln Lys Gly Tyr Val Thr Thr Leu Leu His Arg Arg Arg Tyr
    290                 295                 300

Leu Pro Glu Ile Thr Ser Arg Asn Phe Asn Leu Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Asn Arg Leu Lys Glu Glu Asn Leu

```
              340                 345                 350
Gln Ala Arg Leu Leu Gln Val His Asp Glu Leu Ile Phe Glu Ala
            355                 360                 365
Pro Lys Glu Glu Ile Glu Lys Cys Lys Lys Ile Val Pro Glu Val Met
        370                 375                 380
Glu His Ala Val Glu Leu Lys Val Pro Leu Lys Val Asp Tyr Ser Tyr
385                 390                 395                 400
Gly Pro Thr Trp Tyr Asp Ala Lys
                405

<210> SEQ ID NO 56
<211> LENGTH: 408
<212> TYPE: PRT
<213> ORGANISM: Artificial Sequence
<220> FEATURE:
<223> OTHER INFORMATION: Synthetic construct

<400> SEQUENCE: 56

Glu Gln Asp Arg Leu Leu Thr Glu Leu Glu Gln Pro Leu Ala Ser Ile
1               5                   10                  15
Leu Ala Glu Met Glu Phe Thr Gly Val Lys Val Asp Thr Lys Arg Leu
            20                  25                  30
Glu Gln Met Gly Glu Glu Leu Thr Glu Gln Leu Lys Glu Val Glu Gln
        35                  40                  45
Arg Ile Tyr Glu Leu Ala Gly Gln Glu Phe Asn Ile Asn Ser Pro Lys
    50                  55                  60
Gln Leu Gly Val Ile Leu Phe Glu Lys Leu Gln Leu Pro Val Leu Lys
65                  70                  75                  80
Lys Thr Lys Thr Gly Tyr Ser Thr Ser Ala Asp Val Leu Glu Lys Leu
                85                  90                  95
Ala Pro His His Glu Ile Val Glu Asn Ile Leu His Tyr Arg Gln Leu
            100                 105                 110
Gly Lys Leu Gln Ser Thr Tyr Ile Glu Gly Leu Leu Lys Val Val His
        115                 120                 125
Pro Asp Thr Gly Lys Val His Thr Arg Phe Asn Gln Ala Leu Thr Gln
    130                 135                 140
Thr Gly Arg Leu Ser Ser Thr Glu Pro Asn Leu Gln Asn Ile Pro Ile
145                 150                 155                 160
Arg Leu Glu Glu Gly Arg Lys Ile Arg Gln Ala Phe Val Pro Ser Glu
                165                 170                 175
Pro Asp Trp Leu Ile Phe Ala Ala Asp Tyr Ser Gln Ile Glu Leu Arg
            180                 185                 190
Val Leu Ala His Ile Ala Asp Asp Asn Leu Ile Glu Ala Phe Arg
        195                 200                 205
Arg Asp Leu Asp Ile His Thr Lys Thr Ala Met Asp Ile Phe His Val
    210                 215                 220
Ser Glu Glu Glu Val Thr Ala Asn Met Arg Arg Gln Ala Lys Ala Val
225                 230                 235                 240
Asn Phe Gly Ile Val Tyr Gly Ile Ser Asp Tyr Gly Leu Ala Gln Asn
                245                 250                 255
Leu Asn Ile Thr Arg Lys Glu Ala Ala Glu Phe Ile Glu Arg Tyr Phe
            260                 265                 270
Ala Ser Phe Pro Gly Val Lys Gln Tyr Met Glu Asn Ile Val Gln Glu
        275                 280                 285
Ala Lys Gln Lys Gly Tyr Val Thr Thr Leu Leu His Arg Arg Arg Tyr
```

```
                     290                 295                 300
Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Gln Val His Asp Glu Leu Ile Leu Glu Ala
            355                 360                 365

Pro Lys Glu Glu Ile Glu Arg Leu Cys Lys Leu Val Pro Glu Val Met
        370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 57
<211> LENGTH: 408
<212> TYPE: PRT
<213> ORGANISM: Artificial Sequence
<220> FEATURE:
<223> OTHER INFORMATION: Synthetic construct

<400> SEQUENCE: 57

Glu Gln Asp Arg Leu Leu Val Glu Leu Glu Met Pro Leu Ser Ser Ile
1               5                   10                  15

Leu Ala Glu Met Glu Phe Ala Gly Val Lys Val Asp Thr Lys Arg Leu
                20                  25                  30

Glu Gln Met Gly Glu Glu Leu Ala Glu Gln Leu Arg Thr Val Glu Gln
            35                  40                  45

Arg Ile Tyr Glu Leu Ala Gly Gln Glu Phe Asn Ile Asn Ser Pro Lys
        50                  55                  60

Gln Leu Gly Leu Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro Tyr His Glu Ile Val Glu Asn Ile Leu His Tyr Arg Gln Leu
                100                 105                 110

Gly Lys Leu Gln Ser Thr Tyr Ile Glu Gly Leu Leu Lys Val Val His
            115                 120                 125

Pro Asp Thr Lys Lys Val His Thr Ile Phe Asn Gln Ala Leu Thr Gln
        130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Ser Asp Trp Leu Ile Phe Ala Ala Asp Tyr Ser Gln Ile Glu Leu Arg
                180                 185                 190

Val Leu Ala His Ile Ala Glu Asp Asp Asn Leu Met Glu Ala Phe Arg
            195                 200                 205

Arg Asp Leu Asp Ile His Thr Lys Thr Ala Met Asp Val Phe Gln Val
        210                 215                 220

Ser Glu Asp Glu Val Thr Pro Arg Met Arg Arg Gln Ala Lys Ala Val
225                 230                 235                 240

Asn Phe Gly Ile Val Tyr Gly Ile Ser Asp Tyr Gly Leu Ser Gln Asn
```

```
                        245                 250                 255
Leu Gly Ile Ser Arg Lys Glu Ala Ala Glu Phe Ile Glu Arg Tyr Phe
                260                 265                 270
Glu Ser Phe Pro Gly Val Lys Arg Tyr Met Glu Asn Ile Val Gln Glu
            275                 280                 285
Ala Lys Gln Lys Gly Tyr Val Thr Thr Leu Leu His Arg Arg Arg Tyr
        290                 295                 300
Leu Pro Asp Ile Thr Ser Arg Asn Phe Asn Val Arg Ser Phe Ala Glu
305                 310                 315                 320
Arg Met Ala Met Asn Thr Pro Ile Gln Gly Ser Ala Ala Asp Ile Ile
                325                 330                 335
Lys Lys Ala Met Ile Asp Leu Asn Ala Arg Leu Lys Glu Glu Arg Leu
                340                 345                 350
Gln Ala Arg Leu Leu Gln Val His Asp Glu Leu Ile Leu Glu Ala
            355                 360                 365
Pro Lys Glu Glu Met Glu Arg Leu Cys Arg Leu Val Pro Glu Val Met
        370                 375                 380
Glu Gln Ala Val Thr Leu Arg Val Pro Leu Lys Val Asp Tyr His Tyr
385                 390                 395                 400
Gly Ser Thr Trp Tyr Asp Ala Lys
                405

<210> SEQ ID NO 58
<211> LENGTH: 408
<212> TYPE: PRT
<213> ORGANISM: Artificial Sequence
<220> FEATURE:
<223> OTHER INFORMATION: Synthetic construct

<400> SEQUENCE: 58

Glu Gln Asp Glu Leu Leu Thr Glu Leu Glu Gln Pro Leu Ala Leu Ile
1               5                   10                  15
Leu Ala Glu Met Glu Phe Thr Gly Val Lys Val Asp Thr Lys Arg Leu
            20                  25                  30
Glu Gln Met Gly Glu Glu Leu Ala Glu Gln Leu Lys Glu Val Glu Gln
        35                  40                  45
Arg Ile Tyr Glu Leu Ala Gly Gln Glu Phe Asn Ile Asn Ser Pro Lys
    50                  55                  60
Gln Leu Gly Val Ile Leu Phe Glu Lys Leu Gln Leu Pro Val Leu Lys
65                  70                  75                  80
Lys Thr Lys Thr Gly Tyr Ser Thr Ser Ala Asp Val Leu Glu Lys Leu
                85                  90                  95
Ala Pro His His Glu Ile Val Glu Asn Ile Leu His Tyr Arg Gln Leu
            100                 105                 110
Gly Lys Leu Gln Ser Thr Tyr Ile Glu Gly Leu Leu Lys Val Val His
        115                 120                 125
Pro Asp Thr Gly Lys Val His Thr Met Phe Asn Gln Ala Leu Thr Gln
    130                 135                 140
Thr Gly Arg Leu Ser Ser Ala Glu Pro Asn Leu Gln Asn Ile Pro Ile
145                 150                 155                 160
Arg Leu Glu Glu Gly Arg Lys Ile Arg Gln Ala Phe Val Pro Ser Glu
                165                 170                 175
Pro Asp Trp Leu Ile Phe Ala Ala Asp Tyr Ser Gln Ile Glu Leu Arg
            180                 185                 190
Val Leu Ala His Ile Ala Asp Asp Asp Asn Leu Ile Glu Ala Phe Arg
```

```
                195                 200                 205
Arg Asp Leu Asp Ile His Thr Lys Thr Ala Met Asp Ile Phe His Val
210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
                260                 265                 270

Ala Ser Phe Pro Gly Val Lys Arg Tyr Met Glu Asn Ile Val Gln Glu
                275                 280                 285

Ala Lys Gln Lys Gly Tyr Val Thr Thr Leu Leu His Arg Arg Arg Tyr
                290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
                355                 360                 365

Pro Lys Glu Glu Ile Glu Arg Leu Cys Lys Leu Val Pro Glu Val Met
                370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 59
<211> LENGTH: 408
<212> TYPE: PRT
<213> ORGANISM: Artificial Sequence
<220> FEATURE:
<223> OTHER INFORMATION: Synthetic construct

<400> SEQUENCE: 59

Glu Gln Asp Glu Leu Leu Thr Asp Leu Glu Gln Pro Leu Ser Ser Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Arg Ala Val Glu Gln
                35                  40                  45

Arg Ile Tyr Glu Leu Ala Gly Gln Glu Phe Asn Ile Asn Ser Pro Lys
                50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
                100                 105                 110

Gly Lys Leu Gln Ser Thr Tyr Ile Glu Gly Leu Leu Lys Val Val His
                115                 120                 125

Pro Asp Thr Gly Lys Val His Thr Ile Phe Asn Gln Ala Leu Thr Gln
                130                 135                 140

Thr Gly Arg Leu Ser Ser Thr Glu Pro Asn Leu Gln Asn Ile Pro Ile
```

```
                    145                 150                 155                 160
Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
                180                 185                 190

Val Leu Ala His Ile Ala Asp Asp Asn Leu Ile Glu Ala Phe Arg
                195                 200                 205

Arg Asp Leu Asp Ile His Thr Lys Thr Ala Met Asp Ile Phe His Val
            210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                    245                 250                 255

Leu Asn Ile Thr Arg Lys Glu Ala Ala Glu Phe Ile Glu Arg Tyr Phe
                260                 265                 270

Glu Ser Phe Pro Gly Val Lys Arg Tyr Met Glu Asn Ile Val Gln Glu
                275                 280                 285

Ala Lys Gln Lys Gly Tyr Val Thr Thr Leu Leu His Arg Arg Arg Tyr
            290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                    325                 330                 335

Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Gln Leu Val Pro Glu Val Met
        370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                    405

<210> SEQ ID NO 60
<211> LENGTH: 408
<212> TYPE: PRT
<213> ORGANISM: Artificial Sequence
<220> FEATURE:
<223> OTHER INFORMATION: Synthetic construct

<400> SEQUENCE: 60

Glu Gln Asp Glu Leu Leu Ile Lys Leu Glu Gln Pro Leu Ala Thr Ile
1               5                   10                  15

Leu Ala Glu Met Glu Phe Thr Gly Val Lys Val Asp Thr Lys Arg Leu
                20                  25                  30

Glu Gln Met Gly Ser Glu Leu Ala Glu Gln Leu Arg Ala Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
```

```
            100                 105                 110
Gly Lys Leu Gln Ser Thr Tyr Ile Glu Gly Leu Leu Lys Val Val His
            115                 120                 125

Pro Asp Thr Gly Lys Val His Thr Met Phe Asn Gln Ala Leu Thr Gln
            130                 135             140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                    165                 170                 175

Pro Asp Trp Leu Ile Phe Ala Ala Asp Tyr Ser Gln Ile Glu Leu Arg
                180                 185                 190

Val Leu Ala His Ile Ala Asp Asp Asn Leu Ile Glu Ala Phe Arg
            195                 200                 205

Arg Asp Leu Asp Ile His Thr Lys Thr Ala Met Asp Ile Phe His Val
            210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
                260                 265                 270

Ala Ser Phe Pro Gly Val Lys Arg Tyr Met Glu Asn Ile Val Gln Glu
            275                 280                 285

Ala Lys Gln Lys Gly Tyr Val Thr Thr Leu Leu His Arg Arg Tyr
            290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Gln Leu Val Pro Glu Val Met
            370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 61
<211> LENGTH: 408
<212> TYPE: PRT
<213> ORGANISM: Artificial Sequence
<220> FEATURE:
<223> OTHER INFORMATION: Synthetic construct

<400> SEQUENCE: 61

Glu Gln Asp Glu Leu Leu Thr Lys Leu Glu Gln Pro Leu Ala Thr Ile
1               5                   10                  15

Leu Ala Glu Met Glu Phe Thr Gly Val Lys Val Asp Thr Lys Arg Leu
                20                  25                  30

Glu Gln Met Gly Ser Glu Leu Ala Glu Gln Leu Gly Ala Val Glu Gln
            35                  40                  45

Arg Ile Tyr Glu Leu Ala Gly Gln Glu Phe Asn Ile Asn Ser Pro Lys
```

```
                    50                  55                  60
Gln Leu Gly Val Ile Leu Phe Glu Lys Leu Gln Leu Pro Val Leu Lys
 65                  70                  75                  80

Lys Thr Lys Thr Gly Tyr Ser Thr Ser Ala Asp Val Leu Glu Lys Leu
                     85                  90                  95

Ala Pro His His Glu Ile Val Glu Asn Ile Leu His Tyr Arg Gln Leu
                100                 105                 110

Gly Lys Leu Gln Ser Thr Tyr Ile Glu Gly Leu Leu Lys Val Val His
                115                 120                 125

Pro Asp Thr Gly Lys Val His Thr Met Phe Asn Gln Ala Leu Thr Gln
            130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
                195                 200                 205

Arg Asp Leu Asp Ile His Thr Lys Thr Ala Met Asp Ile Phe His Val
            210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
                275                 280                 285

Ala Lys Gln Lys Gly Tyr Val Thr Thr Leu Leu His Arg Arg Arg Tyr
            290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Gln Leu Val Pro Glu Val Met
370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 62
<211> LENGTH: 408
<212> TYPE: PRT
<213> ORGANISM: Artificial Sequence
<220> FEATURE:
<223> OTHER INFORMATION: Synthetic construct

<400> SEQUENCE: 62

Glu Gln Asp Arg Leu Leu Thr Asp Leu Glu Gln Pro Leu Ser Ser Ile
```

```
  1               5                   10                  15
Leu Ala Glu Met Glu Phe Thr Gly Val Lys Val Asp Thr Lys Arg Leu
                 20                  25                  30
Glu Gln Met Gly Glu Glu Leu Ala Glu Gln Leu Arg Ala Val Glu Gln
                 35                  40                  45
Arg Ile Tyr Glu Leu Ala Gly Gln Glu Phe Asn Ile Asn Ser Pro Lys
 50                  55                  60
Gln Leu Gly Val Ile Leu Phe Glu Lys Leu Gln Leu Pro Val Leu Lys
 65                  70                  75                  80
Lys Thr Lys Thr Gly Tyr Ser Thr Ser Ala Asp Val Leu Glu Lys Leu
                 85                  90                  95
Ala Pro His His Glu Ile Val Glu Asn Ile Leu His Tyr Arg Gln Leu
                100                 105                 110
Gly Lys Leu Gln Ser Thr Tyr Ile Glu Gly Leu Leu Lys Val Val His
                115                 120                 125
Pro Asp Thr Gly Lys Val His Thr Ile Phe Asn Gln Ala Leu Thr Gln
                130                 135                 140
Thr Gly Arg Leu Ser Ser Thr Glu Pro Asn Leu Gln Asn Ile Pro Ile
145                 150                 155                 160
Arg Leu Glu Glu Gly Arg Lys Ile Arg Gln Ala Phe Val Pro Ser Glu
                165                 170                 175
Pro Asp Trp Leu Ile Phe Ala Ala Asp Tyr Ser Gln Ile Glu Leu Arg
                180                 185                 190
Val Leu Ala His Ile Ala Asn Asp Asp Asn Leu Ile Glu Ala Phe Arg
                195                 200                 205
Arg Asp Leu Asp Ile His Thr Lys Thr Ala Met Asp Ile Phe His Val
                210                 215                 220
Ser Glu Asp Glu Val Thr Ala Asn Met Arg Arg Gln Ala Lys Ala Val
225                 230                 235                 240
Asn Phe Gly Ile Val Tyr Gly Ile Ser Asp Tyr Gly Leu Ala Gln Asn
                245                 250                 255
Leu Asn Ile Thr Arg Lys Glu Ala Ala Glu Phe Ile Glu Arg Tyr Phe
                260                 265                 270
Glu Ser Phe Pro Gly Val Lys Gln Tyr Met Glu Asn Ile Val Gln Glu
                275                 280                 285
Ala Lys Gln Lys Gly Tyr Val Thr Thr Leu Leu His Arg Arg Arg Tyr
                290                 295                 300
Leu Pro Asp Ile Thr Ser Arg Asn Phe Asn Val Arg Ser Phe Ala Glu
305                 310                 315                 320
Arg Thr Ala Met Asn Thr Pro Ile Gln Gly Ser Ala Ala Asp Ile Ile
                325                 330                 335
Lys Lys Ala Met Ile Asp Leu Ala Ala Arg Leu Lys Glu Glu Arg Leu
                340                 345                 350
Gln Ala Arg Leu Leu Leu Gln Val His Asp Glu Leu Ile Leu Glu Ala
                355                 360                 365
Pro Lys Glu Glu Ile Glu Arg Leu Cys Gln Leu Val Pro Glu Val Met
                370                 375                 380
Glu Gln Ala Val Thr Leu Arg Val Pro Leu Lys Val Asp Tyr His Tyr
385                 390                 395                 400
Gly Pro Thr Trp Tyr Asp Ala Lys
                405

<210> SEQ ID NO 63
```

<211> LENGTH: 408
<212> TYPE: PRT
<213> ORGANISM: Artificial Sequence
<220> FEATURE:
<223> OTHER INFORMATION: Synthetic construct

<400> SEQUENCE: 63

```
Glu Gln Tyr Glu Leu Phe Thr Asp Leu Glu Met Pro Leu Ala Leu Ile
1               5                   10                  15

Leu Ala Asp Met Glu Tyr Thr Gly Val Lys Val Asp Val Glu Arg Leu
            20                  25                  30

Lys Glu Met Gly Glu Glu Leu Thr Glu Arg Leu Lys Glu Ile Glu Gln
        35                  40                  45

Lys Ile Tyr Glu Leu Ala Gly Gln Glu Phe Asn Ile Asn Ser Pro Lys
    50                  55                  60

Gln Leu Gly Val Ile Leu Phe Glu Lys Leu Gly Leu Pro Val Ile Lys
65                  70                  75                  80

Lys Thr Lys Thr Gly Tyr Ser Thr Ser Ala Asp Val Leu Glu Lys Leu
                85                  90                  95

Ala Ser His His Glu Ile Ile Arg His Ile Leu His Tyr Arg Gln Leu
            100                 105                 110

Gly Lys Leu Gln Ser Thr Tyr Ile Glu Gly Leu Leu Lys Val Val His
        115                 120                 125

Glu Asp Thr Gly Lys Val His Thr Arg Phe Asn Gln Ala Leu Thr Gln
    130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Gly Trp Val Ile Phe Ala Ala Asp Tyr Ser Gln Ile Glu Leu Arg
            180                 185                 190

Val Leu Ala His Ile Ala Asn Asp Glu Asn Leu Ile Glu Ala Phe Arg
        195                 200                 205

His Asp Met Asp Ile His Thr Lys Thr Ala Met Asp Val Phe His Val
    210                 215                 220

Ser Glu Asp Glu Val Thr Ser Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Gly Glu Phe Ile Glu Arg Tyr Leu
            260                 265                 270

Glu Ser Phe Pro Gly Val Lys Glu Tyr Met Asp Asp Ile Val Gln Glu
        275                 280                 285

Ala Lys Gln Lys Gly Tyr Val Thr Thr Leu Leu His Arg Arg Arg Tyr
    290                 295                 300

Leu Pro Glu Ile Thr Ser Arg Asn Phe Asn Leu Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Asp Arg Leu Lys Glu Glu Asn Leu
            340                 345                 350

Gln Ala Arg Leu Leu Leu Gln Val His Asp Glu Leu Ile Phe Glu Ala
        355                 360                 365

Pro Lys Glu Glu Ile Glu Lys Leu Lys Lys Ile Val Pro Glu Val Met
    370                 375                 380
```

Glu Asn Ala Val Glu Leu Lys Val Pro Leu Lys Val Asp Tyr Ser Tyr
385                 390                 395                 400

Gly Pro Thr Trp Tyr Asp Ala Lys
                405

<210> SEQ ID NO 64
<211> LENGTH: 408
<212> TYPE: PRT
<213> ORGANISM: Artificial Sequence
<220> FEATURE:
<223> OTHER INFORMATION: Synthetic construct

<400> SEQUENCE: 64

Glu Gln Asp Glu Leu Leu Thr Glu Leu Glu Gln Pro Leu Ala Ala Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
    130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Asp Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Asn Ile Thr Arg Lys Glu Ala Ala Glu Phe Ile Glu Arg Tyr Phe
            260                 265                 270

Glu Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

```
Lys Lys Ala Met Ile Asp Leu Ala Ala Arg Leu Lys Glu Glu Arg Leu
            340                 345                 350

Gln Ala Arg Leu Leu Gln Val His Asp Glu Leu Ile Leu Glu Ala
        355                 360                 365

Pro Lys Glu Glu Ile Glu Arg Leu Cys Lys Leu Val Pro Glu Val Met
370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 65
<211> LENGTH: 408
<212> TYPE: PRT
<213> ORGANISM: Artificial Sequence
<220> FEATURE:
<223> OTHER INFORMATION: Synthetic construct

<400> SEQUENCE: 65

Glu Gln Asp Arg Leu Leu Ile Lys Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Arg Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
    130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285
```

```
Ala Lys Gln Lys Gly Tyr Val Thr Thr Leu Leu His Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
                355                 360                 365

Pro Lys Glu Glu Met Glu Arg Leu Cys Arg Leu Val Pro Glu Val Met
370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 66
<211> LENGTH: 408
<212> TYPE: PRT
<213> ORGANISM: Artificial Sequence
<220> FEATURE:
<223> OTHER INFORMATION: Synthetic construct

<400> SEQUENCE: 66

Asp Gln Tyr Glu Leu Phe Glu Asp Leu Glu Met Pro Leu Ala Leu Ile
1               5                   10                  15

Leu Gly Glu Met Glu Ser Thr Gly Val Lys Val Asp Val Glu Arg Leu
                20                  25                  30

Lys Arg Met Gly Glu Glu Leu Thr Glu Lys Leu Lys Glu Tyr Glu Glu
            35                  40                  45

Lys Ile His Glu Leu Ala Gly Glu Pro Phe Asn Ile Asn Ser Pro Lys
        50                  55                  60

Gln Leu Gly Val Ile Leu Phe Glu Lys Leu Gly Leu Pro Val Ile Lys
65                  70                  75                  80

Lys Thr Lys Thr Gly Tyr Ser Thr Ser Ala Asp Val Leu Glu Lys Leu
                85                  90                  95

Ala Asp Lys His Glu Ile Ile Arg Tyr Ile Leu His Tyr Arg Gln Ile
                100                 105                 110

Gly Lys Leu Gln Ser Thr Tyr Ile Glu Gly Leu Leu Lys Val Thr Arg
            115                 120                 125

Lys Asp Thr His Lys Val His Thr Arg Phe Asn Gln Ala Leu Thr Gln
130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Glu Gly Trp Leu Ile Phe Ala Ala Asp Tyr Ser Gln Ile Glu Leu Arg
            180                 185                 190

Val Leu Ala His Ile Ser Lys Asp Glu Asn Leu Ile Glu Ala Phe Thr
        195                 200                 205

His Asp Met Asp Ile His Thr Lys Thr Ala Met Asp Val Phe His Val
    210                 215                 220

Ser Glu Asp Glu Val Thr Ser Ala Met Arg Arg Gln Ala Lys Ala Val
225                 230                 235                 240
```

```
Asn Phe Gly Ile Val Tyr Gly Ile Ser Asp Tyr Gly Leu Ser Gln Asn
            245                 250                 255

Leu Gly Ile Thr Arg Lys Glu Ala Gly Ala Phe Ile Glu Arg Tyr Leu
            260                 265                 270

Glu Ser Phe Pro Gly Val Lys Ala Tyr Met Glu Asp Ile Val Gln Glu
            275                 280                 285

Ala Lys Gln Lys Gly Tyr Val Thr Thr Leu Leu His Arg Arg Arg Tyr
        290                 295                 300

Ile Pro Glu Ile Thr Ser Arg Asn Phe Asn Ile Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Ala Arg Leu Lys Glu Glu Asn Leu
            340                 345                 350

Gln Ala Arg Leu Leu Leu Gln Val His Asp Glu Leu Ile Phe Glu Ala
            355                 360                 365

Pro Lys Glu Glu Ile Glu Ile Leu Glu Lys Ile Val Pro Glu Val Met
        370                 375                 380

Glu His Ala Leu Glu Leu Asp Val Pro Leu Lys Val Asp Tyr Ala Ser
385                 390                 395                 400

Gly Pro Ser Trp Tyr Asp Ala Lys
                405

<210> SEQ ID NO 67
<211> LENGTH: 408
<212> TYPE: PRT
<213> ORGANISM: Artificial Sequence
<220> FEATURE:
<223> OTHER INFORMATION: Synthetic construct

<400> SEQUENCE: 67

Glu Gln Asp Arg Leu Leu Thr Lys Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Arg Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
130                 135                 140

Thr Gly Arg Leu Ser Ser Thr Gly Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190
```

```
Val Leu Ala His Ile Ala Asp Asp Asn Leu Ile Glu Ala Phe Arg
            195                 200                 205

Arg Asp Leu Asp Ile His Thr Lys Thr Ala Met Asp Ile Phe His Val
    210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
            245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
            275                 280                 285

Ala Lys Gln Lys Gly Tyr Val Thr Thr Leu Leu His Arg Arg Arg Tyr
            290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Gln Leu Val Pro Glu Val Met
370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 68
<211> LENGTH: 408
<212> TYPE: PRT
<213> ORGANISM: Artificial Sequence
<220> FEATURE:
<223> OTHER INFORMATION: Synthetic construct

<400> SEQUENCE: 68

Glu Gln Asp Glu Leu Leu Thr Lys Leu Glu Gln Pro Leu Ala Leu Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Lys Glu Ile Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val Arg
        115                 120                 125

Pro Asp Thr Gly Lys Val His Thr Met Phe Asn Gln Ala Leu Thr Gln
130                 135                 140
```

```
Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
            165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
            195                 200                 205

Arg Asp Leu Asp Ile His Thr Lys Thr Ala Met Asp Ile Phe His Val
210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ser Gln Asn
            245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Glu Ile Val Gln Glu
            275                 280                 285

Ala Lys Gln Lys Gly Tyr Val Thr Thr Leu Leu His Arg Arg Arg Tyr
            290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Lys Leu Val Pro Glu Val Met
370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 69
<211> LENGTH: 399
<212> TYPE: PRT
<213> ORGANISM: Artificial Sequence
<220> FEATURE:
<223> OTHER INFORMATION: Synthetic construct

<400> SEQUENCE: 69

Glu Gln Pro Leu Ser Ser Ile Leu Ala Glu Met Glu Phe Ala Gly Val
1               5                   10                  15

Lys Val Asp Thr Lys Arg Leu Glu Gln Met Gly Glu Glu Leu Ala Glu
            20                  25                  30

Gln Leu Lys Glu Gln Glu Gln Arg Ile Tyr Glu Leu Ala Gly Gln Glu
            35                  40                  45

Phe Asn Ile Asn Ser Pro Lys Gln Leu Gly Val Ile Leu Phe Glu Lys
        50                  55                  60

Leu Gln Leu Pro Val Leu Lys Lys Thr Lys Thr Gly Tyr Ser Thr Ser
65                  70                  75                  80

Ala Asp Val Leu Glu Lys Leu Ala Pro Tyr His Glu Ile Val Glu Asn
                85                  90                  95
```

Ile Leu His Tyr Arg Gln Leu Gly Lys Leu Gln Ser Thr Tyr Ile Glu
                100                 105                 110

Gly Leu Leu Lys Val Val Arg Pro Asp Thr Lys Val His Thr Ile
            115                 120                 125

Phe Asn Gln Ala Leu Thr Gln Thr Gly Arg Leu Ser Ser Thr Glu Pro
        130                 135                 140

Asn Leu Gln Asn Ile Pro Ile Arg Leu Glu Glu Gly Arg Lys Ile Arg
145                 150                 155                 160

Gln Ala Phe Val Pro Ser Glu Ser Asp Trp Leu Ile Phe Ala Ala Asp
                165                 170                 175

Tyr Ser Gln Ile Glu Leu Arg Val Leu Ala His Ile Ala Glu Asp Glu
            180                 185                 190

Asn Leu Met Glu Ala Phe Arg Arg Asp Leu Asp Ile His Thr Lys Thr
        195                 200                 205

Ala Met Asp Ile Phe Gln Val Ser Glu Asp Glu Val Thr Pro Asn Met
210                 215                 220

Arg Arg Gln Ala Lys Ala Val Asn Phe Gly Ile Val Tyr Gly Ile Ser
225                 230                 235                 240

Asp Tyr Gly Leu Ser Gln Asn Leu Gly Ile Ser Arg Lys Glu Ala Ala
                245                 250                 255

Glu Phe Ile Glu Arg Tyr Phe Glu Ser Phe Pro Gly Val Lys Arg Tyr
            260                 265                 270

Met Glu Asn Ile Val Gln Glu Ala Lys Gln Lys Gly Tyr Val Thr Thr
        275                 280                 285

Leu Leu His Arg Arg Arg Tyr Asp Pro Asp Ile Thr Ser Arg Asn Phe
290                 295                 300

Asn Val Arg Ser Phe Ala Glu Arg Met Ala Met Asn Thr Pro Ile Gln
305                 310                 315                 320

Gly Ser Ala Ala Asp Ile Ile Lys Lys Ala Met Ile Asp Leu Asn Ala
                325                 330                 335

Arg Leu Lys Glu Glu Arg Leu Gln Ala Arg Leu Leu Leu Gln Val His
            340                 345                 350

Asp Glu Leu Ile Leu Glu Ala Pro Lys Glu Glu Met Glu Arg Leu Cys
        355                 360                 365

Arg Leu Val Pro Glu Val Met Glu Gln Ala Val Thr Leu Arg Val Pro
370                 375                 380

Leu Lys Val Asp Tyr His Tyr Gly Ser Thr Trp Tyr Asp Ala Lys
385                 390                 395

<210> SEQ ID NO 70
<211> LENGTH: 408
<212> TYPE: PRT
<213> ORGANISM: Artificial Sequence
<220> FEATURE:
<223> OTHER INFORMATION: Synthetic construct

<400> SEQUENCE: 70

Glu Gln Asp Glu Leu Leu Ile Lys Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Gly Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Tyr
290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Arg Leu Val Pro Glu Val Met
370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 71
<211> LENGTH: 408
<212> TYPE: PRT
<213> ORGANISM: Artificial Sequence
<220> FEATURE:
<223> OTHER INFORMATION: Synthetic construct

<400> SEQUENCE: 71

Glu Gln Asp Arg Leu Leu Thr Glu Leu Glu Gln Pro Leu Ser Ser Ile
1               5                   10                  15

```
Leu Ala Glu Met Glu Phe Ala Gly Val Lys Val Asp Thr Lys Arg Leu
             20                  25                  30

Glu Gln Met Gly Glu Leu Ala Glu Gln Leu Lys Glu Val Glu Gln
         35                  40                  45

Arg Ile Tyr Glu Leu Ala Gly Gln Glu Phe Asn Ile Asn Ser Pro Lys
 50                  55                  60

Gln Leu Gly Val Ile Leu Phe Glu Lys Leu Gln Leu Pro Val Leu Lys
 65                  70                  75                  80

Lys Thr Lys Thr Gly Tyr Ser Thr Ser Ala Asp Val Leu Glu Lys Leu
                 85                  90                  95

Ala Pro Tyr His Glu Ile Val Glu Asn Ile Leu His Tyr Arg Gln Leu
             100                 105                 110

Gly Lys Leu Gln Ser Thr Tyr Ile Glu Gly Leu Leu Lys Val Val His
             115                 120                 125

Pro Asp Thr Lys Lys Val His Thr Arg Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                 165                 170                 175

Ser Asp Trp Leu Ile Phe Ala Ala Asp Tyr Ser Gln Ile Glu Leu Arg
             180                 185                 190

Val Leu Ala His Ile Ala Glu Asp Asp Asn Leu Met Glu Ala Phe Arg
             195                 200                 205

Arg Asp Leu Asp Ile His Thr Lys Thr Ala Met Asp Ile Phe Gln Val
             210                 215                 220

Ser Glu Asp Glu Val Thr Pro Asn Met Arg Arg Gln Ala Lys Ala Val
225                 230                 235                 240

Asn Phe Gly Ile Val Tyr Gly Ile Ser Asp Tyr Gly Leu Ala Gln Asn
                 245                 250                 255

Leu Asn Ile Ser Arg Lys Glu Ala Ala Glu Phe Ile Glu Arg Tyr Phe
             260                 265                 270

Glu Ser Phe Pro Gly Val Lys Arg Tyr Met Glu Asn Ile Val Gln Glu
             275                 280                 285

Ala Lys Gln Lys Gly Tyr Val Thr Thr Leu Leu His Arg Arg Arg Tyr
             290                 295                 300

Leu Pro Asp Ile Thr Ser Arg Asn Phe Asn Val Arg Ser Phe Ala Glu
305                 310                 315                 320

Arg Met Ala Met Asn Thr Pro Ile Gln Gly Ser Ala Ala Asp Ile Ile
                 325                 330                 335

Lys Lys Ala Met Ile Asp Leu Asn Ala Arg Leu Lys Glu Glu Arg Leu
             340                 345                 350

Gln Ala Arg Leu Leu Leu Gln Val His Asp Glu Leu Ile Leu Glu Ala
             355                 360                 365

Pro Lys Glu Glu Met Glu Arg Leu Cys Lys Leu Val Pro Glu Val Met
             370                 375                 380

Glu Gln Ala Val Glu Leu Arg Val Pro Leu Lys Val Asp Tyr His Tyr
385                 390                 395                 400

Gly Ser Thr Trp Tyr Asp Ala Lys
                 405

<210> SEQ ID NO 72
<211> LENGTH: 408
```

```
<212> TYPE: PRT
<213> ORGANISM: Artificial Sequence
<220> FEATURE:
<223> OTHER INFORMATION: Synthetic construct

<400> SEQUENCE: 72

Glu Gln Asp Glu Leu Leu Thr Lys Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Arg Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Gln Leu Val Pro Glu Val Met
    370                 375                 380
```

-continued

```
Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 73
<211> LENGTH: 408
<212> TYPE: PRT
<213> ORGANISM: Artificial Sequence
<220> FEATURE:
<223> OTHER INFORMATION: Synthetic construct

<400> SEQUENCE: 73

Glu Gln Asp Glu Leu Phe Thr Asp Leu Glu Gln Pro Leu Ala Leu Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Lys Glu Ile Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Glu Asn Leu Ile Glu Ala Phe Arg
        195                 200                 205

Arg Asp Leu Asp Ile His Thr Lys Thr Ala Met Asp Ile Phe His Val
210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Gln Tyr Met Glu Asn Ile Val Gln Glu
        275                 280                 285

Ala Lys Gln Lys Gly Tyr Val Thr Thr Leu Leu His Arg Arg Arg Tyr
290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335
```

```
Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Lys Leu Val Pro Glu Val Met
370                 375                 380

Glu Asn Ala Val Thr Leu Arg Val Pro Leu Lys Val Asp Tyr His Tyr
385                 390                 395                 400

Gly Pro Thr Trp Tyr Asp Ala Lys
                405
```

<210> SEQ ID NO 74
<211> LENGTH: 408
<212> TYPE: PRT
<213> ORGANISM: Artificial Sequence
<220> FEATURE:
<223> OTHER INFORMATION: Synthetic construct

<400> SEQUENCE: 74

```
Glu Gln Asp Glu Leu Phe Thr Glu Leu Glu Leu Pro Leu Ala Leu Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His Arg Glu Ile Val Glu Asn Ile Leu His Tyr Arg Gln Leu
                100                 105                 110

Gly Lys Leu Gln Ser Thr Tyr Ile Glu Gly Leu Leu Lys Val Val His
            115                 120                 125

Pro Asp Thr Gly Lys Val His Thr Arg Phe Asn Gln Ala Leu Thr Gln
        130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asn Asp Asp Asn Leu Ile Glu Ala Phe Arg
        195                 200                 205

Arg Asp Met Asp Ile His Thr Lys Thr Ala Met Asp Val Phe His Val
210                 215                 220

Ser Glu Asp Glu Val Thr Ser Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Ala Glu Phe Ile Glu Arg Tyr Phe
            260                 265                 270

Gln Ser Phe Pro Gly Val Lys Glu Tyr Met Glu Asp Ile Val Gln Glu
        275                 280                 285
```

```
Ala Lys Gln Lys Gly Tyr Val Thr Thr Leu Leu His Arg Arg Arg Phe
    290                 295                 300
Leu Pro Glu Ile Thr Ser Arg Asn Phe Asn Leu Arg Ser Phe Ala Glu
305                 310                 315                 320
Arg Thr Ala Met Asn Thr Pro Ile Gln Gly Ser Ala Ala Asp Ile Ile
                325                 330                 335
Lys Lys Ala Met Ile Asp Met Ala Ala Arg Leu Lys Glu Glu Arg Leu
            340                 345                 350
Gln Ala Arg Leu Leu Leu Gln Val His Asp Glu Leu Ile Phe Glu Ala
                355                 360                 365
Pro Lys Glu Glu Ile Glu Arg Leu Glu Lys Leu Val Pro Glu Val Met
370                 375                 380
Glu His Ala Val Glu Leu Arg Val Pro Leu Lys Val Asp Tyr Arg Tyr
385                 390                 395                 400
Gly Pro Thr Trp Tyr Asp Ala Lys
                405

<210> SEQ ID NO 75
<211> LENGTH: 408
<212> TYPE: PRT
<213> ORGANISM: Artificial Sequence
<220> FEATURE:
<223> OTHER INFORMATION: Synthetic construct

<400> SEQUENCE: 75

Glu Gln Asp Leu Leu Leu Glu Leu Glu Gln Pro Leu Ile Leu Ile
1               5                   10                  15
Leu Ala Glu Met Glu Phe Thr Gly Val Asp Val Asp Thr Lys Arg Leu
            20                  25                  30
Glu Gln Met Gly Leu Glu Leu Ala Glu Gln Leu Val Glu Gln Glu Gln
        35                  40                  45
Arg Ile Tyr Glu Leu Ala Gly Gln Glu Phe Asn Ile Asn Ser Pro Lys
    50                  55                  60
Gln Leu Gly Leu Ile Leu Phe Glu Lys Leu Gln Leu Pro Val Leu Lys
65                  70                  75                  80
Lys Thr Lys Thr Gly Tyr Ser Thr Ser Ala Asp Val Leu Glu Lys Leu
                85                  90                  95
Ala Pro Glu His Glu Ile Val Glu Asn Ile Leu His Tyr Arg Gln Leu
            100                 105                 110
Gly Lys Leu Gln Ser Thr Tyr Ile Glu Gly Leu Leu Lys Val Val Asp
        115                 120                 125
Thr Asp Thr Gly Lys Val His Thr Met Phe Asn Gln Ala Leu Thr Gln
130                 135                 140
Thr Gly Arg Leu Ser Ser Ala Glu Pro Asn Leu Gln Asn Ile Pro Ile
145                 150                 155                 160
Arg Leu Glu Glu Gly Arg Lys Ile Arg Gln Ala Phe Val Pro Ser Glu
                165                 170                 175
Pro Leu Trp Leu Ile Phe Ala Ala Asp Tyr Ser Gln Ile Glu Leu Arg
            180                 185                 190
Val Leu Ala His Ile Ala Asp Asp Asn Leu Ala Glu Ala Phe Arg
        195                 200                 205
Arg Asp Leu Asp Ile His Thr Lys Thr Ala Met Asp Ile Phe His Val
    210                 215                 220
Ser Glu Glu Glu Val Thr Ala Arg Met Arg Arg Gln Ala Lys Ala Val
225                 230                 235                 240
```

Asn Phe Gly Ile Val Tyr Gly Ile Ser Asp Tyr Gly Leu Ala Gln Asn
                    245                 250                 255

Leu Asn Ile Lys Arg Lys Glu Ala Ala Glu Phe Ile Glu Arg Tyr Phe
            260                 265                 270

Ala Ser Phe Pro Gly Val Lys Arg Tyr Met Glu Val Ile Val Gln Glu
        275                 280                 285

Ala Lys Gln Lys Gly Tyr Val Thr Thr Leu Leu His Arg Arg Arg Tyr
    290                 295                 300

Asp Pro Asp Ile Thr Ser Arg Asn Phe Asn Val Arg Ser Phe Ala Glu
305                 310                 315                 320

Arg Met Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Gln Leu
            340                 345                 350

Gln Ala Arg Leu Leu Leu Gln Val His Asp Glu Leu Ile Leu Glu Ala
        355                 360                 365

Pro Lys Glu Glu Met Glu Arg Leu Cys Val Leu Val Pro Glu Val Met
    370                 375                 380

Glu Gln Ala Val Arg Leu Arg Val Pro Leu Lys Val Asp Tyr His Tyr
385                 390                 395                 400

Gly Trp Thr Trp Tyr Asp Ala Lys
                405

<210> SEQ ID NO 76
<211> LENGTH: 408
<212> TYPE: PRT
<213> ORGANISM: Artificial Sequence
<220> FEATURE:
<223> OTHER INFORMATION: Synthetic construct

<400> SEQUENCE: 76

Glu Gln Asp Glu Leu Leu Thr Glu Leu Glu Leu Pro Leu Ala Leu Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Lys Glu Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65              70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Arg Phe Asn Gln Ala Leu Thr Gln
    130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

-continued

```
Val Leu Ala His Ile Ala Asn Asp Asn Leu Ile Glu Ala Phe Arg
        195                 200                 205
Arg Asp Met Asp Ile His Thr Lys Thr Ala Met Asp Val Phe His Val
210                 215                 220
Ser Glu Asp Glu Val Thr Ser Asn Met Arg Arg Gln Ala Lys Ala Val
225                 230                 235                 240
Asn Phe Gly Ile Val Tyr Gly Ile Ser Asp Tyr Gly Leu Ser Gln Asn
            245                 250                 255
Leu Gly Ile Thr Arg Lys Glu Ala Ala Glu Phe Ile Glu Arg Tyr Phe
        260                 265                 270
Glu Ser Phe Pro Gly Val Lys Glu Tyr Met Glu Asp Ile Val Gln Glu
    275                 280                 285
Ala Lys Gln Lys Gly Tyr Val Thr Thr Leu Leu His Arg Arg Arg Tyr
290                 295                 300
Leu Pro Glu Ile Thr Ser Arg Asn Phe Asn Leu Arg Ser Phe Ala Glu
305                 310                 315                 320
Arg Thr Ala Met Asn Thr Pro Ile Gln Gly Ser Ala Ala Asp Ile Ile
            325                 330                 335
Lys Lys Ala Met Ile Asp Met Ala Ala Arg Leu Lys Glu Arg Leu
        340                 345                 350
Gln Ala Arg Leu Leu Leu Gln Val His Asp Glu Leu Ile Phe Glu Ala
    355                 360                 365
Pro Lys Glu Glu Ile Glu Arg Leu Cys Lys Leu Val Pro Glu Val Met
370                 375                 380
Glu His Ala Val Glu Leu Arg Val Pro Leu Lys Val Asp Tyr His Tyr
385                 390                 395                 400
Gly Pro Thr Trp Tyr Asp Ala Lys
            405

<210> SEQ ID NO 77
<211> LENGTH: 408
<212> TYPE: PRT
<213> ORGANISM: Artificial Sequence
<220> FEATURE:
<223> OTHER INFORMATION: Synthetic construct

<400> SEQUENCE: 77

Glu Gln Asp Glu Leu Phe Thr Glu Leu Glu Met Pro Leu Ala Leu Ile
1               5                   10                  15
Leu Ala Glu Met Glu Phe Thr Gly Val Lys Val Asp Thr Lys Arg Leu
            20                  25                  30
Glu Gln Met Gly Glu Glu Leu Ala Glu Gln Leu Lys Ala Ile Glu Gln
        35                  40                  45
Arg Ile Tyr Glu Leu Ala Gly Gln Glu Phe Asn Ile Asn Ser Pro Lys
    50                  55                  60
Gln Leu Gly Val Ile Leu Phe Glu Lys Leu Gln Leu Pro Val Leu Lys
65                  70                  75                  80
Lys Thr Lys Thr Gly Tyr Ser Thr Ser Ala Asp Val Leu Glu Lys Leu
                85                  90                  95
Ala Pro His His Glu Ile Val Glu Asn Ile Leu His Tyr Arg Gln Leu
            100                 105                 110
Gly Lys Leu Gln Ser Thr Tyr Ile Glu Gly Leu Leu Lys Val Val His
        115                 120                 125
Pro Asp Thr Gly Lys Val His Thr Met Phe Asn Gln Ala Leu Thr Gln
    130                 135                 140
```

```
Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
            165                 170                 175

Pro Asp Trp Leu Ile Phe Ala Ala Asp Tyr Ser Gln Ile Glu Leu Arg
            180                 185                 190

Val Leu Ala His Ile Ala Asn Asp Glu Asn Leu Ile Glu Ala Phe Arg
            195                 200                 205

Arg Asp Leu Asp Ile His Thr Lys Thr Ala Met Asp Ile Phe His Val
210                 215                 220

Ser Glu Asp Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Asn Ile Thr Arg Lys Glu Ala Ala Glu Phe Ile Glu Arg Tyr Phe
            260                 265                 270

Glu Ser Phe Pro Gly Val Lys Gln Tyr Met Glu Asp Ile Val Gln Glu
            275                 280                 285

Ala Lys Gln Lys Gly Tyr Val Thr Thr Leu Leu His Arg Arg Arg Tyr
290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Lys Leu Val Pro Glu Val Met
370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405
```

<210> SEQ ID NO 78
<211> LENGTH: 408
<212> TYPE: PRT
<213> ORGANISM: Artificial Sequence
<220> FEATURE:
<223> OTHER INFORMATION: Synthetic construct

<400> SEQUENCE: 78

```
Glu Gln Asp Glu Leu Leu Thr Lys Leu Glu Gln Pro Leu Ala Thr Ile
1               5                   10                  15

Leu Ala Glu Met Glu Phe Thr Gly Val Lys Val Asp Thr Lys Arg Leu
            20                  25                  30

Glu Gln Met Gly Ser Glu Leu Ala Glu Gln Leu Gly Ala Val Glu Gln
        35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95
```

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
    130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Ile Glu Arg Leu Cys Gln Leu Val Pro Glu Val Met
    370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 79
<211> LENGTH: 408
<212> TYPE: PRT
<213> ORGANISM: Artificial Sequence
<220> FEATURE:
<223> OTHER INFORMATION: Synthetic construct

<400> SEQUENCE: 79

Glu Gln Asp Glu Leu Leu Ile Lys Leu Glu Leu Pro Leu Ala Thr Ile
1               5                   10                  15

Leu Ala Glu Met Glu Phe Thr Gly Val Lys Val Asp Thr Lys Arg Leu
                20                  25                  30

Glu Gln Met Gly Ser Glu Leu Ala Glu Gln Leu Arg Ala Val Glu Gln
            35                  40                  45

```
Arg Ile Tyr Glu Leu Ala Gly Gln Glu Phe Asn Ile Asn Ser Pro Lys
 50                  55                  60

Gln Leu Gly Ile Ile Leu Phe Glu Lys Leu Gln Leu Pro Val Leu Lys
 65                  70                  75                  80

Lys Thr Lys Thr Gly Tyr Ser Thr Ser Ala Asp Val Leu Glu Lys Leu
                 85                  90                  95

Ala Pro His His Glu Ile Val Glu Asn Ile Leu His Tyr Arg Gln Leu
             100                 105                 110

Gly Lys Leu Gln Ser Thr Tyr Ile Glu Gly Leu Leu Lys Val Val His
         115                 120                 125

Pro Asp Thr Gly Lys Val His Thr Arg Phe Asn Gln Ala Leu Thr Gln
    130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Arg Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Glu Ser Phe Pro Gly Val Lys Arg Tyr Met Glu Thr Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Met Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
        355                 360                 365

Pro Lys Glu Glu Met Glu Arg Leu Cys Gln Leu Val Pro Glu Val Met
    370                 375                 380

Glu Gln Ala Val Ala Leu Arg Val Pro Leu Lys Val Asp Tyr His Tyr
385                 390                 395                 400

Gly Pro Thr Trp Tyr Asp Ala Lys
                405
```

<210> SEQ ID NO 80
<211> LENGTH: 408
<212> TYPE: PRT
<213> ORGANISM: Artificial Sequence
<220> FEATURE:
<223> OTHER INFORMATION: Synthetic construct

<400> SEQUENCE: 80

```
Glu Gln Asp Glu Leu Thr Glu Leu Gln Pro Leu Ala Leu Ile
1               5                   10                  15

Leu Ala Glu Met Glu Phe Thr Gly Val Lys Val Asp Thr Lys Arg Leu
            20                  25                  30

Glu Gln Met Gly Glu Glu Leu Ala Glu Gln Leu Lys Ala Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
            115                 120                 125

Pro Asp Thr Gly Lys Val His Thr Met Phe Asn Gln Ala Leu Thr Gln
            130                 135                 140

Thr Gly Arg Leu Ser Ser Ala Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
            195                 200                 205

Arg Asp Leu Asp Ile His Thr Lys Thr Ala Met Asp Ile Phe His Val
210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Arg Tyr Met Glu Asp Ile Val Gln Glu
        275                 280                 285

Ala Lys Gln Lys Gly Tyr Val Thr Thr Leu Leu His Arg Arg Arg Tyr
        290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
            340                 345                 350

Gln Ala Arg Leu Leu Leu Gln Val His Asp Glu Leu Ile Leu Glu Ala
            355                 360                 365

Pro Lys Glu Glu Ile Glu Arg Leu Cys Lys Leu Val Pro Glu Val Met
        370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
            405
```

<210> SEQ ID NO 81
<211> LENGTH: 408
<212> TYPE: PRT
<213> ORGANISM: Artificial Sequence
<220> FEATURE:
<223> OTHER INFORMATION: Synthetic construct

<400> SEQUENCE: 81

```
Glu Gln Tyr Glu Leu Phe Thr Asp Leu Glu Met Pro Leu Ala Leu Ile
1               5                   10                  15

Leu Ala Asp Met Glu Tyr Thr Gly Val Lys Val Asp Val Glu Arg Leu
            20                  25                  30

Lys Glu Met Gly Glu Glu Leu Ala Glu Arg Leu Lys Glu Ile Glu Gln
        35                  40                  45

Lys Ile Tyr Glu Leu Ala Gly Glu Glu Phe Asn Ile Asn Ser Pro Lys
    50                  55                  60

Gln Leu Gly Val Ile Leu Phe Glu Lys Leu Gly Leu Pro Val Ile Lys
65                  70                  75                  80

Lys Thr Lys Thr Gly Tyr Ser Thr Ser Ala Asp Val Leu Glu Lys Leu
                85                  90                  95

Ala Ser Lys His Glu Ile Ile Arg Asn Ile Leu His Tyr Arg Gln Leu
            100                 105                 110

Gly Lys Leu Gln Ser Thr Tyr Ile Glu Gly Leu Leu Lys Val Val His
        115                 120                 125

Gln Asp Thr Gly Lys Val His Thr Arg Phe Asn Gln Ala Leu Thr Gln
    130                 135                 140

Thr Gly Arg Leu Ser Ser Thr Asp Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Glu Gly Trp Val Ile Phe Ala Ala Asp Tyr Ser Gln Ile Glu Leu Arg
            180                 185                 190

Val Leu Ala His Ile Ala Asn Asp Glu Lys Leu Ile Glu Ala Phe Arg
        195                 200                 205

His Asp Met Asp Ile His Thr Lys Thr Ala Met Asp Val Phe His Val
    210                 215                 220

Ser Glu Asp Glu Val Thr Ser Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Gly Ile Thr Arg Lys Glu Ala Ala Glu Phe Ile Glu Arg Tyr Leu
            260                 265                 270

Glu Ser Phe Pro Gly Val Lys Glu Tyr Met Asp Asp Ile Val Gln Glu
        275                 280                 285

Ala Lys Gln Lys Gly Tyr Val Thr Thr Leu Leu His Arg Arg Arg Tyr
    290                 295                 300

Leu Pro Glu Ile Thr Ser Arg Asn Phe Asn Leu Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Met Ala Asn Arg Leu Lys Glu Glu Asn Leu
            340                 345                 350

Gln Ala Arg Leu Leu Leu Gln Val His Asp Glu Leu Ile Phe Glu Ala
        355                 360                 365

Pro Lys Glu Glu Ile Glu Lys Leu Lys Lys Ile Val Pro Glu Val Met
```

```
                370                 375                 380
Glu His Ala Val Glu Leu Lys Val Pro Leu Lys Val Asp Tyr Ser Tyr
385                 390                 395                 400

Gly Pro Thr Trp Tyr Asp Ala Lys
                405
```

<210> SEQ ID NO 82
<211> LENGTH: 408
<212> TYPE: PRT
<213> ORGANISM: Artificial Sequence
<220> FEATURE:
<223> OTHER INFORMATION: Synthetic construct

<400> SEQUENCE: 82

```
Glu Gln Asp Glu Leu Leu Thr Glu Leu Glu Gln Pro Leu Ala Ala Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Lys Glu Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Leu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Lys Lys Val His Thr Arg Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Asp Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ser Gln Asn
                245                 250                 255

Leu Asn Ile Thr Arg Lys Glu Ala Ala Glu Phe Ile Glu Arg Tyr Phe
            260                 265                 270

Glu Ser Phe Pro Gly Val Lys Arg Tyr Met Glu Asn Ile Val Gln Glu
        275                 280                 285

Ala Lys Gln Lys Gly Tyr Val Thr Thr Leu Leu His Arg Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
```

```
                    325                 330                 335
Lys Lys Ala Met Ile Asp Leu Ala Lys Arg Leu Lys Glu Glu Arg Leu
                340                 345                 350

Gln Ala Arg Leu Leu Leu Gln Val His Asp Glu Leu Ile Leu Glu Ala
            355                 360                 365

Pro Lys Glu Glu Ile Glu Arg Leu Glu Lys Leu Val Pro Glu Val Met
        370                 375                 380

Glu Gln Ala Val Glu Leu Arg Val Pro Leu Lys Val Asp Tyr His Tyr
385                 390                 395                 400

Gly Pro Thr Trp Tyr Asp Ala Lys
                405

<210> SEQ ID NO 83
<211> LENGTH: 408
<212> TYPE: PRT
<213> ORGANISM: Artificial Sequence
<220> FEATURE:
<223> OTHER INFORMATION: Synthetic construct

<400> SEQUENCE: 83

Glu Gln Asp Arg Leu Leu Thr Glu Leu Glu Gln Pro Leu Ala Ser Ile
1               5                   10                  15

Leu Ala Glu Met Glu Phe Thr Gly Val Lys Val Asp Thr Lys Arg Leu
                20                  25                  30

Glu Gln Met Gly Glu Leu Thr Glu Gln Leu Arg Ala Val Glu Gln
            35                  40                  45

Arg Ile Tyr Glu Leu Ala Gly Gln Glu Phe Asn Ile Asn Ser Pro Lys
        50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
        210                 215                 220

Ser Glu Glu Glu Val Thr Ala Asn Met Arg Arg Gln Ala Lys Ala Val
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
            260                 265                 270

Ala Ser Phe Pro Gly Val Lys Gln Tyr Met Glu Asn Ile Val Gln Glu
```

```
            275                 280                 285
Ala Lys Gln Lys Gly Tyr Val Thr Thr Leu Leu His Arg Arg Tyr
    290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Gln Val His Asp Glu Leu Ile Leu Glu Ala
            355                 360                 365

Pro Lys Glu Glu Ile Glu Arg Leu Cys Arg Leu Val Pro Glu Val Met
    370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
            405
```

<210> SEQ ID NO 84
<211> LENGTH: 408
<212> TYPE: PRT
<213> ORGANISM: Artificial Sequence
<220> FEATURE:
<223> OTHER INFORMATION: Synthetic construct

<400> SEQUENCE: 84

```
Glu Gln Asp Arg Leu Leu Thr Glu Leu Glu Gln Pro Leu Ala Ser Ile
1               5                   10                  15

Leu Ala Glu Met Glu Phe Thr Gly Val Lys Val Asp Thr Lys Arg Leu
                20                  25                  30

Glu Gln Met Gly Glu Glu Leu Ala Glu Gln Leu Arg Ala Val Glu Gln
            35                  40                  45

Arg Ile Tyr Glu Leu Ala Gly Gln Glu Phe Asn Ile Asn Ser Pro Lys
    50                  55                  60

Gln Leu Gly Val Ile Leu Phe Glu Lys Leu Gln Leu Pro Val Leu Lys
65                  70                  75                  80

Lys Thr Lys Thr Gly Tyr Ser Thr Ser Ala Asp Val Leu Glu Lys Leu
                85                  90                  95

Ala Pro His His Glu Ile Val Glu Asn Ile Leu His Tyr Arg Gln Leu
            100                 105                 110

Gly Lys Leu Gln Ser Thr Tyr Ile Glu Gly Leu Leu Lys Val Val His
        115                 120                 125

Pro Asp Thr Gly Lys Val His Thr Met Phe Asn Gln Ala Leu Thr Gln
130                 135                 140

Thr Gly Arg Leu Ser Ser Thr Glu Pro Asn Leu Gln Asn Ile Pro Ile
145                 150                 155                 160

Arg Leu Glu Glu Gly Arg Lys Ile Arg Gln Ala Phe Val Pro Ser Glu
                165                 170                 175

Pro Asp Trp Leu Ile Phe Ala Ala Asp Tyr Ser Gln Ile Glu Leu Arg
            180                 185                 190

Val Leu Ala His Ile Ala Asp Asp Asn Leu Ile Glu Ala Phe Arg
        195                 200                 205

Arg Asp Leu Asp Ile His Thr Lys Thr Ala Met Asp Ile Phe His Val
    210                 215                 220

Ser Glu Glu Glu Val Thr Ala Asn Met Arg Arg Gln Ala Lys Ala Val
```

```
225                 230                 235                 240

Asn Phe Gly Ile Val Tyr Gly Ile Ser Asp Tyr Gly Leu Ala Gln Asn
                245                 250                 255

Leu Asn Ile Thr Arg Lys Glu Ala Ala Glu Phe Ile Glu Arg Tyr Phe
                260                 265                 270

Ala Ser Phe Pro Gly Val Lys Gln Tyr Met Glu Asn Ile Val Gln Glu
                275                 280                 285

Ala Lys Gln Lys Gly Tyr Val Thr Thr Leu Leu His Arg Arg Arg Tyr
                290                 295                 300

Leu Pro Asp Ile Thr Ser Arg Asn Phe Asn Val Arg Ser Phe Ala Glu
305                 310                 315                 320

Arg Thr Ala Met Asn Thr Pro Ile Gln Gly Ser Ala Ala Asp Ile Ile
                325                 330                 335

Lys Lys Ala Met Ile Asp Leu Ala Ala Arg Leu Lys Glu Glu Arg Leu
                340                 345                 350

Gln Ala Arg Leu Leu Leu Gln Val His Asp Glu Leu Ile Leu Glu Ala
                355                 360                 365

Pro Lys Glu Glu Ile Glu Arg Leu Cys Arg Leu Val Pro Glu Val Met
                370                 375                 380

Glu Gln Ala Val Thr Leu Arg Val Pro Leu Lys Val Asp Tyr His Tyr
385                 390                 395                 400

Gly Pro Thr Trp Tyr Asp Ala Lys
                405

<210> SEQ ID NO 85
<211> LENGTH: 179
<212> TYPE: PRT
<213> ORGANISM: Artificial Sequence
<220> FEATURE:
<223> OTHER INFORMATION: Synthetic construct

<400> SEQUENCE: 85

Glu Glu Glu Glu Lys Pro Leu Glu Asp Ile Glu Phe Ala Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Asn
                35                  40                  45

Val Asn Glu His Gly Arg Phe Phe Leu Arg Pro Glu Thr Ala Leu Ala
            50                  55                  60

Ser Pro Gln Phe Lys Ala Trp Leu Ala Asp Glu Thr Lys Lys Lys Ser
65              70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
                100                 105                 110

Asn Pro Ala Gln Thr Ala Glu Asp Ile Ala Ala Val Ala Lys Met Lys
                115                 120                 125

Gln Tyr Glu Ala Val Arg Ser Asp Glu Ala Val Tyr Gly Lys Gly Val
                130                 135                 140

Lys Arg Ser Leu Pro Asp Glu Gln Ala Leu Ala Glu His Leu Val Arg
145                 150                 155                 160

Lys Ala Ala Ala Ile Trp Ala Leu Glu Gln Pro Phe Met Asp Asp Leu
                165                 170                 175

Arg Lys Asn
```

<210> SEQ ID NO 86
<211> LENGTH: 179
<212> TYPE: PRT
<213> ORGANISM: Artificial Sequence
<220> FEATURE:
<223> OTHER INFORMATION: Synthetic construct

<400> SEQUENCE: 86

```
Ala Glu Glu Glu Lys Pro Leu Glu Glu Met Glu Phe Thr Asp Val Asp
1               5                   10                  15

Glu Ile Thr Glu Glu Met Leu Ala Asp Lys Ala Ala Leu Val Val Glu
            20                  25                  30

Val Gln Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Val Ala Trp Leu Glu Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Asp Asp Val Ala Ala Val Ala Lys Met Lys
        115                 120                 125

Gln Tyr Glu Ala Val Arg Ser Asp Gly Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ile Arg Ala Leu Glu Gln Pro Phe Ile Asp Glu Leu
                165                 170                 175

Arg Arg Arg
```

<210> SEQ ID NO 87
<211> LENGTH: 179
<212> TYPE: PRT
<213> ORGANISM: Artificial Sequence
<220> FEATURE:
<223> OTHER INFORMATION: Synthetic construct

<400> SEQUENCE: 87

```
Glu Glu Glu Glu Lys Pro Leu Ala Glu Met Glu Phe Thr Ile Ala Asp
1               5                   10                  15

Glu Val Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu Arg Gly Arg Phe Phe Leu Arg Thr Glu Thr Ala Leu Ala
    50                  55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125
```

Gln Tyr Glu Ala Val Arg Ser Asp Glu Ala Val Tyr Gly Lys Gly Ala
            130                 135                 140

Lys Arg Ala Leu Pro Asp Glu Pro Thr Leu Ala Glu His Leu Val Arg
145                 150                 155                 160

Lys Ala Ala Ile Trp Ala Leu Glu Glu Pro Phe Leu Asp Glu Leu
                165                 170                 175

Arg Glu Asn

<210> SEQ ID NO 88
<211> LENGTH: 179
<212> TYPE: PRT
<213> ORGANISM: Artificial Sequence
<220> FEATURE:
<223> OTHER INFORMATION: Synthetic construct

<400> SEQUENCE: 88

Ala Glu Glu Glu Lys Pro Leu Ala Asp Met Glu Phe Ala Ile Ala Asp
1               5                   10                  15

Glu Val Thr Glu Glu Met Leu Ala Asp Lys Ala Ala Leu Val Val Glu
            20                  25                  30

Val Met Glu Asp Asn Tyr His Asp Ala Pro Ile Val Gly Phe Ala Asn
        35                  40                  45

Val Asn Glu His Gly Arg Phe Phe Leu Arg Ala Glu Leu Ala Leu Ala
 50                 55                  60

Asp Ser Gln Phe Leu Ala Trp Leu Gly Asp Glu Thr Lys Lys Lys Ser
65                  70                  75                  80

Met Phe Asp Arg Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Asp Asp Val Ala Val Ala Lys Met Lys
        115                 120                 125

Gln Tyr Glu Ala Val Arg Pro Asp Glu Ala Val Tyr Gly Lys Gly Ala
            130                 135                 140

Lys Arg Ser Val Pro Asp Glu Pro Val Leu Ala Glu His Leu Val Arg
145                 150                 155                 160

Lys Ala Ala Ile Trp Ala Leu Glu Arg Pro Phe Leu Asp Glu Leu
                165                 170                 175

Arg Arg Asn

<210> SEQ ID NO 89
<211> LENGTH: 179
<212> TYPE: PRT
<213> ORGANISM: Artificial Sequence
<220> FEATURE:
<223> OTHER INFORMATION: Synthetic construct

<400> SEQUENCE: 89

Ala Glu Gly Glu Lys Pro Leu Ala Glu Met Glu Phe Ala Ile Val Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
 50                 55                  60

Asp Pro Gln Phe Leu Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Val Ala Lys Met Lys
            115                 120                 125

Gln Tyr Glu Ala Val Arg Ser Asp Glu Ala Val Tyr Gly Lys Gly Ala
        130                 135                 140

Lys Arg Ser Leu Pro Asp Glu Pro Thr Leu Ala Glu His Leu Val Arg
145                 150                 155                 160

Lys Ala Ala Ile Trp Ala Leu Glu Gln Pro Phe Ile Asp Glu Leu
                165                 170                 175

Arg Arg Asn

<210> SEQ ID NO 90
<211> LENGTH: 179
<212> TYPE: PRT
<213> ORGANISM: Artificial Sequence
<220> FEATURE:
<223> OTHER INFORMATION: Synthetic construct

<400> SEQUENCE: 90

Ala Glu Glu Glu Lys Pro Leu Glu Asp Ile Glu Phe Asp Ile Ala Asp
1               5                   10                  15

Glu Val Thr Glu Met Leu Ala Asp Lys Ala Ala Leu Val Val Glu
            20                  25                  30

Val Gln Glu Asp Asn Tyr His Asp Ala Pro Ile Val Gly Phe Ala Ile
        35                  40                  45

Val Asn Glu His Gly Arg Phe Phe Ile Arg Thr Glu Thr Ala Leu Ala
50                  55                  60

Ser Pro Gln Phe Lys Ala Trp Leu Ala Asp Glu Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Ala Ala Tyr Leu Leu
            100                 105                 110

Asn Pro Ala Gln Thr Ala Asp Val Ala Val Ala Lys Met Lys
            115                 120                 125

Gln Tyr His Ala Val Arg Ser Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ile Trp Ala Leu Glu Glu Pro Phe Leu Asp Glu Leu
                165                 170                 175

Arg Lys Asn

<210> SEQ ID NO 91
<211> LENGTH: 179
<212> TYPE: PRT
<213> ORGANISM: Artificial Sequence
<220> FEATURE:
<223> OTHER INFORMATION: Synthetic construct

<400> SEQUENCE: 91

Glu Glu Glu Glu Lys Pro Leu Glu Asp Ile Ser Phe Glu Ile Ala Asp

```
                1               5                   10                  15
            Glu Val Thr Glu Asp Met Leu Thr Asp Glu Ser Ala Leu Val Val Glu
                            20                  25                  30

Val Leu Glu Glu Asn Tyr His Lys Ala Asp Ile Val Gly Phe Ala Ile
                            35                  40                  45

Ala Asn Glu Asn Gly Asn Phe Phe Ile Pro Thr Asp Thr Ala Leu Ala
                            50                  55                  60

Ser Pro Gln Phe Lys Lys Trp Leu Glu Asp Thr Lys Lys Lys Ser
            65                      70                  75                  80

Val Phe Asp Ala Lys Arg Ala Ile Val Ala Leu Lys Trp His Gly Ile
                            85                  90                  95

Glu Leu Lys Gly Val Asp Phe Asp Leu Leu Ile Ala Ser Tyr Leu Leu
                            100                 105                 110

Asn Pro Ser Glu Ser Ser Asp Asp Phe Ala Ser Val Ala Lys Thr Lys
                            115                 120                 125

Gly Tyr Asn Ala Val Gln Ser Asp Glu Ala Val Tyr Gly Lys Gly Ala
                            130                 135                 140

Lys Arg Ala Val Pro Asp Glu Glu Lys Leu Ala Glu His Leu Ala Arg
            145                     150                 155                 160

Lys Ala Ala Ala Ile Ser Ala Leu Lys Glu Thr Phe Ile His Glu Leu
                            165                 170                 175

Lys Glu Asn

<210> SEQ ID NO 92
            <211> LENGTH: 179
            <212> TYPE: PRT
            <213> ORGANISM: Artificial Sequence
            <220> FEATURE:
            <223> OTHER INFORMATION: Synthetic construct

<400> SEQUENCE: 92

Thr Glu Glu Lys Glu Leu Glu Asp Ile Asn Val Lys Thr Ala Asp
            1               5                   10                  15

Glu Val Thr Ser Glu Met Leu Thr Asp Pro Ser Ala Leu Val Val Glu
                            20                  25                  30

Gln Leu Gly Asp Asn Tyr His Glu Ala Asp Ile Ile Gly Phe Ala Ile
                            35                  40                  45

Val Asn Glu Asn Gly Ala Phe Phe Ile Pro Lys Glu Thr Ala Leu Gln
                            50                  55                  60

Ser Pro Gln Phe Lys Glu Trp Val Glu Asp Thr Lys Lys Lys Trp
            65                      70                  75                  80

Val Phe Asp Ser Lys Arg Ala Ile Val Ala Leu Arg Trp His Gly Ile
                            85                  90                  95

Glu Leu Lys Gly Val Asp Phe Asp Val Leu Ala Ser Tyr Ile Ile
                            100                 105                 110

Asn Pro Ser Asn Ser Tyr Asp Asp Val Ala Ser Val Ala Lys Glu Tyr
                            115                 120                 125

Gly Leu Asn Ile Val Ser Ser Asp Glu Ala Val Tyr Gly Lys Gly Ala
                            130                 135                 140

Lys Arg Ala Val Pro Ala Glu Asp Glu Leu Ala Glu His Leu Gly Arg
            145                     150                 155                 160

Lys Ala Ala Ala Ile Ser Ala Leu Arg Asp Lys Leu Leu Gln Ala Leu
                            165                 170                 175

Glu Glu Asn
```

<210> SEQ ID NO 93
<211> LENGTH: 179
<212> TYPE: PRT
<213> ORGANISM: Artificial Sequence
<220> FEATURE:
<223> OTHER INFORMATION: Synthetic construct

<400> SEQUENCE: 93

```
Ala Glu Glu Glu Val Pro Leu Ala Glu Met Glu Phe Val Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn
```

<210> SEQ ID NO 94
<211> LENGTH: 179
<212> TYPE: PRT
<213> ORGANISM: Artificial Sequence
<220> FEATURE:
<223> OTHER INFORMATION: Synthetic construct

<400> SEQUENCE: 94

```
Ala Glu Glu Glu Lys Pro Leu Ala Glu Met Glu Phe Val Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Ser Pro Gln Phe Val Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125
```

```
Gln Tyr Glu Ala Val Arg Ser Asp Glu Ala Val Tyr Gly Lys Gly Ala
        130                 135                 140

Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn
```

<210> SEQ ID NO 95
<211> LENGTH: 179
<212> TYPE: PRT
<213> ORGANISM: Artificial Sequence
<220> FEATURE:
<223> OTHER INFORMATION: Synthetic construct

<400> SEQUENCE: 95

```
Glu Glu Glu Glu Val Pro Leu Glu Glu Ile Glu Phe Ala Ile Ala Asp
1               5                   10                  15

Glu Val Thr Glu Glu Met Leu Ala Asp Lys Ala Ala Leu Val Val Glu
                20                  25                  30

Val Leu Glu Glu Asn Tyr His Asp Ala Pro Ile Val Gly Phe Ala Leu
            35                  40                  45

Val Asn Glu His Gly Arg Phe Phe Ile Arg Pro Glu Thr Ala Leu Ala
50                  55                  60

Ser Ser Gln Phe Lys Ala Trp Leu Glu Asp Glu Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
                100                 105                 110

Asn Pro Ala Gln Ser Ala Glu Asp Val Ala Val Ala Lys Met Lys
            115                 120                 125

Gln Tyr Glu Ala Val Arg Ser Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Ile Asp Glu Leu
                165                 170                 175

Arg Glu Asn
```

<210> SEQ ID NO 96
<211> LENGTH: 179
<212> TYPE: PRT
<213> ORGANISM: Artificial Sequence
<220> FEATURE:
<223> OTHER INFORMATION: Synthetic construct

<400> SEQUENCE: 96

```
Ala Glu Glu Glu Ala Pro Leu Glu Asp Ile Phe Asp Ile Ala Asp
1               5                   10                  15

Glu Val Thr Glu Glu Met Leu Ala Asp Lys Ala Ala Leu Val Val Glu
                20                  25                  30

Val Gln Glu Asp Asn Tyr His Asp Ala Pro Ile Val Gly Phe Ala Ile
            35                  40                  45

Val Asn Glu Arg Gly Arg Phe Phe Ile Arg Thr Glu Thr Ala Leu Ala
50                  55                  60

Ser Glu Ala Phe Lys Ala Trp Leu Ala Asp Glu Thr Lys Lys Lys Ser
```

```
                65                  70                  75                  80
Val Phe Asp Ala Lys Arg Ala Ile Val Ala Leu Lys Trp Lys Gly Ile
                    85                  90                  95

Glu Leu Arg Gly Val Asp Phe Asp Leu Leu Leu Ala Ala Tyr Leu Leu
                100                 105                 110

Asn Pro Ala Gln Thr Ala Asp Val Ala Ala Val Ala Lys Met Lys
                115                 120                 125

Gln Tyr His Ala Val Arg Ser Asp Glu Ala Val Tyr Gly Lys Gly Ala
                130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Lys Asn
```

<210> SEQ ID NO 97
<211> LENGTH: 179
<212> TYPE: PRT
<213> ORGANISM: Artificial Sequence
<220> FEATURE:
<223> OTHER INFORMATION: Synthetic construct

<400> SEQUENCE: 97

```
Ala Glu Glu Lys Pro Leu Ala Glu Met Glu Phe Ala Ile Ala Asp
1               5                   10                  15

Glu Val Thr Glu Glu Met Leu Ala Asp Lys Ala Ala Leu Val Val Glu
                20                  25                  30

Val Val Glu Glu Asn Tyr His Asp Ala Pro Ile Val Gly Ile Ala Leu
                35                  40                  45

Val Asn Glu His Gly Arg Phe Phe Leu Arg Pro Glu Thr Ala Leu Ala
50                  55                  60

Ser Pro Gln Phe Leu Ala Trp Leu Gly Asp Glu Thr Lys Lys Lys Ser
65                  70                  75                  80

Met Phe Asp Ser Lys Arg Ala Ile Val Ala Leu Lys Trp Lys Gly Ile
                    85                  90                  95

Glu Leu Arg Gly Val Ala Phe Asp Leu Leu Leu Ala Ala Tyr Leu Leu
                100                 105                 110

Asn Pro Ala Gln Ala Ala Gly Asp Val Ala Ala Val Ala Lys Met Lys
                115                 120                 125

Gln Tyr Glu Ala Val Arg Ser Asp Glu Ala Val Tyr Gly Lys Gly Ala
                130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Arg Asn
```

<210> SEQ ID NO 98
<211> LENGTH: 179
<212> TYPE: PRT
<213> ORGANISM: Artificial Sequence
<220> FEATURE:
<223> OTHER INFORMATION: Synthetic construct

<400> SEQUENCE: 98

```
Ala Glu Glu Lys Pro Leu Ala Glu Met Glu Phe Val Ile Ala Asp
1               5                   10                  15
```

Glu Ile Thr Asp Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Ser Pro Gln Phe Val Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Val Ala Lys Met Lys
            115                 120                 125

Gln Tyr Glu Ala Val Arg Pro Asp Glu Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn

<210> SEQ ID NO 99
<211> LENGTH: 179
<212> TYPE: PRT
<213> ORGANISM: Artificial Sequence
<220> FEATURE:
<223> OTHER INFORMATION: Synthetic construct

<400> SEQUENCE: 99

Ala Glu Glu Glu Lys Pro Leu Glu Glu Met Glu Phe Ala Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Ser Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Val Ala Lys Met Lys
            115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Asn Asn

```
<210> SEQ ID NO 100
<211> LENGTH: 179
<212> TYPE: PRT
<213> ORGANISM: Artificial Sequence
<220> FEATURE:
<223> OTHER INFORMATION: Synthetic construct

<400> SEQUENCE: 100

Ala Glu Glu Glu Val Pro Leu Glu Glu Met Glu Phe Thr Ile Ala Asp
1               5                   10                  15

Glu Ile Thr Glu Glu Met Leu Ala Asp Lys Ala Ala Leu Val Val Glu
            20                  25                  30

Val Leu Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Val Ala Trp Leu Glu Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Leu Pro Asp Glu Pro Val Leu Ala Glu His Leu Val Arg
145                 150                 155                 160

Lys Ala Ala Ile Trp Ala Leu Glu Arg Pro Phe Leu Asp Glu Leu
                165                 170                 175

Arg Glu Asn

<210> SEQ ID NO 101
<211> LENGTH: 179
<212> TYPE: PRT
<213> ORGANISM: Artificial Sequence
<220> FEATURE:
<223> OTHER INFORMATION: Synthetic construct

<400> SEQUENCE: 101

Ala Glu Glu Glu Val Pro Leu Glu Glu Met Glu Phe Val Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Ala Glu Thr Ala Leu Ala
    50                  55                  60

Asp Pro Gln Phe Val Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Val Ala Lys Met Lys
        115                 120                 125

Gln Tyr Glu Ala Val Arg Ser Asp Glu Ala Val Tyr Gly Lys Gly Ala
```

```
                130                 135                 140
Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Glu Asn

<210> SEQ ID NO 102
<211> LENGTH: 179
<212> TYPE: PRT
<213> ORGANISM: Artificial Sequence
<220> FEATURE:
<223> OTHER INFORMATION: Synthetic construct

<400> SEQUENCE: 102

Ala Glu Glu Glu Lys Pro Leu Ala Glu Met Glu Phe Val Ile Ala Asp
1               5                   10                  15

Gly Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
        50                  55                  60

Asp Pro Gln Phe Val Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn

<210> SEQ ID NO 103
<211> LENGTH: 179
<212> TYPE: PRT
<213> ORGANISM: Artificial Sequence
<220> FEATURE:
<223> OTHER INFORMATION: Synthetic construct

<400> SEQUENCE: 103

Ala Glu Glu Glu Lys Pro Leu Glu Glu Met Glu Phe Ala Ile Ala Asp
1               5                   10                  15

Glu Ile Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Met Arg Pro Glu Thr Ala Leu Ala
        50                  55                  60

Ser Pro Gln Phe Leu Ala Trp Leu Ala Asp Glu Thr Lys Lys Lys Ser
65                  70                  75                  80
```

```
Met Phe Asp Ala Lys Arg Ala Ile Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Ile Ala Ala Val Lys Met Lys
            115                 120                 125

Gln Tyr Glu Ala Val Arg Ser Asp Glu Ala Val Tyr Gly Lys Gly Val
    130                 135                 140

Lys Arg Ser Leu Pro Asp Glu Gln Thr Leu Ala Glu His Leu Val Arg
145                 150                 155                 160

Lys Ala Ala Ala Ile Trp Ala Leu Glu Gln Pro Phe Met Asp Asp Leu
                165                 170                 175

Arg Asn Asn

<210> SEQ ID NO 104
<211> LENGTH: 179
<212> TYPE: PRT
<213> ORGANISM: Artificial Sequence
<220> FEATURE:
<223> OTHER INFORMATION: Synthetic construct

<400> SEQUENCE: 104

Glu Glu Glu Glu Lys Pro Leu Glu Asp Ile Ser Phe Glu Ile Ala Asp
1               5                   10                  15

Glu Val Thr Glu Glu Met Leu Thr Asp Glu Ser Ala Leu Val Val Glu
            20                  25                  30

Val Leu Glu Glu Asn Tyr His Lys Ala Asp Ile Val Gly Phe Ala Ile
        35                  40                  45

Val Asn Glu Asn Gly Asn Phe Phe Ile Pro Thr Asp Thr Ala Leu Ala
    50                  55                  60

Ser Pro Gln Phe Lys Lys Trp Leu Glu Asp Gly Thr Lys Lys Lys Thr
65                  70                  75                  80

Val Phe Asp Ala Lys Arg Ala Ile Val Ala Leu Lys Trp Lys Gly Ile
                85                  90                  95

Glu Leu Lys Gly Val Asp Phe Asp Leu Leu Ile Ala Ser Tyr Leu Leu
            100                 105                 110

Asn Pro Ser Glu Thr Asn Asp Asp Phe Ala Ser Val Ala Lys Thr Lys
            115                 120                 125

Gly Tyr Asn Ala Val Gln Ser Asp Glu Ala Val Tyr Gly Lys Gly Ala
    130                 135                 140

Lys Arg Ala Val Pro Glu Glu Lys Leu Ala Glu His Leu Ala Arg
145                 150                 155                 160

Lys Ala Ala Ala Ile Ser Ala Leu Lys Glu Thr Phe Ile Gln Glu Leu
                165                 170                 175

Lys Glu Asn

<210> SEQ ID NO 105
<211> LENGTH: 179
<212> TYPE: PRT
<213> ORGANISM: Artificial Sequence
<220> FEATURE:
<223> OTHER INFORMATION: Synthetic construct

<400> SEQUENCE: 105

Ala Glu Glu Glu Lys Pro Leu Ala Glu Met Glu Phe Ala Ile Ala Asp
1               5                   10                  15
```

```
Glu Val Thr Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
 50                      55                  60

Asp Ser Gln Phe Leu Ala Trp Leu Ala Asp Glu Thr Lys Lys Lys Ser
 65                  70                  75                  80

Met Phe Asp Ala Lys Arg Ala Val Ala Leu Lys Trp Lys Gly Ile
                 85                  90                  95

Glu Leu Arg Gly Val Ala Phe Asp Leu Leu Ala Ala Tyr Leu Leu
                100                 105                 110

Asn Pro Ala Gln Asp Ala Gly Asp Val Ala Val Ala Lys Met Lys
                115                 120                 125

Gln Tyr Glu Ala Val Arg Ser Asp Glu Ala Val Tyr Gly Lys Gly Ala
130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Leu Asp Glu Leu
                165                 170                 175

Arg Arg Asn
```

<210> SEQ ID NO 106
<211> LENGTH: 179
<212> TYPE: PRT
<213> ORGANISM: Artificial Sequence
<220> FEATURE:
<223> OTHER INFORMATION: Synthetic construct

<400> SEQUENCE: 106

```
Glu Glu Glu Glu Lys Pro Leu Ala Lys Ile Ala Phe Thr Leu Ala Asp
 1               5                  10                  15

Arg Val Thr Asp Glu Met Leu Ala Asp Lys Ala Ala Leu Val Val Glu
                20                  25                  30

Val Val Glu Asp Asn Tyr His Asp Ala Pro Ile Val Gly Ile Ala Val
            35                  40                  45

Val Asn Glu His Gly Arg Phe Phe Leu Arg Pro Glu Thr Ala Leu Ala
 50                      55                  60

Asp Pro Gln Phe Val Ala Trp Leu Gly Asp Glu Thr Lys Lys Lys Ser
 65                  70                  75                  80

Val Phe Asp Ser Lys Arg Ala Val Ala Leu Lys Trp Lys Gly Ile
                 85                  90                  95

Glu Leu Cys Gly Val Ser Phe Asp Leu Leu Leu Ala Ala Tyr Leu Leu
                100                 105                 110

Asp Pro Ala Gln Gly Val Asp Asp Val Ala Ala Ala Lys Met Lys
                115                 120                 125

Gln Tyr His Ala Val Arg Pro Asp Glu Ala Val Tyr Gly Lys Gly Ala
130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn
```

<210> SEQ ID NO 107

```
<211> LENGTH: 179
<212> TYPE: PRT
<213> ORGANISM: Artificial Sequence
<220> FEATURE:
<223> OTHER INFORMATION: Synthetic construct

<400> SEQUENCE: 107

Ala Glu Asp Glu Lys Pro Leu Glu Glu Ile Glu Phe Ala Ile Ala Asp
1               5                   10                  15

Glu Ile Thr Glu Glu Met Leu Ala Asp Lys Ala Ala Leu Val Val Glu
            20                  25                  30

Val Leu Glu Glu Asn Tyr His Asp Ala Pro Ile Val Gly Phe Ala Ile
        35                  40                  45

Val Asn Glu His Gly Arg Phe Phe Ile Arg Pro Glu Thr Ala Leu Ala
    50                  55                  60

Ser Ser Gln Phe Lys Ala Trp Leu Glu Asp Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Ser Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Thr Leu Ala Glu His Leu Val Arg
145                 150                 155                 160

Lys Ala Ala Ile Trp Ala Leu Glu Gln Pro Phe Leu Asp Glu Leu
                165                 170                 175

Arg Glu Asn

<210> SEQ ID NO 108
<211> LENGTH: 179
<212> TYPE: PRT
<213> ORGANISM: Artificial Sequence
<220> FEATURE:
<223> OTHER INFORMATION: Synthetic construct

<400> SEQUENCE: 108

Ala Glu Glu Glu Ala Pro Leu Glu Asp Ile Glu Phe Asp Ile Ala Asp
1               5                   10                  15

Glu Val Thr Glu Glu Met Leu Ala Asp Lys Ala Ala Leu Val Val Glu
            20                  25                  30

Val Gln Glu Asp Asn Tyr His Asp Ala Pro Ile Val Gly Phe Ala Ile
        35                  40                  45

Val Asn Glu His Gly Arg Phe Phe Ile Arg Thr Glu Thr Ala Leu Ala
    50                  55                  60

Ser Glu Ala Phe Lys Ala Trp Leu Ala Asp Glu Thr Lys Lys Lys Ser
65                  70                  75                  80

Val Phe Asp Ala Lys Arg Ala Ile Val Ala Leu Lys Trp Lys Gly Ile
                85                  90                  95

Glu Leu Arg Gly Val Asp Phe Asp Leu Leu Leu Ala Ala Tyr Leu Leu
            100                 105                 110

Asn Pro Ala Gln Thr Ala Asp Asp Val Ala Ala Val Ala Lys Met Lys
        115                 120                 125

Gln Tyr His Ala Val Arg Ser Asp Glu Ala Val Tyr Gly Lys Gly Ala
    130                 135                 140
```

```
Lys Arg Ala Val Pro Asp Glu Pro Val Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Lys Asn

<210> SEQ ID NO 109
<211> LENGTH: 179
<212> TYPE: PRT
<213> ORGANISM: Artificial Sequence
<220> FEATURE:
<223> OTHER INFORMATION: Synthetic construct

<400> SEQUENCE: 109

Ala Glu Asp Glu Lys Pro Leu Ala Glu Met Glu Phe Val Ile Ala Asp
1               5                   10                  15

Gly Ile Thr Asp Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
    50                  55                  60

Asp Pro Gln Phe Val Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Pro Asp Gly Ala Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn

<210> SEQ ID NO 110
<211> LENGTH: 179
<212> TYPE: PRT
<213> ORGANISM: Artificial Sequence
<220> FEATURE:
<223> OTHER INFORMATION: Synthetic construct

<400> SEQUENCE: 110

Thr Glu Glu Glu Val Glu Leu Glu Asp Ile Asn Val Lys Thr Val Thr
1               5                   10                  15

Glu Val Thr Ser Glu Met Leu Thr Asp Pro Ser Ala Leu Val Val Glu
                20                  25                  30

Gln Leu Gly Asp Asn Tyr His Glu Ala Asp Ile Ile Gly Phe Ala Ile
            35                  40                  45

Val Asn Glu Asn Gly Ala Phe Phe Ile Pro Lys Glu Thr Ala Leu Gln
    50                  55                  60

Ser Glu Ala Phe Lys Glu Trp Val Glu Asp Glu Thr Lys Lys Lys Trp
65                  70                  75                  80
```

```
Val Phe Asp Ser Lys Arg Ala Val Val Ala Leu Arg Trp His Gly Ile
                85                  90                  95

Glu Leu Lys Gly Val Asp Phe Asp Val Leu Ala Ser Tyr Ile Ile
            100                 105                 110

Asn Pro Ser Asn Ser Tyr Asp Asp Val Ala Ser Val Ala Lys Glu Tyr
            115                 120                 125

Gly Leu Asn Ile Val Ser Ser Asp Glu Ala Val Tyr Gly Lys Gly Ala
            130                 135                 140

Lys Arg Ala Val Pro Ala Glu Glu Leu Ala Glu His Leu Gly Arg
145                 150                 155                 160

Lys Ala Ala Ala Ile Ser Ala Leu Arg Asp Lys Leu Leu Gln Ala Leu
                165                 170                 175

Glu Glu Asn
```

<210> SEQ ID NO 111
<211> LENGTH: 179
<212> TYPE: PRT
<213> ORGANISM: Artificial Sequence
<220> FEATURE:
<223> OTHER INFORMATION: Synthetic construct

<400> SEQUENCE: 111

```
Ala Glu Lys Glu Leu Pro Leu Met Glu Met Glu Phe Ala Asp Ala Asp
1               5                   10                  15

Thr Ile Thr Met Glu Met Leu Ala Asp Lys Ala Ala Leu Val Val Glu
                20                  25                  30

Val Met Glu Glu Asn Tyr His Asp Ala Pro Ile Val Gly Ile Ala Asn
            35                  40                  45

Val Asn Glu His Gly Arg Phe Phe Leu Arg Thr Glu Leu Ala Leu Ala
        50                  55                  60

Asp Phe Gln Phe Val Ala Trp Leu Glu Asp Glu Thr Lys Lys Lys Ser
65                  70                  75                  80

Met Phe Asp Arg Lys Arg Ala Ala Val Ala Leu Lys Trp Lys Gly Ile
                85                  90                  95

Glu Leu Val Gly Val Asp Phe Asp Leu Leu Leu Ala Ala Tyr Leu Leu
            100                 105                 110

Ala Pro Ala Gln Asp Asp Gly Asp Ala Ala Lys Ala Lys Met Lys
            115                 120                 125

Gln Tyr Glu Ala Val Arg Glu Asp Ala Val Tyr Gly Lys Gly Ala
            130                 135                 140

Lys Arg Pro Asp Pro Asp Glu Leu Ala Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Glu Asn
```

<210> SEQ ID NO 112
<211> LENGTH: 179
<212> TYPE: PRT
<213> ORGANISM: Artificial Sequence
<220> FEATURE:
<223> OTHER INFORMATION: Synthetic construct

<400> SEQUENCE: 112

```
Ala Glu Asp Glu Thr Pro Leu Met Glu Met Glu Phe Val Ile Ala Asp
1               5                   10                  15

Gly Ile Thr Asp Glu Met Leu Ala Asp Lys Ala Ala Leu Val Val Glu
```

```
                 20                  25                  30
Val Gln Glu Glu Asn Tyr His Asp Ala Pro Ile Val Gly Ile Ala Leu
             35                  40                  45
Val Asn Glu His Gly Arg Phe Phe Leu Arg Ala Glu Met Ala Leu Ala
         50                  55                  60
Asp Pro Gln Phe Val Ala Trp Leu Ala Asp Glu Thr Lys Lys Lys Ser
 65                  70                  75                  80
Met Phe Asp Ala Lys Arg Ala Ala Val Ala Leu Lys Trp Lys Gly Ile
                 85                  90                  95
Glu Leu Arg Gly Val Asp Phe Asp Leu Leu Leu Ala Ala Tyr Leu Leu
            100                 105                 110
Asn Pro Ala Gln Thr Asp Glu Asp Val Ala Val Ala Lys Met Lys
            115                 120                 125
Gln Tyr Glu Ala Val Arg Pro Asp Glu Ala Val Tyr Gly Lys Gly Ala
            130                 135                 140
Lys Arg Pro Leu Pro Asp Glu Pro Ala Leu Ala Glu His Leu Val Arg
145                 150                 155                 160
Lys Ala Ala Ala Ile Trp Ala Leu Glu Arg Pro Phe Leu Asp Glu Leu
                165                 170                 175
Arg Ser Asn

<210> SEQ ID NO 113
<211> LENGTH: 179
<212> TYPE: PRT
<213> ORGANISM: Artificial Sequence
<220> FEATURE:
<223> OTHER INFORMATION: Synthetic construct

<400> SEQUENCE: 113

Ala Glu Glu Glu Lys Pro Leu Glu Asp Ile Glu Phe Glu Ile Ala Asp
 1               5                  10                  15
Glu Val Thr Glu Glu Met Leu Ala Asp Glu Ala Ala Leu Val Val Glu
                20                  25                  30
Val Leu Glu Glu Asn Tyr His Asp Ala Pro Ile Val Gly Phe Ala Leu
             35                  40                  45
Val Asn Glu His Gly Arg Phe Phe Ile Arg Thr Glu Thr Ala Leu Ala
         50                  55                  60
Ser Ser Gln Phe Lys Ala Trp Leu Glu Asp Glu Thr Lys Lys Lys Ser
 65                  70                  75                  80
Val Phe Asp Ala Lys Arg Ala Ile Val Ala Leu Lys Trp Lys Gly Ile
                 85                  90                  95
Glu Leu Arg Gly Val Asp Phe Asp Leu Leu Leu Ala Ala Tyr Leu Leu
            100                 105                 110
Asn Pro Ala Gln Ser Ala Gly Asp Val Ala Ala Val Lys Met Lys
            115                 120                 125
Gln Tyr Glu Ala Val Arg Ser Asp Glu Ala Val Tyr Gly Lys Gly Ala
            130                 135                 140
Lys Arg Ala Val Pro Asp Glu Pro Thr Leu Ala Glu His Leu Val Arg
145                 150                 155                 160
Lys Ala Ala Ala Ile Trp Ala Leu Glu Glu Pro Phe Ile Asp Glu Leu
                165                 170                 175
Arg Glu Asn

<210> SEQ ID NO 114
<211> LENGTH: 179
```

```
<212> TYPE: PRT
<213> ORGANISM: Artificial Sequence
<220> FEATURE:
<223> OTHER INFORMATION: Synthetic construct

<400> SEQUENCE: 114

Ser Glu Glu Lys Pro Leu Ala Lys Met Ala Phe Thr Leu Ala Asp
1               5                   10                  15

Glu Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Val
        35                  40                  45

Val Asn Glu His Gly Arg Phe Phe Leu Arg Pro Glu Thr Ala Leu Ala
    50                  55                  60

Ser Pro Gln Phe Val Ala Trp Leu Gly Asp Glu Thr Lys Lys Lys Ser
65                  70                  75                  80

Met Phe Asp Ser Lys Arg Ala Ile Val Ala Leu Lys Trp Lys Gly Ile
                85                  90                  95

Glu Leu Cys Gly Val Ser Phe Asp Leu Leu Leu Ala Ala Tyr Leu Leu
            100                 105                 110

Asp Pro Ala Gln Gly Val Asp Asp Val Ala Ala Ala Lys Met Lys
        115                 120                 125

Gln Tyr Glu Ala Val Arg Pro Asp Glu Ala Val Tyr Gly Lys Gly Ala
    130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn

<210> SEQ ID NO 115
<211> LENGTH: 179
<212> TYPE: PRT
<213> ORGANISM: Artificial Sequence
<220> FEATURE:
<223> OTHER INFORMATION: Synthetic construct

<400> SEQUENCE: 115

Ala Glu Gly Glu Lys Pro Leu Ala Glu Met Glu Phe Ala Ile Val Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140
```

```
Lys Arg Ser Leu Pro Asp Glu Pro Thr Leu Ala Glu His Leu Val Arg
145                 150                 155                 160

Lys Ala Ala Ala Ile Trp Ala Leu Glu Gln Pro Phe Ile Asp Glu Leu
                165                 170                 175

Arg Arg Asn

<210> SEQ ID NO 116
<211> LENGTH: 179
<212> TYPE: PRT
<213> ORGANISM: Artificial Sequence
<220> FEATURE:
<223> OTHER INFORMATION: Synthetic construct

<400> SEQUENCE: 116

Ala Glu Glu Glu Lys Pro Leu Ala Glu Met Glu Phe Thr Ile Ala Asp
1               5                   10                  15

Glu Val Thr Glu Glu Met Leu Ala Asp Lys Ala Ala Leu Val Val Glu
                20                  25                  30

Val Leu Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
    50                  55                  60

Asp Ser Gln Phe Leu Ala Trp Leu Gly Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Ala Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ala Val Pro Asp Glu Pro Val Leu Glu His Leu Val Arg
145                 150                 155                 160

Lys Ala Ala Ala Ile Trp Ala Leu Glu Glu Pro Phe Ile Asp Glu Leu
                165                 170                 175

Arg Arg Asn

<210> SEQ ID NO 117
<211> LENGTH: 179
<212> TYPE: PRT
<213> ORGANISM: Artificial Sequence
<220> FEATURE:
<223> OTHER INFORMATION: Synthetic construct

<400> SEQUENCE: 117

Ala Glu Glu Glu Lys Pro Leu Glu Glu Met Glu Phe Ala Ile Ala Asp
1               5                   10                  15

Glu Val Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
    50                  55                  60

Ser Pro Gln Phe Lys Ala Trp Leu Ala Asp Glu Thr Lys Lys Lys Ser
65                  70                  75                  80
```

```
Met Phe Asp Ala Lys Arg Ala Ile Val Ala Leu Lys Trp Lys Gly Ile
                 85                  90                  95

Glu Leu Arg Gly Val Ala Phe Asp Leu Leu Ala Ala Tyr Leu Leu
            100                 105                 110

Asn Pro Ala Gln Asp Ala Gly Asp Val Ala Val Ala Lys Met Lys
            115                 120                 125

Gln Tyr Glu Ala Val Arg Ser Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Asn Asn

<210> SEQ ID NO 118
<211> LENGTH: 179
<212> TYPE: PRT
<213> ORGANISM: Artificial Sequence
<220> FEATURE:
<223> OTHER INFORMATION: Synthetic construct

<400> SEQUENCE: 118

Ala Glu Glu Glu Lys Pro Leu Ala Glu Met Glu Phe Ala Ile Ala Asp
1               5                   10                  15

Ser Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Gly Asp Glu Thr Lys Lys Lys Ser
65                  70                  75                  80

Met Phe Asp Ser Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Val Ala Lys Met Lys
            115                 120                 125

Gln Tyr Glu Ala Val Arg Ser Asp Glu Ala Val Tyr Gly Lys Gly Ala
        130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Arg Asn

<210> SEQ ID NO 119
<211> LENGTH: 179
<212> TYPE: PRT
<213> ORGANISM: Artificial Sequence
<220> FEATURE:
<223> OTHER INFORMATION: Synthetic construct
```

```
<400> SEQUENCE: 119

Ala Glu Glu Glu Lys Pro Leu Ala Glu Met Glu Phe Ala Ile Ala Asp
1               5                   10                  15

Glu Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Thr Glu Thr Ala Leu Ala
    50                  55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                85                  90                  95

Glu Leu Arg Gly Val Asp Phe Asp Leu Leu Ala Ala Tyr Leu Leu
                100                 105                 110

Asn Pro Ala Gln Asp Ala Gly Asp Val Ala Val Ala Lys Met Lys
                115                 120                 125

Gln Tyr Glu Ala Val Arg Ser Asp Glu Ala Val Tyr Gly Lys Gly Ala
        130                 135                 140

Lys Arg Ala Leu Pro Asp Glu Pro Thr Leu Ala Glu His Leu Val Arg
145                 150                 155                 160

Lys Ala Ala Ala Ile Trp Ala Leu Glu Glu Pro Phe Leu Asp Glu Leu
                165                 170                 175

Arg Glu Asn

<210> SEQ ID NO 120
<211> LENGTH: 179
<212> TYPE: PRT
<213> ORGANISM: Artificial Sequence
<220> FEATURE:
<223> OTHER INFORMATION: Synthetic construct

<400> SEQUENCE: 120

Ser Glu Glu Glu Lys Pro Leu Ala Lys Ile Ala Phe Asp Leu Ala Asp
1               5                   10                  15

Arg Val Thr Glu Glu Met Leu Ala Asp Lys Ala Ala Leu Val Val Glu
                20                  25                  30

Val Gln Glu Asp Asn Tyr His Asp Ala Pro Ile Val Gly Ile Ala Val
        35                  40                  45

Val Asn Glu His Gly Arg Phe Phe Leu Arg Ala Glu Leu Ala Leu Ala
    50                  55                  60

Ser Pro Gln Phe Val Ala Trp Leu Gly Asp Glu Thr Lys Lys Lys Ser
65                  70                  75                  80

Met Phe Asp Ser Lys Arg Ala Ile Val Ala Leu Lys Trp Lys Gly Ile
                85                  90                  95

Glu Leu Cys Gly Val Asp Phe Asp Leu Leu Ala Ala Tyr Leu Leu
                100                 105                 110

Asp Pro Ala Gln Thr Asp Asp Ala Ala Lys Ala Lys Met Lys
                115                 120                 125

Gln Tyr His Ala Val Arg Pro Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160
```

```
Lys Ala Ala Ala Ile Trp Ala Leu Glu Glu Pro Phe Leu Asp Glu Leu
                165                 170                 175

Arg Arg Asn
```

<210> SEQ ID NO 121
<211> LENGTH: 179
<212> TYPE: PRT
<213> ORGANISM: Artificial Sequence
<220> FEATURE:
<223> OTHER INFORMATION: Synthetic construct

<400> SEQUENCE: 121

```
Ala Glu Asp Glu Lys Pro Leu Ala Glu Met Glu Phe Ala Ile Ala Asp
1               5                   10                  15

Gly Ile Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Val Ala Val Ala Lys Met Lys
        115                 120                 125

Gln Tyr Glu Ala Val Arg Ser Asp Glu Val Tyr Gly Lys Gly Ala
    130                 135                 140

Lys Arg Ser Leu Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Ser Asn
```

<210> SEQ ID NO 122
<211> LENGTH: 179
<212> TYPE: PRT
<213> ORGANISM: Artificial Sequence
<220> FEATURE:
<223> OTHER INFORMATION: Synthetic construct

<400> SEQUENCE: 122

```
Ala Glu Glu Glu Lys Pro Leu Glu Gly Met Glu Phe Ala Ile Ala Asp
1               5                   10                  15

Glu Val Thr Glu Glu Met Leu Ala Asp Lys Ala Ala Leu Val Val Glu
            20                  25                  30

Val Met Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Ala Asp Glu Thr Lys Lys Lys Ser
65                  70                  75                  80

Met Phe Asp Ala Lys Arg Ala Ala Val Ala Leu Lys Trp Lys Gly Ile
                85                  90                  95
```

Glu Leu Arg Gly Val Ala Phe Asp Leu Leu Ala Ala Tyr Leu Leu
                100                 105                 110

Asn Pro Ala Gln Asp Ala Gly Asp Val Ala Ala Val Ala Lys Met Lys
            115                 120                 125

Gln Tyr Glu Ala Val Arg Ser Asp Glu Ala Val Tyr Gly Lys Gly Ala
        130                 135                 140

Lys Arg Ala Val Pro Asp Glu Pro Val Leu Ala Glu His Leu Val Arg
145                 150                 155                 160

Lys Ala Ala Ala Ile Trp Ala Leu Glu Arg Pro Phe Leu Asp Glu Leu
                165                 170                 175

Arg Arg Asn

<210> SEQ ID NO 123
<211> LENGTH: 179
<212> TYPE: PRT
<213> ORGANISM: Artificial Sequence
<220> FEATURE:
<223> OTHER INFORMATION: Synthetic construct

<400> SEQUENCE: 123

Glu Glu Glu Glu Glu Pro Leu Glu Asp Ile Ser Phe Glu Ile Val Glu
1               5                   10                  15

Glu Val Thr Glu Asp Met Leu Thr Asp Glu Ser Ala Leu Val Val Glu
            20                  25                  30

Val Leu Glu Glu Asn Tyr His Lys Ala Asp Ile Val Gly Phe Ala Ile
        35                  40                  45

Ala Asn Glu Asn Gly Asn Phe Phe Ile Pro Thr Asp Thr Ala Leu Ala
    50                  55                  60

Ser Glu Ala Phe Lys Lys Trp Leu Glu Asp Thr Lys Lys Lys Ser
65                  70                  75                  80

Val Phe Asp Ala Lys Arg Ala Ile Val Ala Leu Lys Trp His Gly Ile
                85                  90                  95

Glu Leu Lys Gly Val Asp Phe Asp Leu Leu Ile Ala Ser Tyr Leu Leu
                100                 105                 110

Asn Pro Ser Glu Ser Ser Asp Asp Phe Ala Ser Val Ala Lys Thr Lys
            115                 120                 125

Gly Tyr Asn Ala Val Gln Ser Asp Glu Ala Val Tyr Gly Lys Gly Ala
        130                 135                 140

Lys Arg Ala Val Pro Asp Glu Glu Lys Leu Ala Glu His Leu Ala Arg
145                 150                 155                 160

Lys Ala Ala Ala Ile Ser Ala Leu Lys Glu Thr Phe Ile His Glu Leu
                165                 170                 175

Lys Glu Asn

<210> SEQ ID NO 124
<211> LENGTH: 179
<212> TYPE: PRT
<213> ORGANISM: Artificial Sequence
<220> FEATURE:
<223> OTHER INFORMATION: Synthetic construct

<400> SEQUENCE: 124

Glu Glu Glu Glu Glu Pro Leu Glu Asp Ile Ser Phe Glu Ile Val Glu
1               5                   10                  15

Glu Val Thr Glu Glu Met Leu Thr Asp Glu Ser Ala Leu Val Val Glu
            20                  25                  30

Val Leu Glu Glu Asn Tyr His Lys Ala Asp Ile Val Gly Phe Ala Ile
           35                  40                  45

Val Asn Glu Asn Gly Asn Phe Phe Ile Pro Thr Asp Thr Ala Leu Ala
 50                      55                  60

Ser Glu Ala Phe Lys Lys Trp Leu Glu Asp Thr Lys Lys Lys Thr
65                  70                  75                  80

Val Phe Asp Ala Lys Arg Ala Ile Val Ala Leu Lys Trp Lys Gly Ile
                    85                  90                  95

Glu Leu Lys Gly Val Asp Phe Asp Leu Leu Ile Ala Ser Tyr Leu Leu
                100                 105                 110

Asn Pro Ser Glu Thr Asn Asp Asp Phe Ala Ser Val Ala Lys Thr Lys
                115                 120                 125

Gly Tyr Asn Ala Val Gln Ser Asp Glu Ala Val Tyr Gly Lys Gly Ala
            130                 135                 140

Lys Arg Ala Val Pro Glu Glu Glu Lys Leu Ala Glu His Leu Ala Arg
145                 150                 155                 160

Lys Ala Ala Ala Ile Ser Ala Leu Lys Glu Thr Phe Ile Gln Glu Leu
                    165                 170                 175

Lys Glu Asn

<210> SEQ ID NO 125
<211> LENGTH: 179
<212> TYPE: PRT
<213> ORGANISM: Artificial Sequence
<220> FEATURE:
<223> OTHER INFORMATION: Synthetic construct

<400> SEQUENCE: 125

Ala Glu Glu Glu Lys Pro Leu Glu Glu Met Glu Phe Ala Ile Ala Asp
1               5                   10                  15

Glu Val Thr Glu Glu Met Leu Ala Asp Lys Ala Ala Leu Val Val Glu
                20                  25                  30

Val Met Glu Glu Asn Tyr His Asp Ala Pro Ile Val Gly Ile Ala Leu
            35                  40                  45

Val Asn Glu His Gly Arg Phe Phe Leu Arg Pro Glu Thr Ala Leu Ala
 50                     55                  60

Asp Pro Gln Phe Lys Ala Trp Leu Ala Asp Glu Thr Lys Lys Lys Ser
65                  70                  75                  80

Met Phe Asp Ala Lys Arg Ala Ile Val Ala Leu Lys Trp Lys Gly Ile
                    85                  90                  95

Glu Leu Arg Gly Val Ala Phe Asp Leu Leu Leu Ala Ala Tyr Leu Leu
                100                 105                 110

Asn Pro Ala Gln Asp Ala Asp Asp Val Ala Val Ala Lys Met Lys
                115                 120                 125

Gln Tyr Glu Ala Val Arg Ser Asp Glu Ala Val Tyr Gly Lys Gly Ala
            130                 135                 140

Lys Arg Ala Val Pro Asp Glu Pro Val Leu Ala Glu His Leu Val Arg
145                 150                 155                 160

Lys Ala Ala Ala Ile Arg Ala Leu Glu Arg Pro Phe Leu Asp Glu Leu
                    165                 170                 175

Arg Asn Asn

<210> SEQ ID NO 126
<211> LENGTH: 179
<212> TYPE: PRT
<213> ORGANISM: Artificial Sequence
<220> FEATURE:
<223> OTHER INFORMATION: Synthetic construct

<400> SEQUENCE: 126

Ala Glu Glu Glu Lys Pro Leu Ala Glu Met Glu Phe Ala Ile Ala Asp
1               5                   10                  15

Ser Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Leu
        35                  40                  45

Val Asn Glu His Gly Arg Phe Phe Leu Arg Pro Glu Thr Ala Leu Ala
    50                  55                  60

Asp Pro Gln Phe Leu Ala Trp Leu Gly Asp Glu Thr Lys Lys Lys Ser
65                  70                  75                  80

Met Phe Asp Ser Lys Arg Ala Ala Val Ala Leu Lys Trp Lys Gly Ile
                85                  90                  95

Glu Leu Arg Gly Val Ala Phe Asp Leu Leu Leu Ala Ala Tyr Leu Leu
            100                 105                 110

Asn Pro Ala Gln Ala Ala Gly Asp Val Ala Ala Val Ala Lys Met Lys
        115                 120                 125

Gln Tyr Glu Ala Val Arg Ser Asp Glu Ala Val Tyr Gly Lys Gly Ala
    130                 135                 140

Lys Arg Ser Val Pro Asp Glu Pro Thr Leu Ala Glu His Leu Val Arg
145                 150                 155                 160

Lys Ala Ala Ala Ile Trp Ala Leu Glu Gln Pro Phe Met Asp Glu Leu
                165                 170                 175

Arg Arg Asn

<210> SEQ ID NO 127
<211> LENGTH: 46
<212> TYPE: DNA
<213> ORGANISM: Artificial Sequence
<220> FEATURE:
<223> OTHER INFORMATION: Synthetic construct

<400> SEQUENCE: 127
cagccagccg cagcacgttc gctcatagga gatatggtag agccgc                  46

<210> SEQ ID NO 128
<211> LENGTH: 51
<212> TYPE: DNA
<213> ORGANISM: Artificial Sequence
<220> FEATURE:
<223> OTHER INFORMATION: Synthetic construct

<400> SEQUENCE: 128
gagagaattt gtaccacctc ccaccgggca catagcagtc ctagggacag t             51

<210> SEQ ID NO 129
<211> LENGTH: 22
<212> TYPE: DNA
<213> ORGANISM: Artificial Sequence
<220> FEATURE:
<223> OTHER INFORMATION: Synthetic construct

<400> SEQUENCE: 129
ggcttggctc tgctaacacg tt                                            22

```
<210> SEQ ID NO 130
<211> LENGTH: 22
<212> TYPE: DNA
<213> ORGANISM: Artificial Sequence
<220> FEATURE:
<223> OTHER INFORMATION: Synthetic construct

<400> SEQUENCE: 130
ggacgtttgt aatgtccgct cc                                              22

<210> SEQ ID NO 131
<211> LENGTH: 17
<212> TYPE: DNA
<213> ORGANISM: Artificial Sequence
<220> FEATURE:
<223> OTHER INFORMATION: Synthetic construct

<400> SEQUENCE: 131
ctgcatacga cgtgtct                                                    17

<210> SEQ ID NO 132
<211> LENGTH: 20
<212> TYPE: DNA
<213> ORGANISM: Artificial Sequence
<220> FEATURE:
<223> OTHER INFORMATION: Synthetic construct

<400> SEQUENCE: 132
accatctatg actgtacgcc                                                 20

<210> SEQ ID NO 133
<211> LENGTH: 24
<212> TYPE: DNA
<213> ORGANISM: Artificial Sequence
<220> FEATURE:
<223> OTHER INFORMATION: Synthetic construct

<400> SEQUENCE: 133
cgccagggtt ttcccagtca cgac                                            24

<210> SEQ ID NO 134
<211> LENGTH: 20
<212> TYPE: DNA
<213> ORGANISM: Artificial Sequence
<220> FEATURE:
<223> OTHER INFORMATION: Synthetic construct

<400> SEQUENCE: 134
agaacgggaa gcttgtcatc                                                 20

<210> SEQ ID NO 135
<211> LENGTH: 18
<212> TYPE: DNA
<213> ORGANISM: Artificial Sequence
<220> FEATURE:
<223> OTHER INFORMATION: Synthetic construct

<400> SEQUENCE: 135
cgaacatggg ggcatcag                                                   18
```